(12) United States Patent
Aranda et al.

(10) Patent No.: US 10,011,847 B2
(45) Date of Patent: Jul. 3, 2018

(54) ALPHAVIRAL VECTORS AND CELL LINES FOR PRODUCING RECOMBINANT PROTEINS

(71) Applicant: 3P BIOPHARMACEUTICALS, S.L., Noain (Navarra) (ES)

(72) Inventors: Alejandro Aranda, Noain (ES); Jaione Bezunartea Bezunartea, Noain (ES); Cristian Smerdou Picazo, Noain (ES); Damaso Molero Sánchez, Noain (ES); Edita Mistiene, Noain (ES); Andreu Soldevila Fàbrega, Noain (ES); Paula Serrano Pérez-Nievas, Noain (ES)

(73) Assignee: 3P BIOPHARMACEUTICALS, S.L., Noain (Navarra) (ES)

( * ) Notice: Subject to any disclaimer, the term of this patent is extended or adjusted under 35 U.S.C. 154(b) by 0 days.

(21) Appl. No.: 14/892,829

(22) PCT Filed: May 20, 2014

(86) PCT No.: PCT/ES2014/070416
§ 371 (c)(1),
(2) Date: Nov. 20, 2015

(87) PCT Pub. No.: WO2014/188042
PCT Pub. Date: Nov. 27, 2014

(65) Prior Publication Data
US 2016/0208286 A1 Jul. 21, 2016

(30) Foreign Application Priority Data
May 20, 2013 (ES) .................................. 201330722

(51) Int. Cl.
*C12N 15/86* (2006.01)
*C12N 7/00* (2006.01)

(52) U.S. Cl.
CPC .............. *C12N 15/86* (2013.01); *C12N 7/00* (2013.01); *C12N 2770/36141* (2013.01); *C12N 2800/30* (2013.01); *C12N 2840/203* (2013.01)

(58) Field of Classification Search
None
See application file for complete search history.

(56) References Cited

U.S. PATENT DOCUMENTS

| | | | |
|---|---|---|---|
| 5,089,397 A | 2/1992 | Kushner et al. |
| 6,057,134 A | 5/2000 | Lader et al. |
| 6,287,813 B1 | 9/2001 | Fussenegger et al. |
| 6,355,420 B1 | 3/2002 | Chan |
| 6,436,640 B1 | 8/2002 | Simmons |
| 6,451,579 B1 | 9/2002 | Jessee et al. |
| 6,458,583 B1 | 10/2002 | Bruhn et al. |
| 6,461,816 B1 | 10/2002 | Wolber |
| 6,465,183 B2 | 10/2002 | Wolber |
| 6,465,254 B1 | 10/2002 | Saito et al. |
| 6,524,793 B1 | 2/2003 | Chandler et al. |
| 6,534,314 B1 | 3/2003 | Bouhassira et al. |
| 6,632,526 B1 | 10/2003 | Chandler et al. |
| 6,891,032 B2 | 5/2005 | Brown et al. |
| 6,916,661 B2 | 7/2005 | Chandler et al. |
| 7,026,124 B2 | 4/2006 | Barth et al. |
| 7,052,841 B2 | 5/2006 | Delenstarr |
| 7,060,809 B2 | 6/2006 | Wengel et al. |
| 7,122,303 B2 | 10/2006 | Delenstarr et al. |
| 2003/0170871 A1 | 9/2003 | Dubensky, Jr. et al. |
| 2004/0132086 A1 | 7/2004 | Horwitz et al. |
| 2007/0087366 A1 | 4/2007 | Holt et al. |
| 2007/0224170 A1 | 9/2007 | Qian et al. |
| 2010/0055736 A1 | 3/2010 | Smerdou Picazo et al. |

FOREIGN PATENT DOCUMENTS

| | | |
|---|---|---|
| EP | 736099 A1 | 10/2001 |
| EP | 804565 A1 | 9/2005 |
| WO | 8604920 A1 | 8/1986 |
| WO | 9738087 A2 | 10/1997 |
| WO | 9738117 A1 | 10/1997 |
| WO | 9918226 A2 | 4/1999 |
| WO | 9925851 A1 | 5/1999 |
| WO | 2000006205 A1 | 2/2000 |
| WO | 0063410 A1 | 10/2000 |
| WO | 2000060091 A2 | 10/2000 |
| WO | 0142442 A2 | 6/2001 |
| WO | 2001081553 A1 | 11/2001 |

(Continued)

OTHER PUBLICATIONS

Sorrell, et al. (Apr. 5, 2010 online) "Recombinase mediated cassette exchange into genomic targets using an adenovirus vector", Nucleic Acids Research, 38(11): e123 (12 pages).*
Aranda, et al. (2014) "A quick and efficient method to generate mammalian stable cell lines based on a novel inducible alphavirus DNA/RNA layered system", Cellular and Molecular Life Sciences, 71: 4637-51.*
Baron et al., "Co-regulation of two gene activities by tetracycline via a bidirectional promoter," Nucleic Acids Res., 1995, 17:3605-3606.
Gossen, M. et al., "Transcriptional Activation by Tetracyclines in Mammalian Cells," 1995, Science 268: 1766-1769.
No et al., "Ecdysone-inducible gene expression in mammalian cells and transgenic mice," 1996, Proc Natl Acad Sci, 93: 3346-3351.
Rivera et al., "A humanized system for pharmacologic control of gene expression," 1996, Nat.Med.2:1028-32.
Bethke and Sauer, "Segmental genomic replacement by Cre-mediated recombination: genotoxic stress activation of the p53 promoter in single-copy transformants," Nucleic Acids Res., 1997, 25: 2828-2834.

(Continued)

*Primary Examiner* — Robert M Kelly
(74) *Attorney, Agent, or Firm* — Tristan A. Fuierer; Moore & Van Allen, PLLC

(57) ABSTRACT

The present invention relates to polynucleotides and alphaviral vectors for the expression of genes of interest in mammalian cells. Additionally, the invention relates to cells which comprise said polynucleotides and alphaviral vectors and are capable of stably expressing one or more genes of interest. The invention also relates to methods for obtaining said cells, to methods for expressing a gene of interest in said cells, and to methods for replacing the gene of interest stably expressed by said cells with another gene of interest.

32 Claims, 19 Drawing Sheets

(56) References Cited

FOREIGN PATENT DOCUMENTS

| WO | 0393293 | 11/2003 |
|---|---|---|
| WO | 200519244 | 3/2005 |
| WO | 2005112541 A2 | 12/2005 |
| WO | 2007085906 A2 | 8/2007 |
| WO | 2008026015 A2 | 3/2008 |
| WO | 2008065225 A2 | 6/2008 |
| WO | 2011064437 A2 | 6/2011 |
| WO | 2012001196 A2 | 1/2012 |

OTHER PUBLICATIONS

Wang et al., "Ligand-inducible and liver-s[ecific target gene expression in transgenic mice," Nature Biotech., 1997; 15:239-43.
Agapov et al., "Noncytopathic Sindbis virus RNA vectors for heterologous gene expression," 1998, Proc. Natl. Acad. Sci. USA. 95: 12989-94.
Rossi, F.M.V. and Blau H.M., "Recent advances in inducible gene expression systems," 1998, Curr Opin Biotechnol 9: 451-456.
Suhr et al., "High level transactivation by a modified Bombyx ecdysone receptor in mammalian cells without exogenous retinoid X receptor," 1998, Proc. Natl. Acad. Sci., 95: 7999-8004.
Burcin et al., "Adenovirus-mediated regulable target gene expression in vivo," Proc. Natl. Acad. Sci. USA, 1999, 36:355-60.
Frolov et al., "Selection of RNA Replicons Capable of Persistent Noncytopathic Replication in Mammalian Cells," 1999, J. Virol. 73: 3854-65.
Perri et al., "Replicon Vectors Derived from Sindbis Virus and Semliki Forest Virus That Establish Persistent Replication in Host Cells," 2000, J. Virol. 74: 9802-7.
Arakawa et al., "Mutant loxP vectors for selectable marker recycle and conditional knock-outs," 2001. BMC Biotechnology, 1: 7.
Lundstrom et al., "Novel mutant Semliki Forest virus vectors: gene expression and localization studies in neuronal cells," 2001. Histochem. Cell. Biol. 115: 83-91.
Manickan et al., "Conditional Liver-Specific Expression of SV40 T Antigen Leads to Regulatable Development of Hepatic Neoplasm in Transgenic Mice," J. Biol. Chem., 2001, 276:13989-13994.
Kramer et al., "In Vitro and in Vivo Comparative Study of Chimeric Liver-Specific Promoters," 2003. Mol. Ther. 7, 375-85.
Tietge et al., "A tetracycline-regulated adenoviral expression system for in vivo delivery of transgenes to lung and liver," J.Gene. Medicine, 2003, 5:567-575.
Zabala et al., "Optimization of the Tet-on System to Regulate Interleukin 12 Expression in the Liver for the Treatment of Hepatic Tumors," 2004, Cancer Research, 64: 2799-2804.
Terpe K., "Overview of tag protein fusions: from molecular and biochemical fundamentals to commercial systems," 2003, Appl. Microbiol. Biotechnol. 60: 523-525.
Han et al., "Glucose-Dependent Insulin Production by Liver-Specific, Glucose-Regulatable Synthetic Promoters Results in the Cure of Diabetes," Molecular Therapy, 2005, 11, S161.
Crettaz et al., "Gene Therapy of Chronic Hepatitis B Infection Using a High-Capacity Adenovirus Expressing Interleukin 12 under the Control of a Liver Specific Mifepristone-Inducible Promoter," Molecular Therapy (2006) 13, S224.
Casales et al. "Development of a new noncytopathic Semliki Forest virus vector providing high expression levels and stability," 2008. Virology. 376:242-51.
Rausalu K. et al., "Properties and use of novel replication-competent vectors based on Semliki Forest virus," 2009 Virol J. 6: 33.
Lee and Saito, "Role of nucleotide sequences of loxP spacer region in Cre-mediated recombination," Gene 1998, 216: 55-65.
Ryan and Drew; "Foot-and-mouth disease virus 2A oligopeptide mediated cleavage of an artificial polyprotein," EMBO J. 1994,13: 928-33.
Hartman S.C. and Mulligan R.C., "Two dominant-acting selectable markers for gene transfer studies in mammalian cells," 1988, Proc. Natl. Acad. Sci. USA. 85(21): 8047-51.

Kaufman R.J. and Sharp P.A., "Amplification and Expression of Sequences Cotransfected with a Modular Dihydrofolate Reductase Complementary DNA Gene," 1982, J. Mol. Biol., 159(4): 601-21.
Scott et al., "The structure and function of the homeodomain," 1989, Biochim. Biophys. Acta 989:25-48.
Rosenfeld et al., "POU-domain transcription factors: pou-er-ful developmental regulators," 1991, Genes Dev. 5:897-907.
Palli et al., "Improved ecdysone receptor-based inducible gene regulation system," 2003, Eur. J. Biochem., 270: 1308-1315.
Ho et al., "Dimeric ligands define a role for transcriptional activation domains in reinitiation," 1996, Nature, 382: 322-826.
Amara et al., "A versatile synthetic dimerizer for the regulation of protein—protein interactions," 1997, Proc. Natl. Acad. Sci. USA, 94: 10618-10623.
Zhao et al., A Coumermycin/Novobiocin-Regulated Gene Expression System, 2003, Hum. Gene Ther., 14: 1619-1629.
Seipel, K. et al.; "Different activation domains stimulate transcription from remote ('enhancer') and proximal ('promoter') positions," EMBO J. (1992) 13:4961-4968.
Triezenberg, S. J. et al.; "Functional dissection of VP16, the transactivator of herpes simplex virus immediate early gene expression," Genes Dev., 1988, 2:718-729.
Baron et al., "Tetracycline-controlled transcription in eukaryotes:novel transactivators with graded transactivation potential," Nucleic Acids. Res., 1997, 25:2723-2729.
Urlinger, S. et al., "Exploring the sequence space for tetracyclinedependent transcriptional activators: Novel mutations yield expanded range and sensitivity," Proc.Natl.Acad.Sci USA, 2000; 97:7963-7968.
Neely, et al., "A single-molecule method for the quantitation of microRNA gene expression," Nat. Methods. 3(1):41-6 (2006).
Lu, et al., "MicroRNA expression profiles classify human cancers," Nature 435:7043 (2005).
Nelson, et al., "MicroRNA expression profiles classify human cancers," Nat. Methods I(2):155-61 (2004).
Wang H et al., "Direct and sensitive miRNA profiling from low-input total RNA," RNA 13(1):151-9 (2007) (wrongly cited in the application as Wu et al., RNA 13(1):151-9 (2007)).
Liljestrom and Garoff, "A New Generation of Animal Cell Expression Vectors Based on the Semliki Forest Virus Replicon," 1991, Biotechnology (N Y). 1991 9:1356-61.
Vanrell et al. "Development of a Liver-specific Tet-On Inducible System for AAV Vectors and Its Application in the Treatment of Liver Cancer," 2011. Mol Ther. 19:1245-53.
Berglund et al. "Enhancing immune responses using suicidal DNA vaccies," 1998. Nat Biotechnol. 16:562-5.
Berraondo et al. "IFN-Alpha Gene Therapy for Woodchuck Hepatitis with Adeno-associated Virus: Differences in Duration of Gene Expression and Antiviral Activity Using Intraportal or Intramuscular Routes," 2005. Mol. Ther.12:68-76.
de la Luna et al. "Efficient transformation of mammalian cells with constructs containing a puromycin-resistance marker," 1988. Gene, 62:121-6.
Casales et al. "A novel system for the production of high levels of functional human therapeutic proteins in stable cells with a Semliki Forest virus noncytopathic vector," 2010. N Biotechnol. 27:138-48.
Larrea, Aldabe et al., "Oncostatin M Enhances the Antiviral Effects of Type I Interferon and Activates Immunostimulatory Functions in Liver Epithelial Cells," 2009, J Virol 83(7): 3298-3311.
Horn et al., "Regulation of Cell Growth by Recombinant Oncostatin M," 1990, Growth Factors 2(2-3): 157-65.
Karlsson, G.B. et al., "Delivery and expression of heterologous genes in mammalian cells using self-replicating alphavirus vectors," Methods Mol. Biol., 2004, vol. 246, pp. 543-557.
Riezebos-Brilman, A. et al, Recombinant alphaviruses as vectors for anti-tumour and anti-microbial immunotherapy, Journal of Clinical Virology, 2006, vol. 35, pp. 233-243.
Geiss, B.J. et at, 'Recombination-ready Sindbis replicon expression vectors for transgene expression', Virology Journal, 2007, vol. 4, pp. 112.

(56) References Cited

OTHER PUBLICATIONS

Wang, Y. et al, "Recombinase technology: applications and possibilities," Plant Cell Reports, 2011, vol. 30, pp. 267-285.

Steel, J.J. et al, "Infectious alphavirus production from a simple plasmid transfection+," Virology Journal, 2011, vol. 8, pp. 356.

Quetglas, J.I. et al, "Alphavirus vectors for cancer therapy," Virus Research, 2010, vol. 153, pp. 179-196.

International Search Report, dated Aug. 4, 2014.

Aranda, Alejandro, et al.; "A quick and efficient method to generate mammalian stable cell lines based on a novel inducible alphavirus DNA/RNA layered system," Cell. Mol. Life Sci., 2014, pp. 4637-4651, vol. 71.

Branda, Catherine S.; "Talking about a Revolution: The Impact of Site-Specific Recombinases on Genetic Analyses in Mice," Developmental Cell, 2004, pp. 7-28, vol. 6.

Boorsma, Marco, et al.; "Alphavirus cDNA-Based Expression Vectors," Biotechnology and Bioengineering, 2003, pp. 553-562, vol. 81.

Du, Zhong-Wei, et al.; Cre Recombination Mediated Cassette Exchange for Building Versatile Transgenic Human ESC Lines, Stem Cells, 2009, pp. 1032-1041, vol. 27.

Fang, Jianmin, et al.; "Stable antibody expression at therapeutic levels using the 2A peptide," Nature Biotechnology, 2005, pp. 584-590, vol. 23.

Wilke, Sonja, et al.; "Streamlining Homogeneous Glycoprotein Production for Biophysical and Structural Applications by Targeted Cell Line Development," PLOS One, 2011, pp. 1-8, vol. 6.

Abremski and Hoess, "Bacteriophage P1 Site-specific Recombination," 1984, J. Biol. Chem. 259: 1509-1514.

Chothia, C. et al, "Canonical Structures for the Hypervariable Regions of Immunoglobulins," (1987) J. Mol. Biol. 196:901-917.

Kinney, et al., "The Full-Length Nucleotide Sequences of the Virulent Trinidad Donkey Strain of Veneuelan Equine Encephalitis Virus and Its Attenuated Vaccine Derivative, Strain TC-83," 1989, Virology, 170:19-30.

Christopherson et al., "Ecdysteroid-dependent regulation of genes in mammalian cells by a *Drosophila* ecdysone receptor and chimeric transactivators," 1992, Proc Natl Acad Sci, 89: 6314-6318.

Gossen, M. and H. Bujard, "Tight control of gene expression in mammalian cells by tetracydine-responsive promoters," 1992, Proc Natl Acad Sci, 89: 5547-5551.

Strauss and Strauss, "The Alphaviruses: Gene Expression, Replication, and Evolution," Microbiol. Rev., 58:491-562, 1994.

\* cited by examiner

SEQUENCE LISTING

```
<160> NUMBER OF SEQ ID NOS: 70

<210> SEQ ID NO 1
<211> LENGTH: 86
<212> TYPE: DNA
<213> ORGANISM: Semliki Forest virus

<400> SEQUENCE: 1
gatggcggat gtgtgacata cacgacgcca aaagattttg ttccagctcc tgccacctcc      60
gctacgcgag agattaacca cccacg                                          86

<210> SEQ ID NO 2
<211> LENGTH: 7296
<212> TYPE: DNA
<213> ORGANISM: Artificial Sequence
<220> FEATURE:
<223> OTHER INFORMATION: Synthetic Construct

<400> SEQUENCE: 2
atggccgcca aagtgcatgt tgatattgag gctgacagcc cattcatcaa gtctttgcag      60
aaggcatttc cgtcgttcga ggtggagtca ttgcaggtca caccaaatga ccatgcaaat     120
gccagagcat tttcgcacct ggctaccaaa ttgatcgagc aggagactga caaagacaca     180
ctcatcttgg atatcggcag tgcgccttcc aggagaatga tgtctacgca caaataccac     240
tgcgtatgcc ctatgcgcag cgcagaagac cccgaaaggc tcgatagcta cgcaaagaaa     300
ctggcagcgg cctccgggaa ggtgctggat agagagatcg caggaaaaat caccgacctg     360
cagaccgtca tggctacgcc agacgctgaa tctcctacct tttgcctgca tacagacgtc     420
acgtgtcgta cggcagccga agtggccgta taccaggacg tgtatgctgt acatgcacca     480
acatcgctgt accatcaggc gatgaaaggt gtcagaacgg cgtattggat tgggtttgac     540
accaccccgt ttatgtttga cgcgctagca ggcgcgtatc caacctacgc cacaaactgg     600
gccgacgagc aggtgttaca ggccaggaac ataggactgt gtgcagcatc cttgactgag     660
ggaagactcg gcaaactgtc cattctccgc aagaagcaat tgaaaccttg cgacacagtc     720
atgttctcgg taggatctac attgtacact gagagcagaa agctactgag gagctggcac     780
ttaccctccg tattccacct gaaaggtaaa caatccttta cctgtaggtg cgataccatc     840
```

```
gtatcatgtg aagggtacgt agttaagaaa atcactatgt gccccggcct gtacggtaaa      900
acggtagggt acgccgtgac gtatcacgcg gagggattcc tagtgtgcaa gaccacagac      960
actgtcaaag gagaaagagt ctcattccct gtatgcacct acgtcccctc aaccatctgt     1020
gatcaaatga ctggcatact agcgaccgac gtcacaccgg aggacgcaca gaagttgtta     1080
gtgggattga atcagaggat agttgtgaac ggaagaacac agcgaaacac taacacgatg     1140
aagaactatc tgcttccgat tgtggccgtc gcatttagca agtgggcgag ggaatacaag     1200
gcagaccttg atgatgaaaa acctctgggt gtccgagaga ggtcacttac ttgctgctgc     1260
ttgtgggcat ttaaaacgag gaagatgcac accatgtaca agaaaccaga cacccagaca     1320
atagtgaagg tgccttcaga gtttaactcg ttcgtcatcc cgagcctatg gtctacaggc     1380
ctcgcaatcc cagtcagatc acgcattaag atgcttttgg ccaagaagac caagcgagag     1440
ttaatacctg ttctcgacgc gtcgtcagcc agggatgctg aacaagagga aaggagagg      1500 ttggaggccg agctgactag agaagcctta ccaccccteg tccccategc gccggcggag     1560 acgggagtcg tcgacgtcga cgttgaagaa ctagagtatc acgcaggtgc aggggtcgtg     1620
gaaacacctc gcagcgcgtt gaaagtcacc gcacagccga acgacgtact actaggaaat     1680
tacgtagttc tgtccccgca gaccgtgctc aagagctcca agttggcccc cgtgcaccct     1740
ctagcagagc aggtgaaaat aataacacat aacgggaggg ccggcggtta ccaggtcgac     1800
ggatatgacg gcagggtcct actaccatgt ggatcggcca ttccggtccc tgagtttcaa     1860
gctttgagcg agagcgccac tatggtgtac aacgaaaggg agttcgtcaa caggaaacta     1920
taccatattg ccgttcacgg accgtcgctg aacaccgacg aggagaacta cgagaaagtc     1980
agagctgaaa gaactgacgc cgagtacgtg ttcgacgtag ataaaaaatg ctgcgtcaag     2040
agagaggaag cgtcgggttt ggtgttggtg ggagagctaa ccaaccccc gttccatgaa      2100 ttcgcctacg aagggctgaa gatcaggccg tcggcaccat ataagactac agtagtagga     2160
gtctttgggg ttccgggatc aggcaagtct gctattatta agagcctcgt gaccaaacac     2220
gatctggtca ccagcggcaa gaaggagaac tgccaggaaa tagttaacga cgtgaagaag     2280
caccgcggga aggggacaag tagggaaaac agtgactcca tcctgctaaa cgggtgtcgt     2340
cgtgccgtgg acatcctata tgtggacgag gctttcgctt gccattccgg tactctgctg     2400
gccctaattg ctcttgttaa acctcggagc aaagtggtgt tatgcggaga ccccaagcaa     2460
tgcggattct tcaatatgat gcagcttaag gtgaacttca ccacaacat ctgcactgaa      2520 gtatgtcata aaagtatatc cagacgttgc acgcgtccag tcacggccat cgtgtctacg     2580
ttgcactacg aggcaagat gcgcacgacc aacccgtgca caaacccat aatcatagac       2640 accacaggac agaccaagcc caagccagga gacatcgtgt taacatgctt ccgaggctgg     2700
gcaaagcagc tgcagttgga ctaccgtgga cacgaagtca tgacagcagc agcatctcag     2760
ggcctcaccc gcaaagggt atacgccgta aggcagaagg tgaatgaaaa tcccttgtat     2820 gccccctgcgt cggagcacgt gaatgtactg ctgacgcgca ctgaggatag gctggtgtgg     2880
aaaacgctgg ccggcgatcc ctggattaag gtcctatcaa acattccaca gggtaacttt     2940
acggccacat tggaagaatg gcaagaagaa cacgacaaaa taatgaaggt gattgaagga     3000
ccggctgcgc ctgtggacgc gttccagaac aaagcgaacg tgtgttgggc gaaaagcctg     3060
gtgcctgtcc tggacactgc cggaatcaga ttgacagcag aggagtggag caccataatt     3120
acagcattta aggaggacag agcttactct ccagtggtgg ccttgaatga aatttgcacc     3180
aagtactatg gagttgacct ggacagtggc ctgtttttctg ccccgaaggt gtccctgtat     3240
```

```
tacgagaaca accactggga taacagacct ggtggaagga tgtatggatt caatgccgca    3300
acagctgcca ggctggaagc tagacatacc ttcctgaagg ggcagtggca tacgggcaag    3360
caggcagtta tcgcagaaag aaaaatccaa ccgctttctg tgctggacaa tgtaattcct    3420
atcaaccgca ggctgccgca cgccctggtg gctgagtaca agacggttaa aggcagtagg    3480
gttgagtggc tggtcaataa agtaagaggg taccacgtcc tgctggtgag tgagtacaac    3540
ctggctttgc ctcgacacag ggtcacttgg ttgtcaccgc tgaatgtcac aggcgccgat    3600
aggtgctacg acctaagttt aggactgccg gctgacgccg gcaggttcga cttggtcttt    3660
gtgaacattc acacggaatt cagaatccac cactaccagc agtgtgtcga ccacgccatg    3720
aagctgcaga tgcttggggg agatgcgcta cgactgctaa aaacgggcgg catcttgatg    3780
agagcttacg gatacgccga taaaatcagc gaagccgttg tttcctcctt aagcagaaag    3840
ttctcgtctg caagagtgtt gcgcccggat tgtgtcacca gcaatacaga agtgttcttg    3900
ctgttctcca actttgacaa cggaaagaga ccctctacgc tacaccagat gaataccaag    3960
ctgagtgccg tgtatgccgg agaagccatg cacacggccg ggtgtgcacc atcctacaga    4020
gttaagagag cagacatagc cacgtgcaca gaagcggctg tggttaacgc agctaacgcc    4080
cgtggaactg taggggatgg cgtatgcagg gccgtggcga agaaatggcc gtcagccttt    4140
aagggagcag caacaccagt gggcacaatt aaaacagtca tgtgcggctc gtaccccgtc    4200
atccacgctg tagcgcctaa tttctctgcc acgactgaag cggaagggga ccgcgaattg    4260
gccgctgtct accgggcagt ggccgccgaa gtaaacagac tgtcactgag cagcgtagcc    4320
atcccgctgc tgtccacagg agtgttcagc ggcggaagag ataggctgca gcaatccctc    4380
aaccatctat tcacagcaat ggacgccacg gacgctgacg tgaccatcta ctgcagagac    4440
aaaagttggg agaagaaaat ccaggaagcc attgacatga ggacggctgt ggagttgctc    4500
aatgatgacg tggagctgac cacagacttg gtgagagtgc acccggacag cagcctggtg    4560
ggtcgtaagg gctacagtac cactgacggg tcgctgtact cgtactttga aggtacgaaa    4620
ttcaaccagg ctgctattga tatggcgagg atactgacgt tgtggccag actgcaagag    4680
gcaaacgaac agatatgcct atacgcgctg ggcgaaacaa tggacaacat cagatccaaa    4740
tgtccggtga acgattccga ttcatcaaca cctcccagga cagtgccctg cctgtgccgc    4800
tacgcaatga cagcagaacg gatcgcccgc cttaggtcac accaagttaa aagcatggtg    4860
gtttgctcat cttttcccct cccgaaatac catgtagatg gggtgcagaa ggtaaagtgc    4920
gagaaggttc tcctgttcga cccgacggta ccttcagtgg ttagtccgcg gaagtatgcc    4980
gcatctacga cggaccactc agatcggtcg ttacgagggt ttgacttgga ctggaccacc    5040
gactcgtctt ccactgccag cgataccatg tcgctaccca gtttgcagtc gtgtgacatc    5100
gactcgatct acgagccaat ggctcccata gtagtgacgg ctgacgtaca ccctgaaccc    5160
gcaggcatcg cggacctggc ggcagatgtg caccctgaac ccgcagacca tgtggacctc    5220
gagaacccga ttcctccacc gcgcccgaag agagctgcat accttgcctc ccgcgcggcg    5280
gagcgaccgg tgccggcgcc gagaaagccg acgcctgccc caaggactgc gtttaggaac    5340
aagctgcctt tgacgttcgg cgactttgac gagcacgagg tcgatgcgtt ggcctccggg    5400
attactttcg gagacttcga cgacgtcctg cgactaggcc gcgcgggtgc atatatttc    5460
tcctcggaca ctggcagcgg acatttacaa caaaaatccg ttaggcagca caatctccag    5520
tgcgcacaac tggatgcggt ccaggaggag aaaatgtacc cgccaaaatt ggatactgag    5580
```

-continued

```
agggagaagc tgttgctgct gaaaatgcag atgcacccat cggaggctaa taagagtcga     5640
taccagtctc gcaaagtgga gaacatgaaa gccacggtgg tggacaggct cacatcgggg     5700
gccagattgt acacgggagc ggacgtaggc cgcataccaa catacgcggt tcggtacccc     5760
cgccccgtgt actccctac cgtgatcgaa agattctcaa gccccgatgt agcaatcgca      5820
gcgtgcaacg aatacctatc cagaaattac ccaacagtgg cgtcgtacca gataacagat     5880
gaatacgacg catacttgga catggttgac gggtcggata gttgcttgga cagagcgaca     5940
ttctgcccgg cgaagctccg gtgctacccg aaacatcatg cgtaccacca gccgactgta     6000
cgcagtgccg tcccgtcacc ctttcagaac acactacaga acgtgctagc ggccgccacc     6060
aagagaaact gcaacgtcac gcaaatgcga gaactaccca ccatggactc ggcagtgttc     6120
aacgtggagt gcttcaagcg ctatgcctgc tccggagaat attgggaaga atatgctaaa     6180
caacctatcc ggataaccac tgagaacatc actacctatg tgaccaaatt gaaaggcccg     6240
aaagctgctg ccttgttcgc taagaccac aacttggttc cgctgcagga ggttcccatg      6300
gacagattca cggtcgacat gaaacgagat gtcaaagtac tcccagggac gaaacacaca     6360
gaggaaagac ccaaagtcca ggtaattcaa gcagcggagc cattggcgac cgcttacctg     6420
tgcggcatcc acagggaatt agtaaggaga ctaaatgctg tgttacgccc taacgtgcac     6480
acattgtttg atatgtcggc cgaagacttt gacgcgatca tcgcctctca cttccaccca     6540
ggagacccgt tctagagac ggacattgca tcattcgaca aaagccagga cgactccttg      6600
gctcttacag gtttaatgat cctcgaagat ctaggggtgg atcagtacct gctggacttg     6660
atcgaggcag ccttgggga atatccagc tgtcacctac caactggcac gcgcttcaag       6720
ttcggagcta tgatgaaatc gggcatgttt ctgactttgt ttattaacac tgttttgaac     6780
atcaccatag caagcagggt actggagcag agactcactg actccgcctg tgcggccttc     6840
atcggcgacg acaacatcgt tcacggagtg atctccgaca agctgatggc ggagaggtgc     6900
gcgtcgtggg tcaacatgga ggtgaagatc attgacgctg tcatgggcga aaaaccccca     6960
tatttttgtg ggggattcat agtttttgac agcgtcacac agaccgcctg ccgtgtttca     7020
gacccactta gcgcctgtt caagttgggt aagccgctaa cagctgaaga caagcaggac      7080
gaagacaggc gacgagcact gagtgacgag gttagcaagt ggttccggac aggcttgggg     7140
gccgaactgg aggtggcact aacatctagg tatgaggtag agggctgcaa aagtatcctc     7200
atagccatgg ccaccttggc gagggacatt aaggcgttta agaaattgag aggacctgtt     7260
atacacctct acggcggtcc tagattggtg cgttaa                               7296
```

<210> SEQ ID NO 3
<211> LENGTH: 840
<212> TYPE: DNA
<213> ORGANISM: Semliki Forest virus

<400> SEQUENCE: 3
attacatccc tacgcaaacg ttttacggcc gccggtggcg cccgcgcccg gcggcccgtc 60
cttggccgtt gcaggccact ccggtggctc ccgtcgtccc cgacttccag gcccagcaga 120
tgcagcaact catcagcgcc gtaaatgcgc tgacaatgag acagaacgca attgctcctg 180
ctaggcctcc caaaccaaag aagaagaaga caaccaaacc aaagccgaaa acgcagccca 240
agaagatcaa cggaaaaacg cagcagcaaa agaagaaaga caagcaagcc gacaagaaga 300
agaagaaacc cggaaaaaga gaaagaatgt gcatgaagat tgaaaatgac tgtatcttcg 360
tatgcggcta gccacagtaa cgtagtgttt ccagacatgt cgggcaccgc actatcatgg 420

```
gtgcagaaaa tctcgggtgg tctgggggcc ttcgcaatcg cgctatcct ggtgctggtt      480 ggtgtcactt gcattgggct ccgcagataa gttagggtag gcaatggcat tgatatagca      540
agaaaattga aaacagaaaa agttagggta agcaatggca tataaccata actgtataac      600
ttgtaacaaa gcgcaacaag acctgcgcaa ttggccccgt ggtccgcctc acggaaactc      660
ggggcaactc atattgacac attaattggc aataattgga agcttacata agcttaattc      720
gacgaataat tggattttta ttttattttg caattggttt ttaatatttc caaaaaaaaa      780
aaaaaaaaaa aaaaaaaaaa aaaaaaaaaa aaaaaaaaaa aaaaaaaaaa aaaaaaaaaa      840

<210> SEQ ID NO 4
<211> LENGTH: 503
<212> TYPE: DNA
<213> ORGANISM: Artificial Sequence
<220> FEATURE:
<223> OTHER INFORMATION: Synthetic Construct

<400> SEQUENCE: 4
tcgagtttac cactccctat cagtgataga gaaaagtgaa agtcgagttt accactccct       60
atcagtgata gagaaaagtg aaagtcgagt ttaccactcc ctatcagtga tagagaaaag      120
tgaaagtcga gtttaccact ccctatcagt gatagagaaa agtgaaagtc gagtttacca      180
ctccctatca gtgatagaga aaagtgaaag tcgagtttac cactccctat cagtgataga      240
gaaaagtgaa agtcgagttt accactccct atcagtgata gagaaaagtg aaagtcgagc      300
tcggtacaca gctccagatg gcaaacatac gcaaggggatt tagtcaaaca acttttttggc      360 aaagatggta tgattttgta atgggggtagg aaccaatgaa atgcgaggta agtatggtta      420
atgatctaca gttattggtt aaagaagtat attagagcga gtctttctgc acacacgatc      480 accttttccta tcaaccccac tat                                             503

<210> SEQ ID NO 5
<211> LENGTH: 467
<212> TYPE: DNA
<213> ORGANISM: Artificial Sequence
<220> FEATURE:
<223> OTHER INFORMATION: Synthetic Construct

<400> SEQUENCE: 5
tcgagtttac cactccctat cagtgataga gaaaagtgaa agtcgagttt accactccct       60
atcagtgata gagaaaagtg aaagtcgagt ttaccactcc ctatcagtga tagagaaaag      120
tgaaagtcga gtttaccact ccctatcagt gatagagaaa agtgaaagtc gagtttacca      180
ctccctatca gtgatagaga aaagtgaaag tcgagtttac cactccctat cagtgataga      240
gaaaagtgaa agtcgagttt accactccct atcagtgata gagaaaagtg aaagtcgagc      300
tcggtacaca gctccagatg gcaaacatac gcaagggatt tagtcaaaca acttttggc       360 aaagatggta tgattttgta atgggggtagg aaccaatgaa atgcgaggta agtatggtta      420
atgatctaca gttattggtt aaagaagtat attagagcga gtctttc                    467

<210> SEQ ID NO 6
<211> LENGTH: 479
<212> TYPE: DNA
<213> ORGANISM: Artificial Sequence
<220> FEATURE:
<223> OTHER INFORMATION: Synthetic Construct

<400> SEQUENCE: 6
```

```
tcgagtttac cactccctat cagtgataga gaaaagtgaa agtcgagttt accactccct    60
atcagtgata gagaaaagtg aaagtcgagt ttaccactcc ctatcagtga tagagaaaag   120
tgaaagtcga gtttaccact ccctatcagt gatagagaaa agtgaaagtc gagtttacca   180
ctccctatca gtgatagaga aaagtgaaag tcgagtttac cactccctat cagtgataga   240
gaaaagtgaa agtcgagttt accactccct atcagtgata gagaaaagtg aaagtcgagc   300
tcggtacaca gctccagatg gcaaacatac gcaagggatt tagtcaaaca acttttggc    360 aaagatggta tgattttgta atggggtagg aaccaatgaa atgcgaggta agtatggtta   420
atgatctaca gttattggtt aaagaagtat attagagcga gtctttctgc acacacgat    479

<210> SEQ ID NO 7
<211> LENGTH: 480
<212> TYPE: DNA
<213> ORGANISM: Artificial Sequence
<220> FEATURE:
<223> OTHER INFORMATION: Synthetic Construct

<400> SEQUENCE: 7
tcgagtttac cactccctat cagtgataga gaaaagtgaa agtcgagttt accactccct    60
atcagtgata gagaaaagtg aaagtcgagt ttaccactcc ctatcagtga tagagaaaag   120
tgaaagtcga gtttaccact ccctatcagt gatagagaaa agtgaaagtc gagtttacca   180
ctccctatca gtgatagaga aaagtgaaag tcgagtttac cactccctat cagtgataga   240
gaaaagtgaa agtcgagttt accactccct atcagtgata gagaaaagtg aaagtcgagc   300
tcggtacaca gctccagatg gcaaacatac gcaagggatt tagtcaaaca acttttggc    360 aaagatggta tgattttgta atggggtagg aaccaatgaa atgcgaggta agtatggtta   420
atgatctaca gttattggtt aaagaagtat attagagcga gtctttctgc acacacgatc   480

<210> SEQ ID NO 8
<211> LENGTH: 481
<212> TYPE: DNA
<213> ORGANISM: Artificial Sequence
<220> FEATURE:
<223> OTHER INFORMATION: Synthetic Construct

<400> SEQUENCE: 8
tcgagtttac cactccctat cagtgataga gaaaagtgaa agtcgagttt accactccct    60
atcagtgata gagaaaagtg aaagtcgagt ttaccactcc ctatcagtga tagagaaaag   120
tgaaagtcga gtttaccact ccctatcagt gatagagaaa agtgaaagtc gagtttacca   180
ctccctatca gtgatagaga aaagtgaaag tcgagtttac cactccctat cagtgataga   240
gaaaagtgaa agtcgagttt accactccct atcagtgata gagaaaagtg aaagtcgagc   300
tcggtacaca gctccagatg gcaaacatac gcaagggatt tagtcaaaca acttttggc    360 aaagatggta tgattttgta atggggtagg aaccaatgaa atgcgaggta agtatggtta   420
atgatctaca gttattggtt aaagaagtat attagagcga gtctttctgc acacacgatc   480
a                                                                   481

<210> SEQ ID NO 9
<211> LENGTH: 34
<212> TYPE: DNA
<213> ORGANISM: Artificial Sequence
<220> FEATURE:
<223> OTHER INFORMATION: Synthetic Construct

<400> SEQUENCE: 9
```
taccgttcgt ataaagtatc ctatacgaag ttat                              34

<210> SEQ ID NO 10
<211> LENGTH: 34
<212> TYPE: DNA
<213> ORGANISM: Artificial Sequence
<220> FEATURE:
<223> OTHER INFORMATION: Synthetic Construct

<400> SEQUENCE: 10
taccgttcgt ataatgtgta ctatacgaag ttat                              34

<210> SEQ ID NO 11
<211> LENGTH: 34
<212> TYPE: DNA
<213> ORGANISM: Artificial Sequence
<220> FEATURE:
<223> OTHER INFORMATION: Synthetic Construct

<400> SEQUENCE: 11
ataacttcgt ataaagtatc ctatacgaac ggta                              34

<210> SEQ ID NO 12
<211> LENGTH: 34
<212> TYPE: DNA
<213> ORGANISM: Artificial Sequence
<220> FEATURE:
<223> OTHER INFORMATION: Synthetic Construct

<400> SEQUENCE: 12
ataacttcgt ataatgtgta ctatacgaac ggta                              34

<210> SEQ ID NO 13
<211> LENGTH: 381
<212> TYPE: DNA
<213> ORGANISM: Simian virus 40

<400> SEQUENCE: 13
cgcccttccc aacagttgcg cagcctgaat ggcgaatgga gatccaattt ttaagtgtat    60
aatgtgttaa actactgatt ctaattgttt gtgtatttta gattcacagt cccaaggctc   120
atttcaggcc cctcagtcct cacagtctgt tcatgatcat aatcagccat accacatttg   180
tagaggtttt acttgcttta aaaaacctcc cacacctccc cctgaacctg aaacataaaa   240
tgaatgcaat tgttgttgtt aacttgttta ttgcagctta taatggttac aaataaagca   300
atagcatcac aaatttcaca aataaagcat ttttttcact gcattctagt tgtggtttgt   360
ccaaactcat caatgtatct t                                            381

<210> SEQ ID NO 14
<211> LENGTH: 317
<212> TYPE: DNA
<213> ORGANISM: Simian virus 40

<400> SEQUENCE: 14
ggtgtggaaa gtccccaggc tccccagcag gcagaagtat gcaaagcatg catctcaatt    60
agtcagcaac caggtgtgga agtcccccag gctccccagc aggcagaagt atgcaaagca   120
tgcatctcaa ttagtcagca accatagtcc cgcccctaac tccgcccatc ccgcccctaa   180
ctccgcccag ttccgcccat tctccgcccc atggctgact aatttttttt atttatgcag   240
aggccgaggc cgcctcggcc tctgagctat tccagaagta gtgaggaggc ttttttggag   300

```
gcctaggctt ttgcaaa                                              317
```

<210> SEQ ID NO 15
<211> LENGTH: 13
<212> TYPE: PRT
<213> ORGANISM: herpes simplex virus 7

<400> SEQUENCE: 15

Pro Ala Asp Ala Leu Asp Asp Phe Asp Leu Asp Met Leu
1               5                   10

<210> SEQ ID NO 16
<211> LENGTH: 747
<212> TYPE: DNA
<213> ORGANISM: Artificial Sequence
<220> FEATURE:
<223> OTHER INFORMATION: Synthetic Construct

<400> SEQUENCE: 16

```
atgtctagac tggacaagag caaagtcata acggcgctc tggaattact caatggagtc      60
ggtatcgaag gcctgacgac aaggaaactc gctcaaaagc tgggagttga gcagcctacc    120
ctgtactggc acgtgaagaa caagcgggcc ctgctcgatg ccctgccaat cgagatgctg    180
gacaggcatc atacccactt ctgccccctg gaaggcgagt catggcaaga ctttctgcgg    240
aacaacgcca gtcattccg ctgtgctctc ctctcacatc gcgacggggc taaagtgcat     300
ctcggcaccc gcccaacaga gaaacagtac gaaaccctgg aaaatcagct cgcgttcctg    360
tgtcagcaag gcttctccct ggagaacgca ctgtacgctc tgtccgccgt gggccacttt    420
acactgggct gcgtattgga ggaacaggag catcaagtag caaaagagga agagagacaca   480 cctaccaccg attctatgcc cccacttctg agacaagcaa ttgagctgtt cgaccggcag    540
ggagccgaac tgccttcct tttcggcctg gaactaatca tatgtggcct ggagaaacag     600
ctaaagtgcg aaagcggcgg gccggccgac gcccttgacg attttgactt agacatgctc    660
ccagccgatg cccttgacga cttttgacctt gatatgctgc ctgctgacgc tcttgacgat    720
tttgaccttg acatgctccc cgggtaa                                        747
```

<210> SEQ ID NO 17
<211> LENGTH: 25
<212> TYPE: DNA
<213> ORGANISM: Artificial Sequence
<220> FEATURE:
<223> OTHER INFORMATION: Synthetic Construct

<400> SEQUENCE: 17

```
cccgggatga aaagcctga actca                                            25
```

<210> SEQ ID NO 18
<211> LENGTH: 28
<212> TYPE: DNA
<213> ORGANISM: Artificial Sequence
<220> FEATURE:
<223> OTHER INFORMATION: Synthetic Construct

<400> SEQUENCE: 18

```
gcggccgcct attcctttgc cctcggac                                        28
```

<210> SEQ ID NO 19
<211> LENGTH: 23
<212> TYPE: DNA
<213> ORGANISM: Artificial Sequence
<220> FEATURE:

<223> OTHER INFORMATION: Synthetic Construct

<400> SEQUENCE: 19
atggcggatg tgtgacatac acg                                          23

<210> SEQ ID NO 20
<211> LENGTH: 47
<212> TYPE: DNA
<213> ORGANISM: Artificial Sequence
<220> FEATURE:
<223> OTHER INFORMATION: Synthetic Construct

<400> SEQUENCE: 20
gctcctcgcc cttgctcacc atcgtgggtg gttaatctct cgcgtag                47

<210> SEQ ID NO 21
<211> LENGTH: 20
<212> TYPE: DNA
<213> ORGANISM: Artificial Sequence
<220> FEATURE:
<223> OTHER INFORMATION: Synthetic Construct

<400> SEQUENCE: 21
atggtgagca agggcgagga                                              20

<210> SEQ ID NO 22
<211> LENGTH: 30
<212> TYPE: DNA
<213> ORGANISM: Artificial Sequence
<220> FEATURE:
<223> OTHER INFORMATION: Synthetic Construct

<400> SEQUENCE: 22
actagtctta agatacattg atgagtttgg                                   30

<210> SEQ ID NO 23
<211> LENGTH: 39
<212> TYPE: DNA
<213> ORGANISM: Artificial Sequence
<220> FEATURE:
<223> OTHER INFORMATION: Synthetic Construct

<400> SEQUENCE: 23
atgcatcgcg atagcggtac cgagctctta cgctcgagt                         39

<210> SEQ ID NO 24
<211> LENGTH: 56
<212> TYPE: DNA
<213> ORGANISM: Artificial Sequence
<220> FEATURE:
<223> OTHER INFORMATION: Synthetic Construct

<400> SEQUENCE: 24
ggtggcagga gctggaacaa aatcttttgg cgtcgtgtat gtcacacatc cgccat      56

<210> SEQ ID NO 25
<211> LENGTH: 82
<212> TYPE: DNA
<213> ORGANISM: Artificial Sequence
<220> FEATURE:
<223> OTHER INFORMATION: Synthetic Construct

<400> SEQUENCE: 25
ggtggcagga gctggaacaa aatcttttgg cgtcgtgtat gtcacacatc cgccatgatc  60
gtgtgtgcag aaagactcgc tc                                           82

<210> SEQ ID NO 26
<211> LENGTH: 83
<212> TYPE: DNA
<213> ORGANISM: Artificial Sequence
<220> FEATURE:
<223> OTHER INFORMATION: Synthetic Construct

<400> SEQUENCE: 26
ggtggcagga gctggaacaa aatcttttgg cgtcgtgtat gtcacacatc cgccatatgt    60
cgtgtgtgca gaaagactcg ctc    83

<210> SEQ ID NO 27
<211> LENGTH: 25
<212> TYPE: DNA
<213> ORGANISM: Artificial Sequence
<220> FEATURE:
<223> OTHER INFORMATION: Synthetic Construct

<400> SEQUENCE: 27
agagctcggc cgcctcggcc tctga    25

<210> SEQ ID NO 28
<211> LENGTH: 22
<212> TYPE: DNA
<213> ORGANISM: Artificial Sequence
<220> FEATURE:
<223> OTHER INFORMATION: Synthetic Construct

<400> SEQUENCE: 28
atgcatggcg gtaatacggt ta    22

<210> SEQ ID NO 29
<211> LENGTH: 23
<212> TYPE: DNA
<213> ORGANISM: Artificial Sequence
<220> FEATURE:
<223> OTHER INFORMATION: Synthetic Construct

<400> SEQUENCE: 29
atggcggatg tgtgacatac acg    23

<210> SEQ ID NO 30
<211> LENGTH: 27
<212> TYPE: DNA
<213> ORGANISM: Artificial Sequence
<220> FEATURE:
<223> OTHER INFORMATION: Synthetic Construct

<400> SEQUENCE: 30
gggcccgata tccaagatga gtgtgtc    27

<210> SEQ ID NO 31
<211> LENGTH: 62
<212> TYPE: DNA
<213> ORGANISM: Artificial Sequence
<220> FEATURE:
<223> OTHER INFORMATION: Synthetic Construct

<400> SEQUENCE: 31
actagtataa cttcgtatag tacacattat acgaacggta gtgggcgaag aactccagca    60
tg    62

<210> SEQ ID NO 32

<210> SEQ ID NO 32
<211> LENGTH: 28
<212> TYPE: DNA
<213> ORGANISM: Artificial Sequence
<220> FEATURE:
<223> OTHER INFORMATION: Synthetic Construct

<400> SEQUENCE: 32
ggatccatgg tgagcaaggg cgaggagc                                28

<210> SEQ ID NO 33
<211> LENGTH: 43
<212> TYPE: DNA
<213> ORGANISM: Artificial Sequence
<220> FEATURE:
<223> OTHER INFORMATION: Synthetic Construct

<400> SEQUENCE: 33
cccgggatct taattaatta cttgtacagc tcgtccatgc cga                43

<210> SEQ ID NO 34
<211> LENGTH: 39
<212> TYPE: DNA
<213> ORGANISM: Artificial Sequence
<220> FEATURE:
<223> OTHER INFORMATION: Synthetic Construct

<400> SEQUENCE: 34
gatctaccgt tcgtataaag tatcctatac gaagttatc                    39

<210> SEQ ID NO 35
<211> LENGTH: 39
<212> TYPE: DNA
<213> ORGANISM: Artificial Sequence
<220> FEATURE:
<223> OTHER INFORMATION: Synthetic Construct

<400> SEQUENCE: 35
gatcgataac ttcgtatagg atactttata cgaacggta                    39

<210> SEQ ID NO 36
<211> LENGTH: 28
<212> TYPE: DNA
<213> ORGANISM: Artificial Sequence
<220> FEATURE:
<223> OTHER INFORMATION: Synthetic Construct

<400> SEQUENCE: 36
catatgtacc gttcgtataa agtatcct                                28

<210> SEQ ID NO 37
<211> LENGTH: 30
<212> TYPE: DNA
<213> ORGANISM: Artificial Sequence
<220> FEATURE:
<223> OTHER INFORMATION: Synthetic Construct

<400> SEQUENCE: 37
actagtgcta tggcagggcc tgccgccccg                              30

<210> SEQ ID NO 38
<211> LENGTH: 28
<212> TYPE: DNA
<213> ORGANISM: Artificial Sequence
<220> FEATURE:
<223> OTHER INFORMATION: Synthetic Construct

<400> SEQUENCE: 38
gatatcgtga ggctccggtg cccgtcag                                                28

<210> SEQ ID NO 39
<211> LENGTH: 44
<212> TYPE: DNA
<213> ORGANISM: Artificial Sequence
<220> FEATURE:
<223> OTHER INFORMATION: Synthetic Construct

<400> SEQUENCE: 39
gcggccgctt cacgacacct gaaatggaag aaaaaaactt tgaa                              44

<210> SEQ ID NO 40
<211> LENGTH: 62
<212> TYPE: DNA
<213> ORGANISM: Artificial Sequence
<220> FEATURE:
<223> OTHER INFORMATION: Synthetic Construct

<400> SEQUENCE: 40
tataacttcg tataaagtat cctatacgaa cggtatctag atctcgcgag ctcagccata            60
tg                                                                          62

<210> SEQ ID NO 41
<211> LENGTH: 59
<212> TYPE: DNA
<213> ORGANISM: Artificial Sequence
<220> FEATURE:
<223> OTHER INFORMATION: Synthetic Construct

<400> SEQUENCE: 41
tatggctgag ctcgcgagat ctagataccg ttcgtatagg atactttata cgaagttat             59

<210> SEQ ID NO 42
<211> LENGTH: 28
<212> TYPE: DNA
<213> ORGANISM: Artificial Sequence
<220> FEATURE:
<223> OTHER INFORMATION: Synthetic Construct

<400> SEQUENCE: 42
catatgttag ggtaggcaat ggcattga                                                28

<210> SEQ ID NO 43
<211> LENGTH: 27
<212> TYPE: DNA
<213> ORGANISM: Artificial Sequence
<220> FEATURE:
<223> OTHER INFORMATION: Synthetic Construct

<400> SEQUENCE: 43
cagctgctgg cttaactatg cggcatc                                                 27

<210> SEQ ID NO 44
<211> LENGTH: 46
<212> TYPE: DNA
<213> ORGANISM: Artificial Sequence
<220> FEATURE:
<223> OTHER INFORMATION: Synthetic Construct

<400> SEQUENCE: 44
catgggatca taacttcgta taatgtgtac tatacgaacg gccatg                           46

<210> SEQ ID NO 45

```
<211> LENGTH: 46
<212> TYPE: DNA
<213> ORGANISM: Artificial Sequence
<220> FEATURE:
<223> OTHER INFORMATION: Synthetic Construct

<400> SEQUENCE: 45
gatccatggc cgttcgtata gtacacatta tacgaagtta tgatcc          46

<210> SEQ ID NO 46
<211> LENGTH: 31
<212> TYPE: DNA
<213> ORGANISM: Artificial Sequence
<220> FEATURE:
<223> OTHER INFORMATION: Synthetic Construct

<400> SEQUENCE: 46
agatctgcac catggtgagc aagggcgagg a                          31

<210> SEQ ID NO 47
<211> LENGTH: 28
<212> TYPE: DNA
<213> ORGANISM: Artificial Sequence
<220> FEATURE:
<223> OTHER INFORMATION: Synthetic Construct

<400> SEQUENCE: 47
catatgttac ttgtacagct cgtccatg                              28

<210> SEQ ID NO 48
<211> LENGTH: 33
<212> TYPE: DNA
<213> ORGANISM: Artificial Sequence
<220> FEATURE:
<223> OTHER INFORMATION: Synthetic Construct

<400> SEQUENCE: 48
agatctgcac catgtcggcc ctgctgatcc tgg                        33

<210> SEQ ID NO 49
<211> LENGTH: 27
<212> TYPE: DNA
<213> ORGANISM: Artificial Sequence
<220> FEATURE:
<223> OTHER INFORMATION: Synthetic Construct

<400> SEQUENCE: 49
catatgtcag gccgagcccc cgggcag                               27

<210> SEQ ID NO 50
<211> LENGTH: 101
<212> TYPE: DNA
<213> ORGANISM: Artificial Sequence
<220> FEATURE:
<223> OTHER INFORMATION: Synthetic Construct

<400> SEQUENCE: 50
ggatcctcgc gagcaccatg tcggccctgc tgatcctggc cctggtcgga gccgccgtcg    60
cccaccacca ccaccaccac gcggctatag gcagctgctc g                       101

<210> SEQ ID NO 51
<211> LENGTH: 34
<212> TYPE: DNA
<213> ORGANISM: Artificial Sequence
<220> FEATURE:
<223> OTHER INFORMATION: Synthetic Construct
```

```
<400> SEQUENCE: 51
ggatccatat gctatctccg gctccggttc gggc                              34

<210> SEQ ID NO 52
<211> LENGTH: 26
<212> TYPE: DNA
<213> ORGANISM: Artificial Sequence
<220> FEATURE:
<223> OTHER INFORMATION: Synthetic Construct

<400> SEQUENCE: 52
cctaggggga cattaaggcg tttaag                                       26

<210> SEQ ID NO 53
<211> LENGTH: 20
<212> TYPE: DNA
<213> ORGANISM: Artificial Sequence
<220> FEATURE:
<223> OTHER INFORMATION: Synthetic Construct

<400> SEQUENCE: 53
gtcctccttg aagtcgatgc                                              20

<210> SEQ ID NO 54
<211> LENGTH: 20
<212> TYPE: DNA
<213> ORGANISM: Artificial Sequence
<220> FEATURE:
<223> OTHER INFORMATION: Synthetic Construct

<400> SEQUENCE: 54
cgacatggtg cagatctaga                                              20

<210> SEQ ID NO 55
<211> LENGTH: 23
<212> TYPE: DNA
<213> ORGANISM: Artificial Sequence
<220> FEATURE:
<223> OTHER INFORMATION: Synthetic Construct

<400> SEQUENCE: 55
ccgtgtttca gttagcctcc ccc                                          23

<210> SEQ ID NO 56
<211> LENGTH: 20
<212> TYPE: DNA
<213> ORGANISM: Artificial Sequence
<220> FEATURE:
<223> OTHER INFORMATION: Synthetic Construct

<400> SEQUENCE: 56
tgctcctgcc gagaaagtat                                              20

<210> SEQ ID NO 57
<211> LENGTH: 24
<212> TYPE: DNA
<213> ORGANISM: Artificial Sequence
<220> FEATURE:
<223> OTHER INFORMATION: Synthetic Construct

<400> SEQUENCE: 57
aagcttccgc cacgaccggt gccg                                         24

<210> SEQ ID NO 58
```

<210> SEQ ID NO 58
<211> LENGTH: 19
<212> TYPE: DNA
<213> ORGANISM: Artificial Sequence
<220> FEATURE:
<223> OTHER INFORMATION: Synthetic Construct

<400> SEQUENCE: 58
ctgttctcga cgcgtcgtc                                                19

<210> SEQ ID NO 59
<211> LENGTH: 18
<212> TYPE: DNA
<213> ORGANISM: Artificial Sequence
<220> FEATURE:
<223> OTHER INFORMATION: Synthetic Construct

<400> SEQUENCE: 59
gaggtgtttc cacgaccc                                                 18

<210> SEQ ID NO 60
<211> LENGTH: 20
<212> TYPE: DNA
<213> ORGANISM: Artificial Sequence
<220> FEATURE:
<223> OTHER INFORMATION: Synthetic Construct

<400> SEQUENCE: 60
gggatgtttg ctccaaccaa                                               20

<210> SEQ ID NO 61
<211> LENGTH: 23
<212> TYPE: DNA
<213> ORGANISM: Artificial Sequence
<220> FEATURE:
<223> OTHER INFORMATION: Synthetic Construct

<400> SEQUENCE: 61
gcgcttttga ctcaaggatt taa                                           23

<210> SEQ ID NO 62
<211> LENGTH: 20
<212> TYPE: DNA
<213> ORGANISM: Artificial Sequence
<220> FEATURE:
<223> OTHER INFORMATION: Synthetic Construct

<400> SEQUENCE: 62
tgcttgtcgg ccatgatata                                               20

<210> SEQ ID NO 63
<211> LENGTH: 20
<212> TYPE: DNA
<213> ORGANISM: Artificial Sequence
<220> FEATURE:
<223> OTHER INFORMATION: Synthetic Construct

<400> SEQUENCE: 63
gaacttcagg gtcagcttgc                                               20

<210> SEQ ID NO 64
<211> LENGTH: 20
<212> TYPE: DNA
<213> ORGANISM: Artificial Sequence
<220> FEATURE:
<223> OTHER INFORMATION: Synthetic Construct

<400> SEQUENCE: 64

```
aacttgtggc cgtttacgtc                                           20
```

```
<210> SEQ ID NO 65
<211> LENGTH: 31
<212> TYPE: DNA
<213> ORGANISM: Artificial Sequence
<220> FEATURE:
<223> OTHER INFORMATION: Synthetic Construct

<400> SEQUENCE: 65
agatctcacc atgaagttgc ctgttaggct g                              31
```

```
<210> SEQ ID NO 66
<211> LENGTH: 48
<212> TYPE: DNA
<213> ORGANISM: Artificial Sequence
<220> FEATURE:
<223> OTHER INFORMATION: Synthetic Construct

<400> SEQUENCE: 66
ccaatctagg accgccgtag aggtttaaca ctcattcctg ttgaagct            48
```

```
<210> SEQ ID NO 67
<211> LENGTH: 78
<212> TYPE: DNA
<213> ORGANISM: Artificial Sequence
<220> FEATURE:
<223> OTHER INFORMATION: Synthetic Construct

<400> SEQUENCE: 67
acctctacgg cggtcctaga ttggtgcgtt aatacacaga attctgattg caccatggca   60
tggaacttca tcatggtc                                             78
```

```
<210> SEQ ID NO 68
<211> LENGTH: 28
<212> TYPE: DNA
<213> ORGANISM: Artificial Sequence
<220> FEATURE:
<223> OTHER INFORMATION: Synthetic Construct

<400> SEQUENCE: 68
catatgctat ttacccggag tccgggag                                  28
```

```
<210> SEQ ID NO 69
<211> LENGTH: 34
<212> TYPE: DNA
<213> ORGANISM: Artificial Sequence
<220> FEATURE:
<223> OTHER INFORMATION: Synthetic Construct

<400> SEQUENCE: 69
ataacttcgt ataatgtatg ctatacgaag ttat                           34
```

```
<210> SEQ ID NO 70
<211> LENGTH: 271
<212> TYPE: DNA
<213> ORGANISM: herpes simplex virus 7

<400> SEQUENCE: 70
gggggaggct aactgaaaca cggaaggaga caataccgga aggaacccgc gctatgacgg    60
caataaaaag acagaataaa acgcacggtg ttgggtcgtt tgttcataaa cgcggggttc   120
ggtcccaggg ctggcactct gtcgataccc caccgagacc ccattggggc caatacgccc   180
```

```
gcgtttcttc cttttcccca ccccaccccc caagttcggg tgaaggccca gggctcgcag    240
ccaacgtcgg ggcggcaggc cctgccatag c                                   271
```

ALPHAVIRAL VECTORS AND CELL LINES FOR PRODUCING RECOMBINANT PROTEINS

CROSS-REFERENCE TO RELATED APPLICATIONS

This application is filed under the provisions of 35 U.S.C. § 371 and claims the priority of International Patent Application No. PCT/ES2014/070416 filed on 20 May 2014 entitled "ALPHAVIRAL VECTORS AND CELL LINES FOR PRODUCING RECOMBINANT PROTEINS" in the name of Alejandro ARANDA, et al., which claims priority to Spanish Patent Application No. P201330722 filed on 20 May 2013, both of which are hereby incorporated by reference herein in their entirety.

FIELD OF THE INVENTION

The present invention is encompassed within the field of vectors for the expression of genes of interest in mammalian cells, specifically in the field of alphaviral vectors. Use of said vectors allows generating cell lines stably expressing a gene of interest.

BACKGROUND OF THE INVENTION

Mammalian cells are the most suitable expression system for obtaining different types of recombinant proteins, particularly those proteins intended for therapeutic applications. Among the most effective expression vectors for incorporating a gene of interest in a cell for the purpose of expressing a protein of interest are alphavirus-based vectors. Alphaviral expression vectors have been developed from different types of alphavirus, including Sindbis virus (SIN), Semliki Forest Virus (SFV) and Venezuelan equine encephalitis (VEE) virus.

The alphavirus replicon contains at its 5' end an open reading frame encoding viral replicase (Rep) which is translated when viral RNA is transfected into eukaryotic cells. Rep is expressed as a polyprotein which is subsequently processed into four subunits (nsps 1 to 4). Unprocessed Rep can copy the RNA vector into negative-strand RNA, a process that only takes place during the first 3 to 4 hours after transfection or infection. Once processed, the Rep will use the negative-strand RNA as a template for synthesizing more replicon molecules. Processed Rep can also recognize an internal sequence in the negative-strand RNA, or subgenomic promoter, from which it will synthesize a subgenomic positive-strand RNA corresponding to the 3' end of the replicon. This subgenomic RNA will be translated to produce the heterologous protein in large amounts.

Normally, alphavirus vectors are based on RNA replicons in which the structural genes have been substituted with a heterologous gene. However, the replication of most alphaviral vectors is cytopathic, so said vectors do not allow obtaining long-lasting expression of the gene of interest. To solve that problem, several groups have identified a series of mutations in alphavirus replicase which can convert these cytopathic viral vectors into non-cytopathic viral vectors, allowing a more long-lasting expression of the recombinant products expressed by the viral vector. These studies have led to the generation of different alphavirus-derived non-cytopathic vectors.

A non-cytopathic mutant isolated from SIN containing a single amino acid change (P for L) in position 726 in nsp2 (SIN P726L vector in nsp2) showed Rep hyperprocessing (Frolov et al., 1999, J. Virol. 73: 3854-65). This mutant was capable of efficiently establishing continuous replication in BHK cells. This non-cytopathic SIN vector has been widely used in vitro as it is capable of providing long-lasting transgene expression with good stability levels and expression levels that were about 4% of those obtained with the original SIN vector (Agapov et al., 1998, Proc. Natl. Acad. Sci. USA. 95: 12989-94). Nevertheless, although said vector is not cytopathic, it lacks the capacity to generate stable cell lines with high expression levels.

With respect to non-cytopathic SFV mutants described by Perri et al. (Perri et al., 2000, J. Virol. 74: 9802-7), including mutants SF2A (mutation L10T in nsp2) and SF2C (mutation L713P in nsp2), as well as double mutant PD (S259P and R650D in nsp2) described by Lundström et al. (Lundström et al., 2001. Histochem. Cell. Biol. 115: 83-91), although they can express similar or even higher protein levels than those of the wild-type virus (PD mutant), these mutants continue to be cytopathic in all cases and the generation of stable cell lines expressing heterologous proteins based on said viral vectors has not been described.

Patent application WO2008065225 describes a non-cytopathic SFV vector as a result of the presence of mutations R649H/P718T in the replicase nsp2 subunit. Said vector allows obtaining cell lines capable of constitutively and stably expressing the gene of interest by means of culturing in the presence of an antibiotic the resistance gene of which is incorporated in the alphaviral vector (Casales et al. 2008. Virology. 376:242-51).

Use of non-cytopathic replicon-based viral vectors is associated with the drawback that mutations can accumulate in the gene of interest because the viral replicase, which lacks error correcting activity, is constantly copying viral RNA. A second drawback of these systems is the fact that they do not allow the expression of toxic proteins for the cell since the expression occurs constitutively. Finally, a decrease in expression levels of the gene of interest is often observed in these systems, which can in part be due to the fact that adaptation of the cells to grow in the presence of the antibiotic, necessary for maintaining expression of the alphaviral replicon, can cause the cells to require a smaller amount of replicon to survive. These problems could theoretically be solved by means of designing a viral vector integrated in the cell genome and in which expression of the alphaviral replicon can be regulable by means of inducible promoters or other systems (WO9738087, WO2000006205 and WO2001081553). However, there is no evidence that such vectors have allowed obtaining high expression of the proteins of interest in a sustainable manner over time. Use of DNA sequences complementary to the RNA sequences making up the alphaviral replicon has allowed designing alphaviral vectors that allow integrating the gene of interest in the cell genome, thereby favoring obtaining a cell line capable of stably expressing the gene of interest without the need to add an antibiotic. However, cell lines obtained by means of these vectors often show great variability as regards expression levels of the proteins of interest, as well as, if appropriate, inducibility of expression of these proteins, probably due to differences in the integration site and the number of integrations in the cell genome, so isolating and selecting those clones with optimal characteristics is necessary.

Therefore there is a need to provide an expression system for expressing genes of interest in mammalian cells which allows stably expressing said genes in large amounts, such that it is suitable for the large-scale production of recombinant proteins.

BRIEF DESCRIPTION OF THE INVENTION

In a first aspect, the invention relates to a nucleotide comprising
- (i) a transcription regulatory sequence,
- (ii) a DNA sequence complementary to an alphavirus replicon which is operatively bound to said transcription regulatory sequence, and wherein said alphavirus replicon complementary sequence comprises a first recognition sequence for a site-specific recombinase located between the alphavirus replicon subgenomic promoter and the alphavirus replicon 3' untranslated sequence,
- (iii) a transcription termination sequence in 3' position with respect to the 3' end of the sequence complementary to an alphavirus replicon, and
- (iv) a second recognition sequence for a site-specific recombinase located in 3' position with respect to the transcription termination sequence.

In a second aspect, the invention relates to an expression vector comprising the polynucleotide of the first aspect.

In a third aspect, the invention relates to a eukaryotic cell comprising the polynucleotide of the first aspect or the expression vector of the second aspect.

In a fourth aspect, the invention relates to a eukaryotic cell comprising the polynucleotide of the first aspect, wherein said polynucleotide is integrated in the genome thereof.

In a fifth aspect, the invention relates to an in vitro method for generating a cell line capable of expressing a gene of interest which comprises
- (i) contacting a cell with a polynucleotide of the first aspect, wherein said polynucleotide additionally comprises said gene of interest operatively bound to the replicon subgenomic promoter, or with an expression vector comprising said polynucleotide, and
- (ii) selecting cells that have incorporated said polynucleotide or an expression vector comprising said polynucleotide.

In a sixth aspect, the invention relates to a vector comprising a DNA sequence comprising, ordered in the 5' to 3' direction,
- (i) a first recognition sequence for a site-specific recombinase,
- (ii) a sequence of a gene of interest,
- (iii) a 3' sequence necessary for the replication of an alphavirus,
- (iv) a transcription termination sequence,
- (v) a sequence of a selection gene operatively bound to a promoter, and
- (vi) a second recognition sequence for a site-specific recombinase.

In a seventh aspect, the invention relates to an in vitro method for generating a cell line capable of expressing a gene of interest comprising the steps of:
- (i) introducing in a cell according to the third or fourth aspect a vector according to the sixth aspect, wherein:
  - (a) said cell comprises a heterologous sequence in 3' position with respect to the replicon subgenomic promoter, wherein said heterologous sequence is a sequence of a gene of interest operatively bound to the subgenomic promoter, or an expression vector comprising said polynucleotide,
  - (b) the first recognition sequence of the polynucleotide comprising the alphavirus replicon complementary sequence is compatible with the first heterospecific recognition sequence of the vector,
  - (c) the second recognition sequence of the polynucleotide comprising the alphavirus replicon complementary sequence is compatible with the second heterospecific recognition sequence of the vector
  - (d) the cell expresses a specific recombinase of said first and second recognition sequences, and
  - (e) the sequence necessary for replication of the alphavirus present in the vector coincides with the sequence necessary for replication of the alphavirus which is part of the alphaviral replicon,
- (ii) maintaining the cell in suitable conditions to allow substitution by means of specific recombination of the gene of interest which is part of the polynucleotide comprising the alphavirus replicon complementary sequence with the gene of interest which is part of the vector according to the sixth aspect, and
- (iii) selecting the cells in which substitution of the first gene of interest with the second gene of interest has occurred.

DETAILED DESCRIPTION OF THE INVENTION

Figure 3:
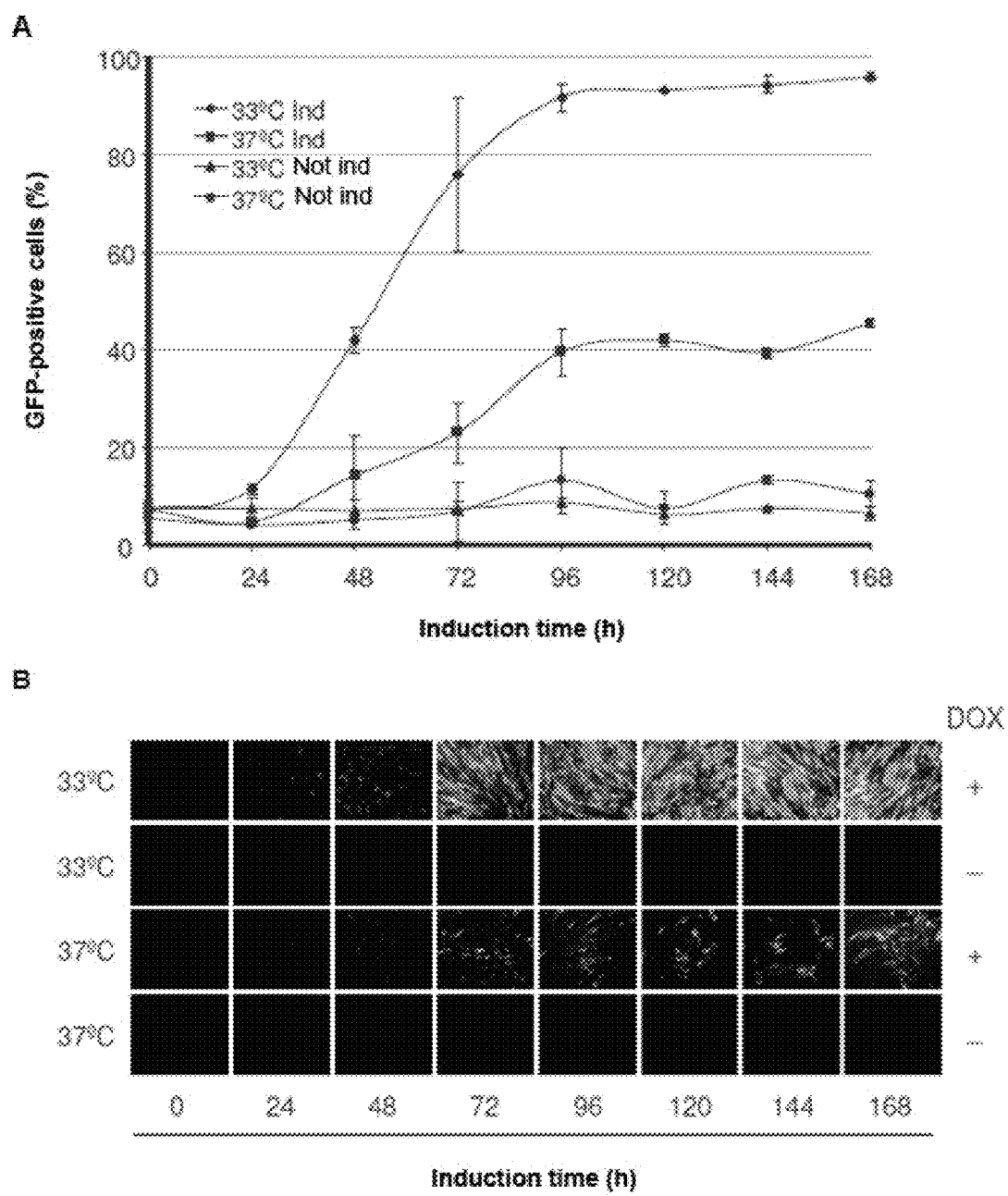
FIG. 3 shows the kinetics of GFP expression in MCL. (A and B). The MCL was incubated with 2 µg/mL of DOX at 33° C. or 37° C., and the presence of positive GFP cells was analyzed at the indicated times by means of FACS (A) and fluorescence microscopy (B) using cells incubated without DOX as a control. (C) The cell lysates were analyzed by means of Western blot with antibodies specific for GFP, replicase and actin. (D) The MCL was plated at a density of $0.5 \times 10^6$ cells per well in 6-well plates. After 24 h, the cells were incubated with DOX at the indicated times and concentrations. After 5 days, the percentage of cells positive for GFP was analyzed by means of FACS. The results shown in A and B are the mean of the values obtained in three independent experiments using passes 3, 5 and 7. The results shown in B and C correspond to cells analyzed in pass 4. Ind., induced; Not ind, Not induced.
Figure 3:
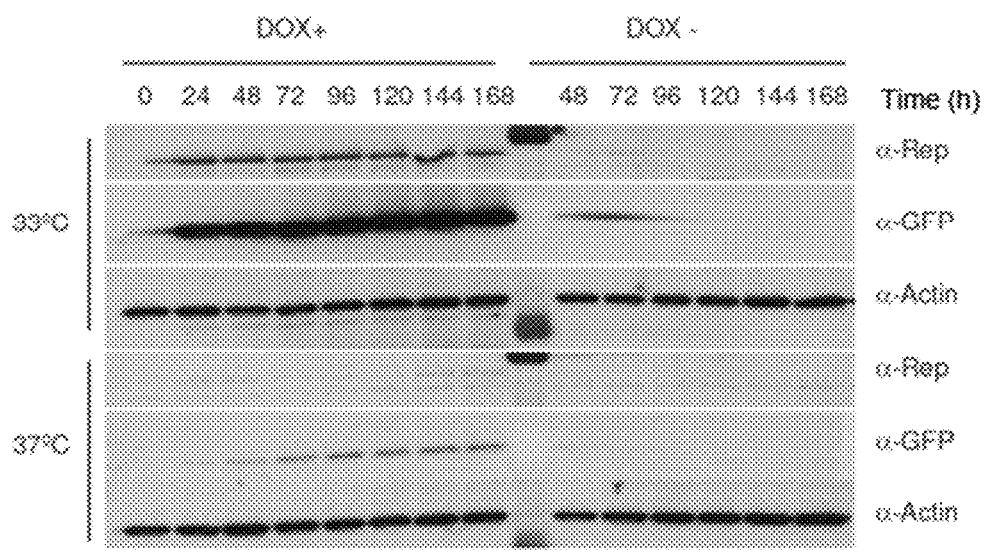
Figure 3:
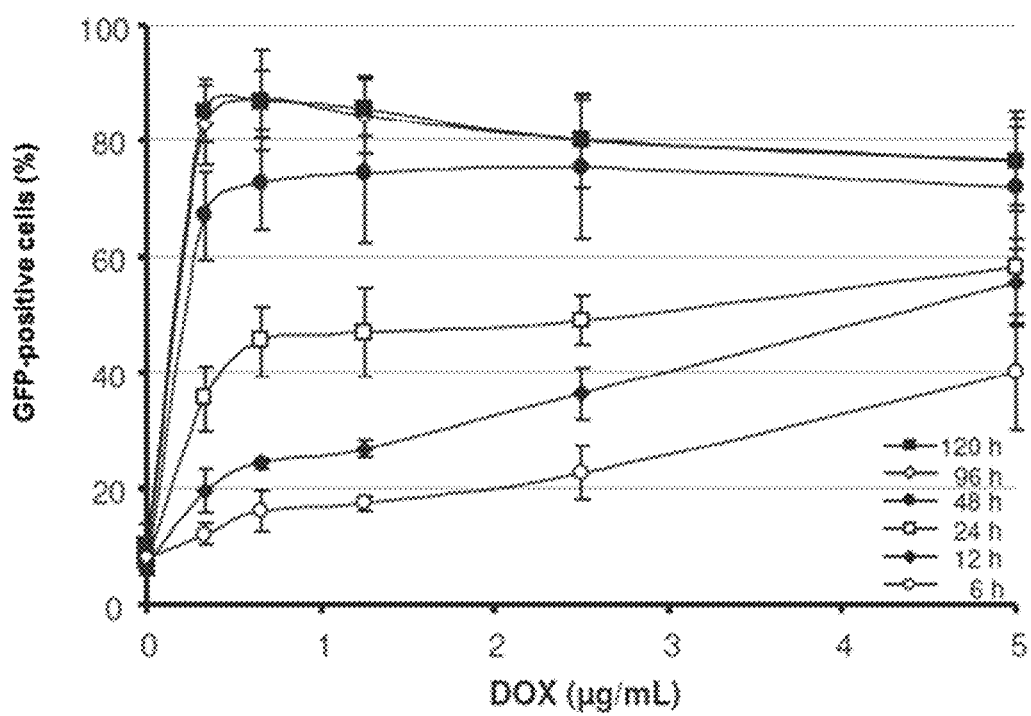
Figure 5:
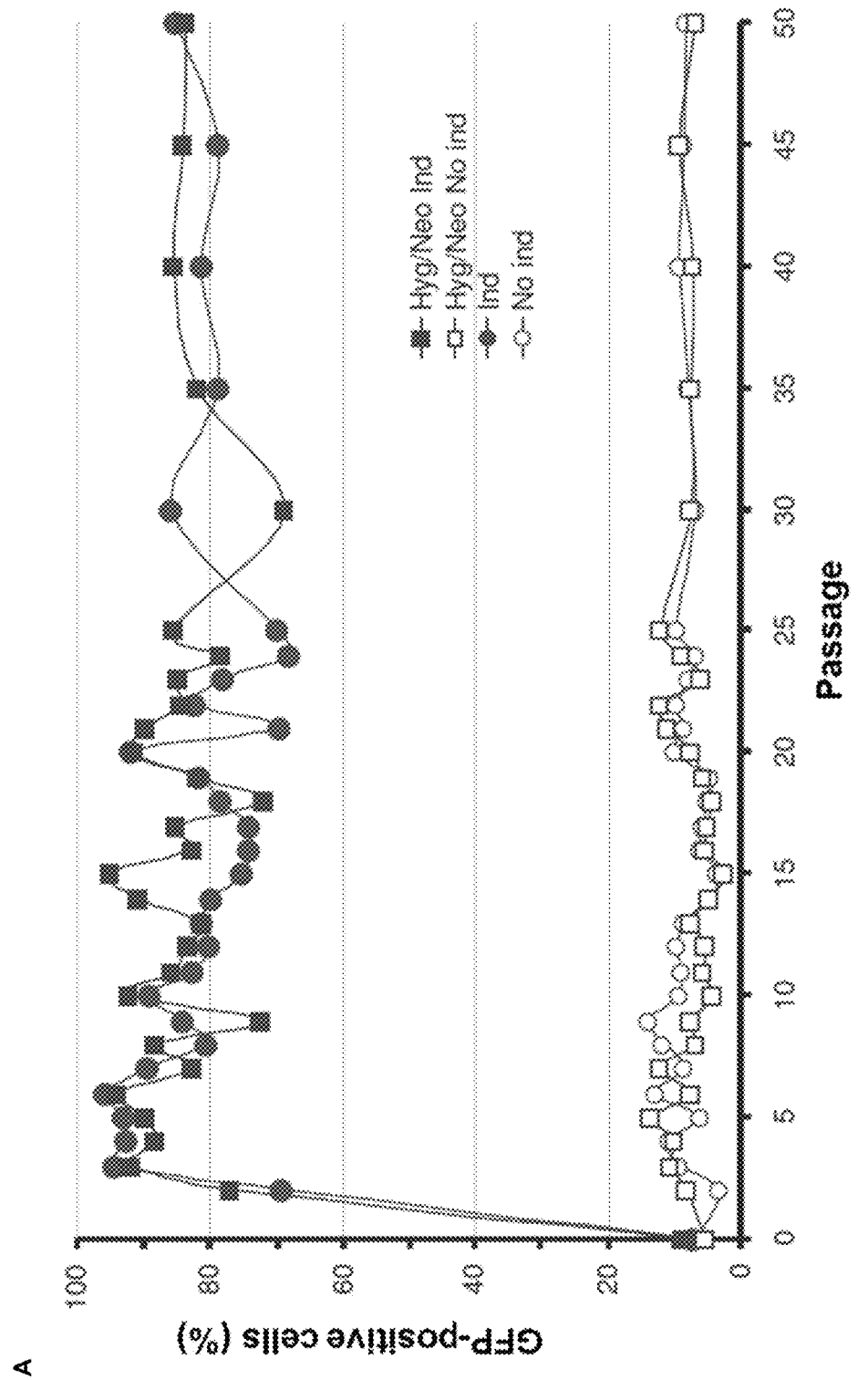
FIG. 5 shows the stability of GFP expression. MCL was passed 50 times every 48 h with or without the selection antibiotics (neomycin and hygromycin). The cells were incubated for 120 h with 1.25 µg/mL DOX (Ind.) or without DOX (Not ind.) at the indicated passes and GFP expression were evaluated by means of FACS (A) and Western blot with a GFP-specific antibody (B). ct, stable line constitutively expressing GFP from the ncSFV-pac2A-GFP RNA vector.
Figure 5:
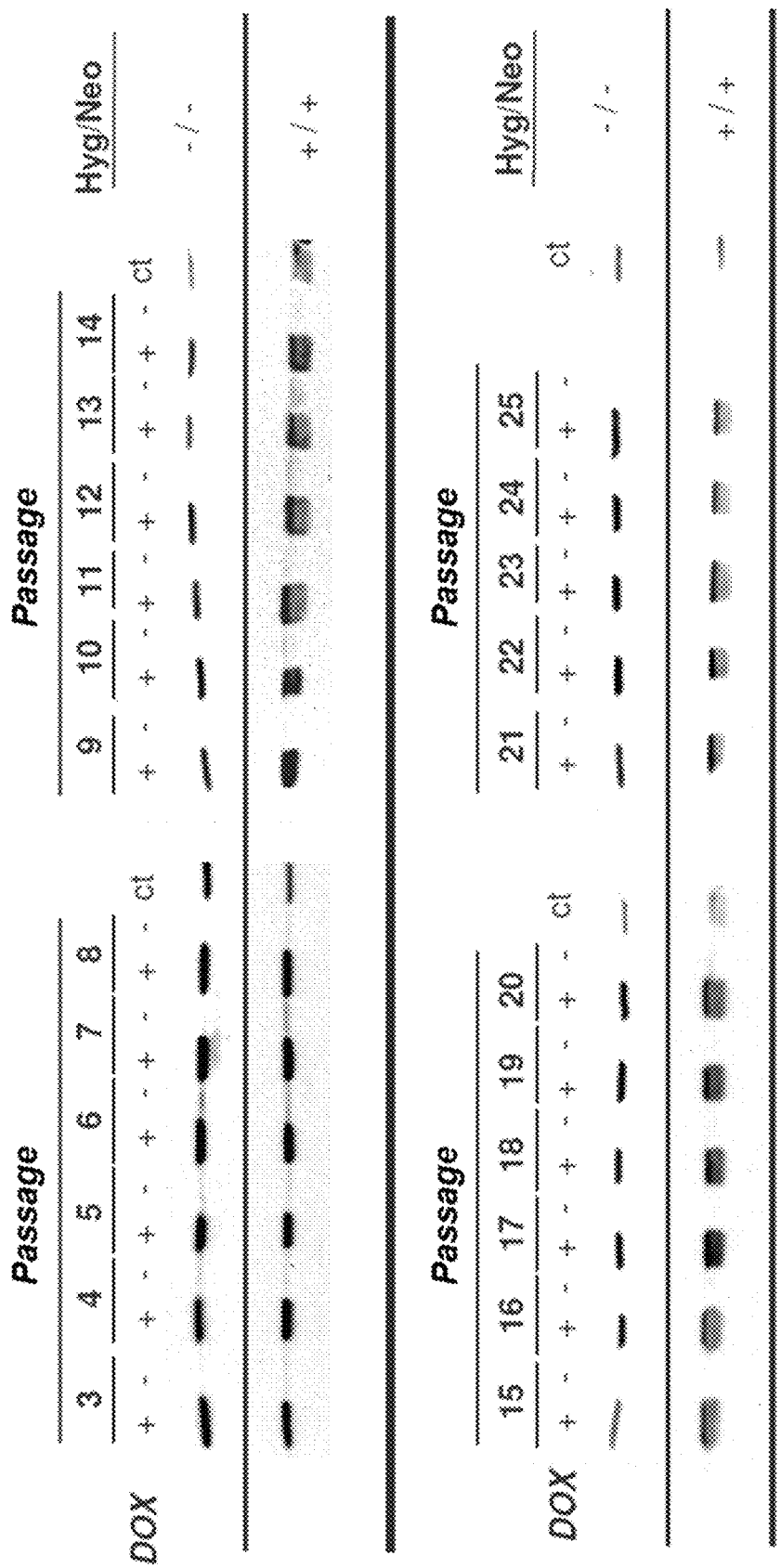

The authors of the present invention have designed a vector comprising a DNA sequence complementary to an alphavirus replicon in which a sequence of a gene of interest has been incorporated along with recognition sequences for site-specific recombination. By means of said vector, it is possible to obtain and select cells in which the alphaviral replicon, including the sequence of the gene of interest, has been integrated in the cell genome, such that the cells stably express the gene of interest (Example 2). Additionally, the authors of the present invention have generated an expression vector such as the one described in which the alphaviral replicon is under the control of an inducible promoter. Said vector has been incorporated to cells which have additionally been modified by means of incorporating an expression cassette encoding a transcriptional activator which, in the presence of a given ligand, is capable of positively regulating the activity of the promoter which regulates alphavirus replicon transcription (Example 1). A cell line which is capable of expressing a gene of interest in an inducible manner has thereby been obtained, thus preventing both mutation accumulation in the gene of interest and the development of resistance to selection antibiotics, which would lead to a decrease in the expression of the gene of interest over time. By means of this expression system, the authors of the present invention have observed that it is possible to obtain cells stably expressing the GFP protein at different induction times (FIG. 3) and throughout successive rounds of amplification (FIG. 5).

Additionally, the presence of recombination sites flanking the sequence of the gene of interest allows, once the alphaviral expression cassette has been incorporated in the cell genome, said gene of interest to be exchangeable with a second gene of interest by means of recombination or RMCE (recombinase-mediated cassette exchange). Therefore, once a cell line optimally expressing a gene of interest is available (i.e., a cell line which, under induction conditions, is capable of stably expressing said gene of interest at high levels), it is not necessary to generate and select new cell lines for the expression of new genes of interest, but rather the transfection of the first cell line with a shuttle vector comprising the sequence of the second gene of interest flanked by the suitable recombination sequences will allow replacing the first gene of interest with the second gene of interest by means of recombination (Examples 4 to 7).

Figure 8:
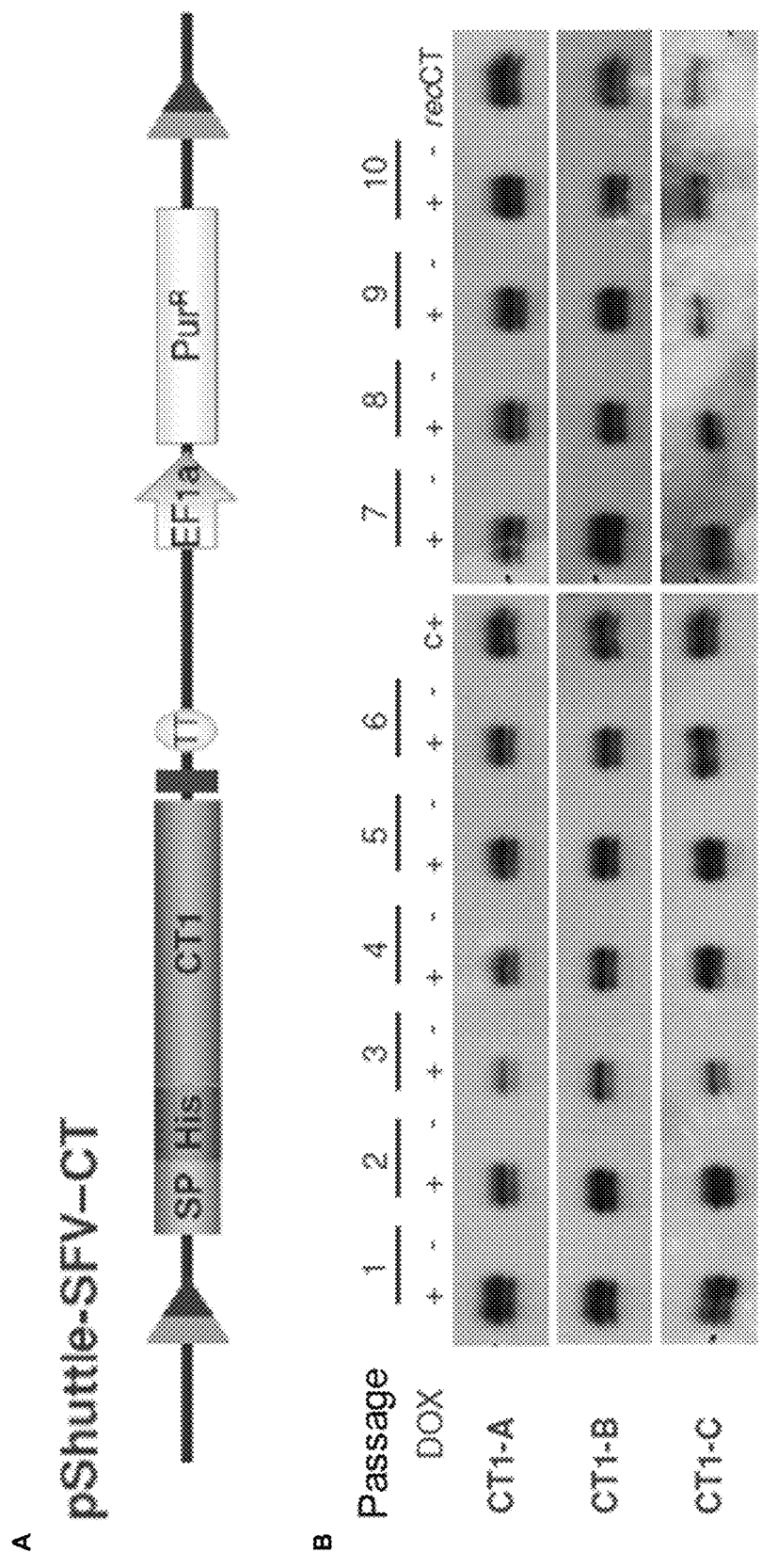
FIG. 8 shows the generation and characterization of stable lines expressing CT-1. (A) Diagram of the pShuttle-SFV vector with the CT-1 sequence (pShuttle-SFV-CT1). In this vector, CT-1 is fused in frame with preprotrypsin signal peptide (SP) and with a sequence encoding a 6-histidine tag at the amino-terminal end (His). (B and C) Analysis of CT-1 expression in three selected clones (CT1-A, CT1-B and CT1-C) obtained after Cre-mediated exchange. The CT-1 clones were passed 10 times in the absence of selection antibiotics, and CT-1 expression in the supernatants collected 120 h after induction with DOX or without induction was analyzed by means of Western blot with an antiserum specific for CT-1 (B) and by means of specific CT-1 ELISA (C). (D) Cytotoxicity after protein expression was tested by means of crystal violet staining at the indicated times. The cytopathic effect was quantified by measuring the staining intensity in each plate with the ImageJ program (Image Processing and Analysis in Java, NIH, USA), considering the intensity in non-induced wells as 100%. recCT, 50 ng of commercial recombinant CT-1 expressed in E. coli.
Figure 8:
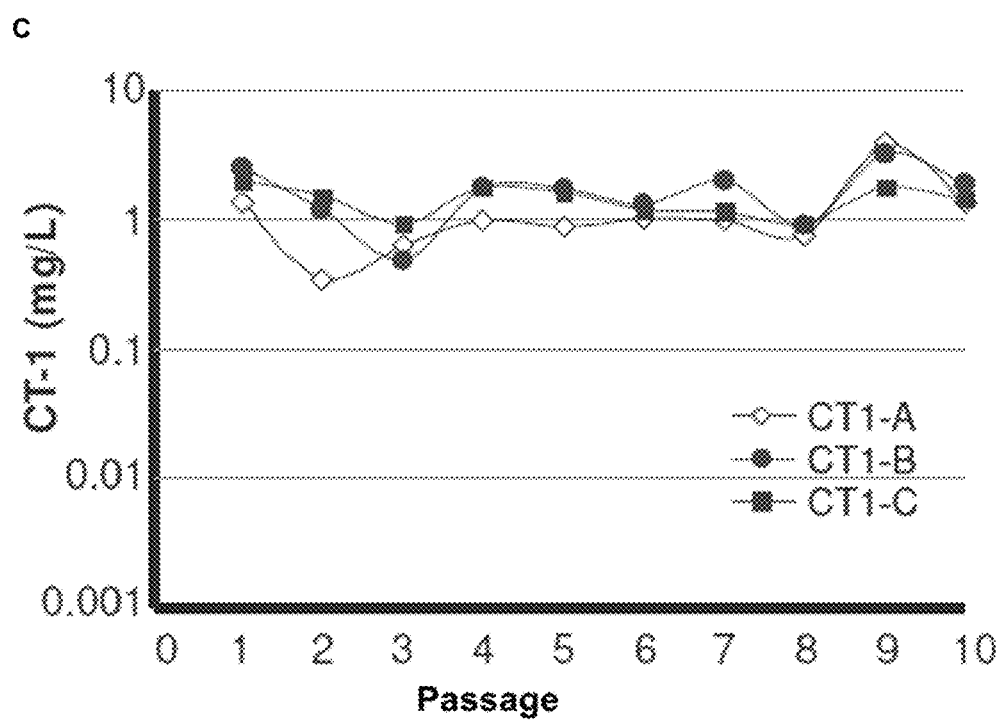
Figure 8:
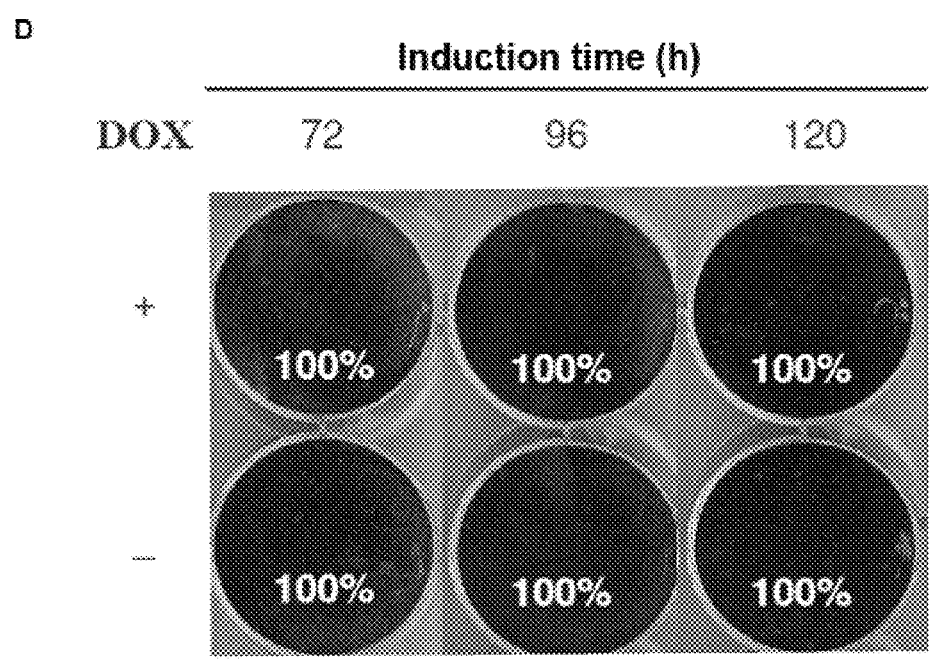
Figure 9:
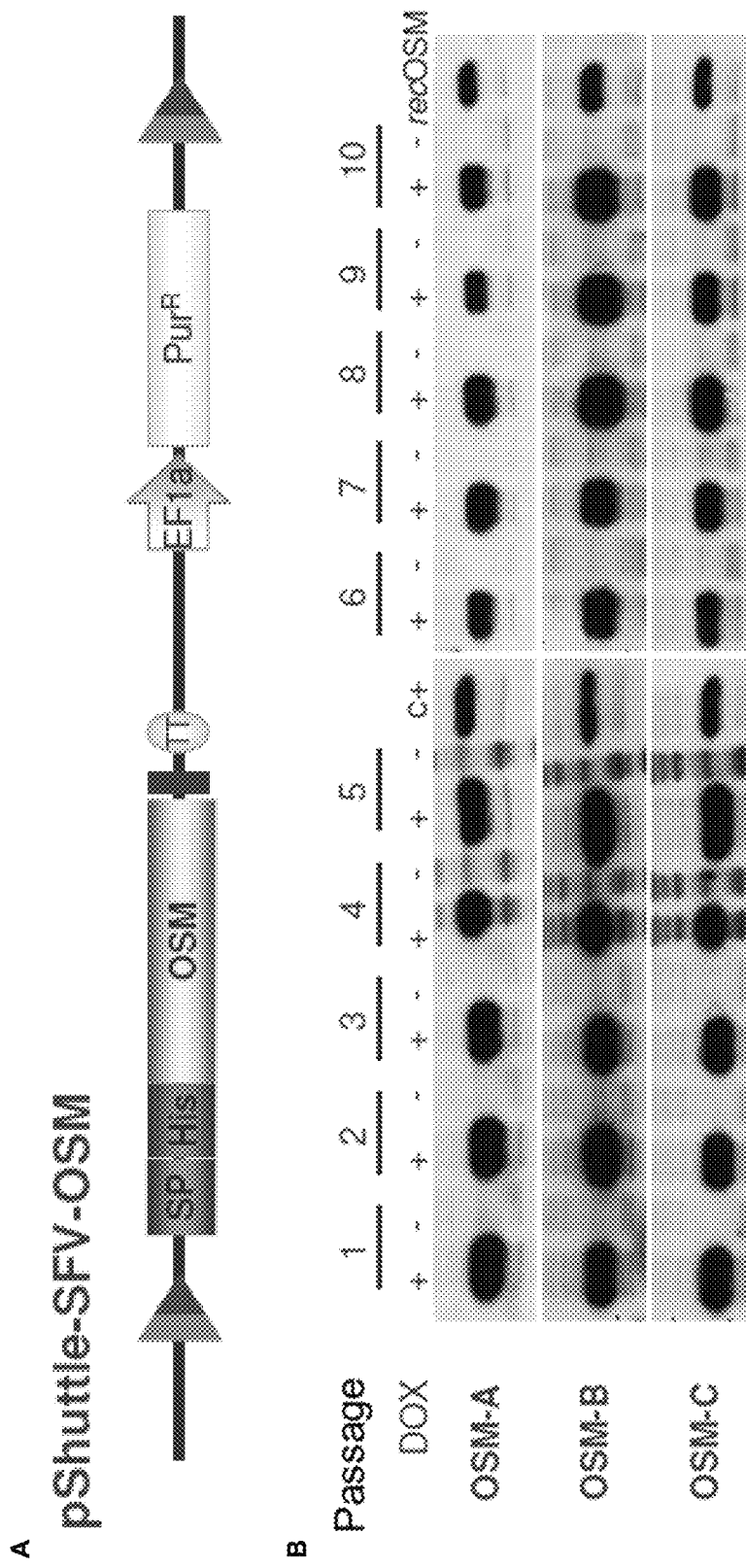
FIG. 9 shows the generation and characterization of stable lines expressing human oncostatin M (OSM). (A) Diagram of the pShuttle-SFV vector with the OSM sequence (pShuttle-SFV-OSM). In this vector, OSM is fused in frame with preprotrypsin signal peptide (SP) and with a sequence encoding a 6-histidine tag at the amino-terminal end (His). (B and C) Analysis of OSM expression in three selected clones (OSM-A, OSM-B and OSM-C), obtained after Cre-mediated exchange. The OSM clones were passed 10 times in the absence of selection antibiotics and OSM expression in the supernatants collected h after induction with DOX or without induction was analyzed by means of Western blot with an antiserum specific for OSM (B) and by means of specific OSM ELISA (C). (D) Cytotoxicity after protein expression was tested by means of crystal violet staining at the indicated times and was quantified as described in FIG. 8D. recOSM, 50 ng of commercial recombinant OSM expressed in E. coli.
Figure 9:
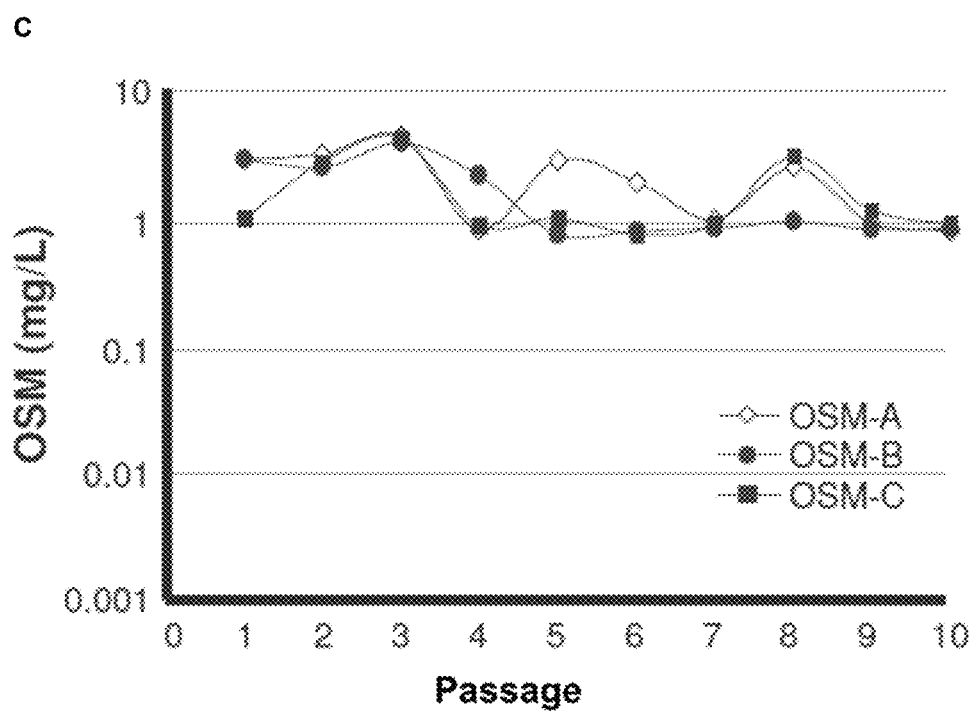
Figure 9:
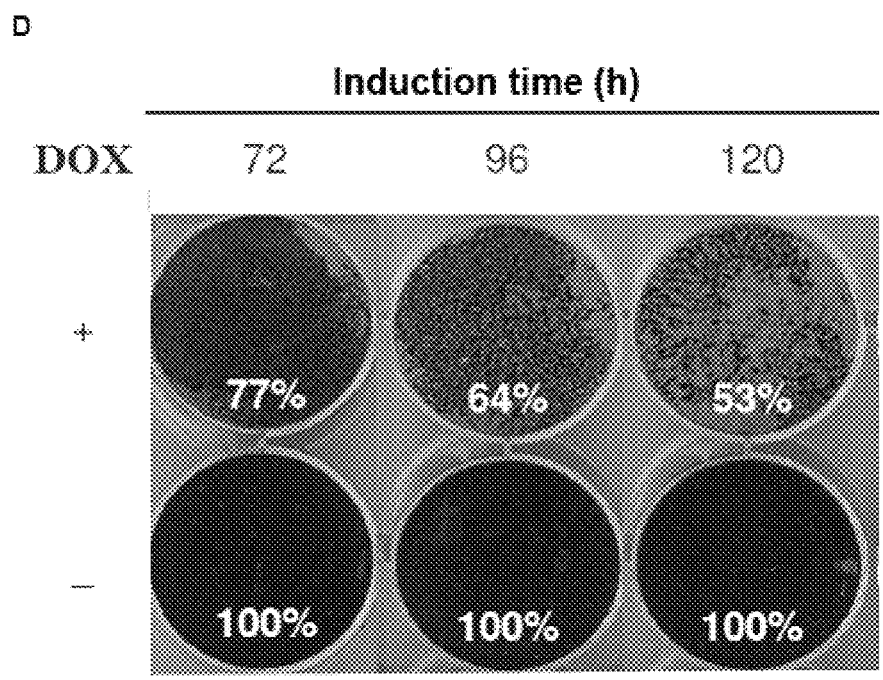
Figure 12:
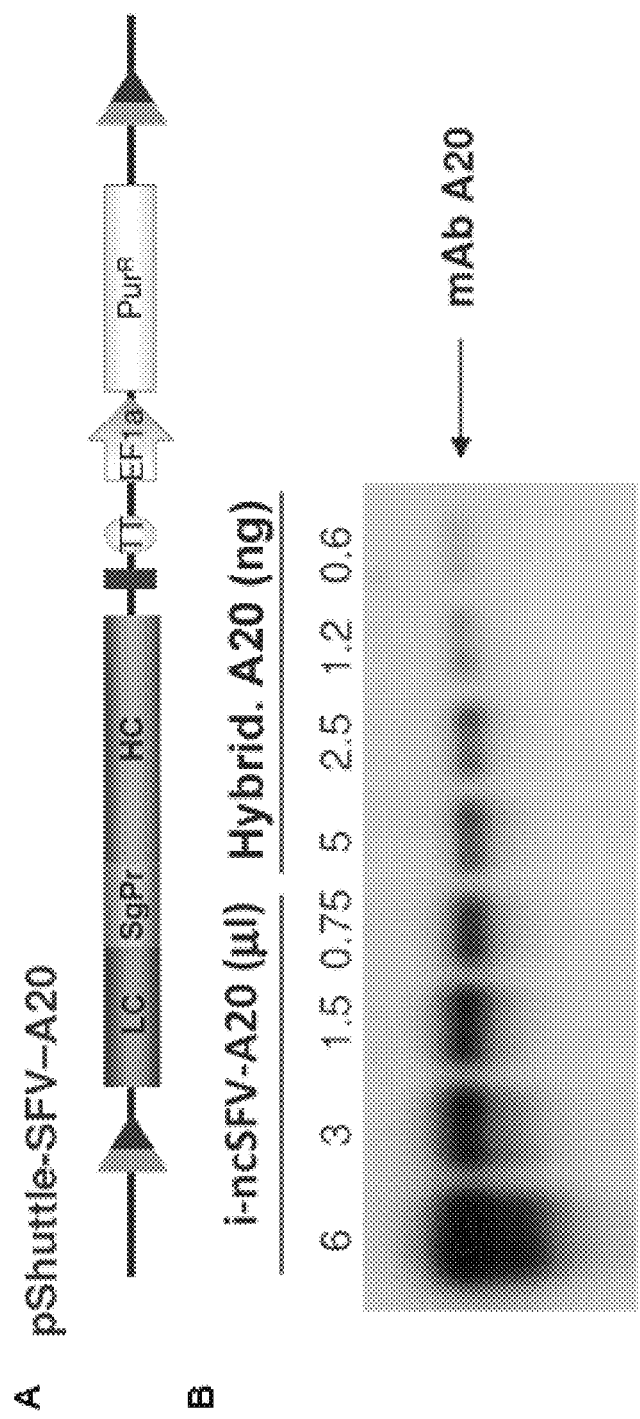
FIG. 12 shows the expression of a monoclonal antibody (mAb) in inducible cell lines. (A) Diagram of the pShuttle-SFV vector with the mAb A20 sequence (pShuttle-SFV-A20). (B) Analysis of mAb A20 expression after inducing with DOX. The bands obtained by Western blot (samples loaded without DTT) were analyzed by densitometry and quantified using the bands generated from mAb A20 purified from a hybridoma (hybrid A20) to generate a standard curve. SgPr, SFV subgenomic promoter; LC, A20 light chain; HC, A20 heavy chain.

Following this methodology, the authors of the present invention have generated a BHK cell line into which genome an alphaviral expression cassette has been integrated, comprising the GFP gene sequence under the control of a promoter inducible by doxycycline and flanked by LoxP recombination sites. From this cell line referred to as master cell line or MCL, derivative lines stably expressing human cardiotrophin-1 proteins (FIGS. 8B and 8C), human oncostatin M proteins (FIGS. 9B and 9C) or A20 idiotypic antibody light and heavy chains (FIG. 12B) have been obtained by means of transfecting the MCL line with shuttle vectors including the sequences of each of these genes (FIGS. 8A, 9A and 12A, respectively).

The following inventive aspects have been developed based on these discoveries.

Polynucleotide of the Invention

In a first aspect, the invention relates to a polynucleotide, hereinafter polynucleotide of the invention, comprising
  (i) a transcription regulatory sequence,
  (ii) a DNA sequence complementary to an alphavirus replicon, wherein said sequence is operatively bound to said transcription regulatory sequence, and wherein the alphavirus replicon complementary sequence comprises a first recognition sequence for a site-specific recombinase located between the alphavirus replicon subgenomic promoter and the untranslated alphavirus replicon 3' sequence,
  (iii) a transcription termination sequence in 3' position with respect to the 3' end of the sequence complementary to an alphavirus replicon, and
  (iv) a second recognition sequence for a site-specific recombinase located in 3' position with respect to the transcription termination sequence.

As it is used herein, the term "polynucleotide" refers to a single-stranded or double-stranded polymer having deoxyribonucleotide or ribonucleotide bases.

Transcription Regulatory Sequence

The first element of the polynucleotide of the invention comprises a transcription regulatory sequence.

As it is used herein, the term "transcription regulatory sequence" refers to a nucleic acid sequence regulating the transcription of one or more polynucleotides that are downstream of said transcription regulatory sequence. The transcription regulatory sequence comprises a promoter and can optionally comprise regulatory elements such as inducing agent responsive elements or enhancing elements or "enhancer".

As it is used herein, the term "promoter" refers to a nucleic acid sequence which is structurally characterized by the presence of a binding site for the DNA-dependent RNA polymerase, transcription start sites and any other DNA sequence including, but without being limited to, transcription factor binding sites, repressor and activator protein binding sites and any other nucleotide sequence known in the state of the art capable of directly or indirectly regulating transcription from a promoter.

As it is used herein, the term "operatively bound" refers to the functional relationship of a sequence with a promoter sequence. Therefore, a sequence is operatively bound to a promoter if said promoter affects the transcription of said sequence. Generally, the sequence of a gene is contiguous to the sequence of the promoter to which it is operatively bound. In the polynucleotide of the invention, the DNA sequence complementary to an alphavirus replicon is operatively bound to a promoter, i.e., said promoter regulates transcription of the DNA sequence complementary to the alphavirus replicon.

The "transcription regulatory sequence" which is part of the polynucleotide of the invention and is operatively bound to the DNA sequence complementary to an alphavirus replicon can have constitutive activity or regulable activity.

As it is used herein, the term "transcription regulatory sequence having constitutive activity" or "constitutive promoter" refers to a regulatory sequence or a promoter the activity of which is kept at a relatively constant level in all the cells of an organism or during most stages of development, with little or no consideration to the surrounding conditions of the cell.

As it is used herein, the term "transcription regulatory sequence having regulable activity" or "regulable promoter" refers to any DNA sequence which is capable of promoting the transcription of a polynucleotide located in the 3' position in the presence of a compound or certain conditions. Regulable promoters which can be used in the context of the polynucleotide of the invention are preferably those which respond to an inducing agent, show absent or insignificant baseline expression in the absence of said inducing agent, and are capable of promoting activation of the transcription of the sequence located in 3' position, i.e., the DNA sequence complementary to the alphavirus replicon. Depending on the type of inducing agent, the inducible promoters are classified as on/off Tet promoters (Gossen, M. and H. Bujard, 1992, Proc Natl Acad Sci, 89: 5547-5551; Gossen, M. et al., 1995, Science 268: 1766-1769); Rossi, F. M. V. and Blau H. M., 1998, Curr Opin Biotechnol 9: 451-456); ON/OFF PIP promoters (U.S. Pat. No. 6,287,813); antiprogestin-dependent promoters (US2004132086), ecdysone-dependent promoters (Christopherson et al., 1992, Proc Natl Acad Sci, 89: 6314-6318; No et al., 1996, Proc Natl Acad Sci, 93: 3346-3351, Suhr et al., 1998, Proc. Natl. Acad. Sci., 95: 7999-8004 and WO9738117), metallothionein-dependent promoters (WO8604920) and rapamycin-dependent promoters (Rivera et al., 1996, Nat. Med. 2:1028-32).

An "inducible activity transcription regulatory sequence" or "inducible promoter" is a sequence or promoter which is regulated physiologically or in relation to development, for example by means of applying a chemical inducer.

In one embodiment, the transcription regulatory sequence comprises a tissue-specific promoter, preferably a liver-specific promoter. A "tissue-specific" promoter is a promoter active only in specific types of tissues or cells, i.e., a promoter which is more active in one or more (for example two, three or four) particular tissues than in other tissues (i.e., it is capable of taking expression of a coding sequence to which it is operatively bound to higher levels in the tissue(s) for which the promoter is specific compared with any other). Typically, the gene located in 3' position of a "tissue-specific" promoter is a gene which is active at a much higher level in tissue(s) for which said promoter is specific than in any other tissue. In this case, there may be little or substantially no promoter activity in another tissue different from that for which the promoter is specific.

In the context of this invention, a "liver-specific promoter" is a promoter which is more active in liver compared with its activity in any other tissue of the body. Typically, the activity of a liver-specific promoter will be considerably greater in liver than in other tissues. For example, such promoter can be at least 2, at least 3, at least 4, at least 5 or at least 10 times more active (determined, for example, by means of the capacity thereof to direct the expression in a given tissue while at the same time prevent expression in other cells or tissues. Therefore, a liver-specific promoter allows active expression of the bound gene in the liver and prevents expression in other cells or tissues.

Suitable liver-specific promoters include, without limitation, an al-anti-trypsin promoter (AAT), a thyroid hormone binding globulin promoter, an alpha fetoprotein promoter, an alcohol dehydrogenase promoter, an IGF-II promoter, factor VIII promoter (FVIII), an HBV basic core promoter (BCP) and PreS2 promoter, an albumin promoter, a thyroxine-binding globulin promoter (TBG), an (HCR)-ApoCII hepatic control region hybrid promoter, an HCR-hAAT hybrid promoter, an AAT promoter combined with mouse albumin gene enhancing element (Ealb), an apolipoprotein E promoter, a low-density lipoprotein promoter, a pyruvate kinase promoter, a phosphoenolpyruvate carboxykinase promoter, a lecithin-cholesterol acyltransferase promoter (LCAT), an apolipoprotein H promoter (ApoH), transferrin promoter, a transthyretin promoter, alpha-fibrinogen and beta-fibrinogen promoters, an alpha 1-antichymotrypsin promoter, an alpha-2-HS glycoprotein promoter, a haptoglobin promoter, a ceruloplasmin promoter, a plasminogen promoter, complement protein promoters (CIq, CIr, C2, C3, C4, C5, C6, C8, C9, factor I and factor H of the complement), complement C3 activator and α1-acid glycoprotein promoter. Additional tissue-specific promoters can be found in Tissue-Specific Promoter Database, TiProD (Nucleic Acids Research, J4:D104-D107 (2006).

In a particular embodiment, the liver-specific promoter is the albumin gene promoter described by Kramer et al. (2003. Mol. Ther. 7, 375-85) or a functionally equivalent variant thereof. "Functionally equivalent variant of the albumin gene promoter" is understood as any promoter having minimal sequence identity with the albumin gene promoter, for example, a sequence identity of at least 60%, preferably at least 70%, more preferably at least 80%, even more preferably at least 90%; still more preferably at least 99%, and is capable of carrying out the same function as said promoter, i.e., it is capable of promoting the transcription of the albumin gene when the sequence of said gene is operatively bound to said promoter.

In a preferred embodiment, the liver-specific promoter is an inducible liver-specific promoter, for example, a liver-specific promoter inducible by tetracycline such as the promoter described by Wang et al. (Nature Biotech., 1997; 15:239-43), the liver-specific promoter inducible by mifepristone (RU-486) described by Burcin et al., (Proc. Natl. Acad. Sci. USA, 1999, 96:355-60), the tetracycline-regulable liver-specific promoter described by Manickan et al. (J. Biol. Chem., 2001, 276:13989-13994), the promoters described by Han et al. (Molecular Therapy, 2005, 11, S161), the tetracycline-regulated adenovirus expression system for in vivo distribution to the liver described by Tietge et al. (J. Gene. Medicine, 2003, 5:567-575), the liver-specific promoter inducible by mifepristone described by Crettaz et al. (Molecular Therapy (2006) 13, S224) and the like.

In a preferred embodiment, the transcription regulatory sequence which is operatively bound to the DNA sequence complementary to the alphavirus replicon has regulable activity.

In a particular embodiment, the transcription regulatory sequence additionally comprises an inducing agent responsive element.

The term "inducing agent responsive element" refers to one or more DNA elements acting in cis and conferring a promoter the capacity of activating transcription in response to the interaction of said element with the DNA binding domains of a transcription factor or transactivator, the transcriptional activity of which is induced in the presence of the inducing agent, normally as a result of a conformational change in the transactivator resulting from binding to the inducing agent. The expression "inducing agent responsive element" must therefore be understood as a transcriptional activator responsive element in the presence of an inducing agent. The DNA binding domain of the transcription factor or the transactivator is capable of binding, in the presence or absence of the activating agent, to the DNA sequence of the responsive element to start or inhibit transcription of genes located in 3' position with respect to the promoter. The term "responsive element" is used interchangeably with "transcriptional responsive element" or TRE.

In a preferred embodiment, the inducing agent responsive element is a ligand responsive element. In an even more preferred embodiment, the ligand responsive element is a transactivator responsive element that can be activated by antibiotics, preferably a tetracycline or tetracycline analogue responsive element, and even more preferably a tetracycline or tetracycline analogue responsive element comprising a variable number of copies of the operator sequence having 42 base pairs (referred to as TetO) as originally described in Baron et al. (Nucleic Acids Res., 1995, 17:3605-3606). The number of copies of TetO can be at least 2, at least 5 or preferably not more than 7. Such tetracycline responsive elements can activate bidirectional transcription in the presence of the tetracycline-activated reverse transactivator (or the doxycycline analogue thereof) as originally described by Gossen et al. (Science, 1995, 278:1766-1769). In a preferred embodiment, the transactivator+tetracycline responsive element comprises 7 copies of the operator sequence; in which case it is referred to as TetO7. In an even more preferred embodiment, the transcription regulatory sequence formed by the promoter-operator assembly comprises or consists of the sequence SEQ ID NO: 4.

In a preferred embodiment, the regulable promoter must be placed in a position such that transcription starts in the first nucleotide of the DNA sequence complementary to the alphavirus replicon. In a particular embodiment, the regulable promoter is the minimal albumin promoter comprising the tetracycline responsive element TetO7 described by Zabala et al. (Zabala et al., 2004, Cancer Research, 64: 2799-2804) and the sequence of which is shown in SEQ ID NO: 4. In a preferred embodiment, for the transcription to start in the first nucleotide of the DNA sequence complementary to the alphavirus replicon, the promoter does not comprise the last 22 nucleotides of SEQ ID NO: 4. In a particular embodiment, the promoter comprises a sequence equal to the first 467 nucleotides of SEQ ID NO: 4, i.e., the promoter comprises the sequence SEQ ID NO: 5. In another particular embodiment, the promoter comprises the sequence SEQ ID NO: 6. In another particular embodiment, the promoter comprises the sequence SEQ ID NO: 7. In another particular embodiment, the promoter comprises the sequence SEQ ID NO: 8. In a preferred embodiment, the promoter comprises the sequence SEQ ID NO: 8 but does not comprise the sequence SEQ ID NO: 4. In a preferred embodiment, the promoter consists of the sequence SEQ ID NO: 8.

DNA Sequence Complementary to an Alphavirus Replicon Comprising a First Recognition Sequence for a Site-Specific Recombinase The second element of the polynucleotide of the invention comprises a DNA sequence complementary to an alphavirus replicon which is operatively bound to said transcription regulatory sequence.

As it is used herein, the term "DNA sequence complementary to an alphavirus replicon" refers to a DNA sequence which is complementary to an alphavirus replicon RNA sequence.

As it is used herein, the term "alphavirus replicon" refers to an RNA polynucleotide expressing structural and non-structural proteins of the alphavirus from which it is derived which allow said RNA to direct its own replication when being introduced in a receiving cell. Typically, the alphavirus replicon comprises the following elements, ordered from the 5' to 3' end:
- a 5' sequence capable of directing replication of the alphavirus,
- a nucleotide sequence encoding a polyprotein comprising the sequences of non-structural proteins nsp1, nsp2, nsp3 and nsp4 of an alphavirus, referred to as non-structural polyprotein,
- an alphavirus subgenomic promoter,
- a 3' sequence necessary for replication of the alphavirus, including a polyadenine sequence.

As it is used herein, the term "alphavirus" refers to any RNA virus of the genus alphaviridae. A description of the members of the genus alphaviridae can be found in Strauss and Strauss, Microbiol. Rev., 58:491-562 (1994). Examples of alphavirus include, without limitation, Aura virus, Bebaru virus, Cabassou virus, Chikungunya virus, eastern equine encephalomyelitis virus, Fort Morgan virus, Getah virus, Kyzylagach virus, Mayaro virus, Middleburg virus, Mucambo virus, Ndumu virus, Pixuna virus, Tonate virus, Triniti virus, western equine encephalomyelitis virus, Whataroa virus, Sindbis (SIN) virus, Semliki Forest Virus or SFV, Venezuelan equine encephalomyelitis (VEE) virus and Ross river virus. The gene sequences of different alphavirus as well as the sequences of different structural and non-structural proteins, are known in the state of the art, such as sequences of the SIN virus (GenBank Accession Nos. J02363, NCBI Accession No. NC_001547), SFV virus (GenBank Accession No. X04129, NCBI Accession No. NC_003215), VEE virus (GenBank Accession No. L04653, NCBI Accession No. NC_001449), etc.

As it is used herein, the 5' sequence capable of directing replication of the alphavirus, also referred to as "5' untranslated sequence" or "5'-UTR", refers to the sequence at the 5' end of the alphavirus genome which is not translated and which contains the region necessary for replication of the alphavirus, i.e., the sequence which is recognized by the polymerase during synthesis of the RNA molecule from the RNA template having a negative polarity. In a preferred embodiment, the 5' untranslated sequence comprises the sequence defined by SEQ ID NO: 1.

As it is used herein, the term "sequence encoding the non-structural polyprotein" or "sequence encoding replicase Rep" refers to a sequence encoding the non-structural protein replicase or Rep, capable of directing replication of alphaviral RNA. Said non-structural protein is an nsP1-4 polyprecursor, i.e., a protein which is subsequently processed to give rise to four independent proteins: nsP1, nsP2, nsP3 and nsP4. In a preferred embodiment, the sequence encoding the non-structural polyprotein originates from the SFV. Briefly, the alphavirus genome comprises sequences encoding non-structural proteins (nsPs), sequences encoding structural proteins (for example, the capsid, envelope proteins, etc), as well as regulatory sequences necessary for replication and packaging. The RNA genome of an alphavirus comprises a gene encoding a replicase Rep which is translated inside a eukaryotic cell to give rise to a polyprotein that is subsequently processed into four subunits (nsp 1 to 4). The unprocessed replicase Rep is capable of copying the alphaviral RNA genome into negative-strand RNA, from which the already processed replicase synthesizes more replicon molecules. Likewise, the processed Rep is capable of recognizing an internal sequence in the viral RNA, referred to as subgenomic promoter, from which subgenomic positive-strand RNA is synthesized and translated to give rise to the structural proteins of the alphavirus.

The nsp1 protein is involved in the initiation (or continuation) of the synthesis of the negative strand of the viral RNA and in the addition of the cap to the 5' end of the genomic and subgenomic RNA during transcription since nsp1 has methyltransferase and guanyltransferase activity. nsp1 also modulates the activity of nsp2 since polyproteins containing nsp1 do not effectively process binding between nsp2 and nsp3.

nsp2 is a multifunctional protein involved in viral genome replication and in polystructural polyprotein processing. The N-terminal end of nsp2 has helicase activity. Likewise, subgenomic RNA synthesis seems to require the activity of nsp2. The C-terminal domain of nsp2 is capable of proteolytically processing in trans and in cis the structural polyprotein in nsp1/nsp2, nsp2/nsp3, and nsp3/nsp4 binding zones.

nsp3 is a protein with two clearly differentiated domains and the function of which in viral replication is not completely established although it is known that nsp3 is required for viral RNA synthesis.

nsp4 is the RNA polymerase containing the GDD amino acid motif characteristic of this enzyme. The nsP4 polypeptide sequence has a similar length among different alphavirus (607 amino acids in VEE, 610 amino acids in SIN and 614 amino acids in SFV), showing a high degree of conservation between them (Kinney, et al., 1989, Virology, 170:19-30).

In a preferred embodiment, the sequence encoding the non-structural polyprotein belongs to SFV. In an even more preferred embodiment, said sequence comprises the sequence depicted in SEQ ID NO: 2.

As it is used herein, the term "alphavirus subgenomic promoter" or "26S promoter" refers to a promoter originally defined in an alphaviral genome which is capable of directing, along with viral and cell polymerases, transcription of a subgenomic mRNA having a length less than that of the viral genome during the alphaviral genome replication process. In the alphavirus, the subgenomic promoter originates from the region of the genome which is between the coding regions of the non-structural and structural proteins of said alphavirus. Typically, the subgenomic promoter comprises a core or central region providing most of the promoter activity and flanking regions (native or extended promoter), increasing transcription activating capacity. In the case of SFV virus (SFV4 strain), the subgenomic promoter is comprised between positions 7348 and 7378, whereas the minimum region necessary for transcription corresponds to nucleotides 7354-7378 (Rausalu K. et al., 2009 Virol J. 6: 33).

The subgenomic promoter can be truncated (to produce a minimal subgenomic promoter, for example) or modified such that the activity thereof is reduced or increased using methods known in the art. In a particular embodiment, the alphaviral subgenomic promoter originates from SFV.

As it is used herein, the term "3' sequence necessary for replication of the alphavirus" also referred to as "3' untranslated sequence" or "3'-UTR" corresponds to an untranslated region which appears after the end codon. The 3' untranslated region of the polynucleotide of the invention typically contains an RNA polymerase recognition sequence. This sequence, referred to as alphavirus polymerase recognition sequence, 3' terminal CSE or 3' replication sequence (see Strauss and Strauss, 1994, supra), provides a recognition site for the origin of replication in the negative strand. The exact sequence which is used as the recognition sequence as well as the extension thereof are not particularly limiting provided that they maintain the capacity to function as a recognition sequence. The 3' untranslated region typically contains a polyadenine tag which allows increasing RNA stability, and therefore the amount of products resulting from the translation of said RNA. The poly(A) tag can be of any size provided that it is sufficient to increase stability in the cytoplasm of the molecule of the vector of the invention. The poly(A) tag comprises at least 10 adenosine nucleotides and more preferably at least 25 or 40 adenosine nucleotides. In a preferred embodiment, the 3' untranslated region originates from SFV. In an even more preferred embodiment, the 3' untranslated region comprises the sequence indicated in SEQ ID NO: 3.

The DNA sequence complementary to an alphavirus replicon comprises a recognition sequence for a site-specific recombinase (hereinafter, first recognition sequence for a site-specific recombinase) wherein said sequence is located between the alphavirus subgenomic promoter and the alphavirus replicon 3' untranslated sequence.

As it is used herein, the term "site-specific recombinase" refers to a protein which is capable of promoting site-specific recombination between target sites for said recombinases. Suitable recombinases for use in the invention include phage P1 Cre recombinase (specific for the LoxP sequence), S. cerevisiae FLP recombinase (specific for the FRT sequence), Streptomyces ΦC31 phage integrase (specific for attB, attP sequences), TP901-1 recombinase, R4 recombinase or lambda integrase.

"Recognition sequences for a site-specific recombinase" must be chosen based on the recombinase that will be used when the cells are co-transfected for selecting and generating the stable cell line. Therefore, if the recombinase is Cre recombinase, the recognition sequences must be LoxP sites. If the recombinase is FLP recombinase, the recognition sequences must be FRT sites.

In a preferred embodiment, the recognition sequences for a site-specific recombinase are LoxP sequences specific for Cre recombinase.

As it is used herein, the term "Cre recombinase" includes both phage P1 Cre recombinase as originally described by Abreinski and Hoess (Abreinski and Hoess, 1984, J. Biol. Chem. 259: 1509-1514), and fusion proteins comprising the recombinase sequence and a second recombinase activity-regulating polypeptide. The Cre recombinase, whether used as such or in the form of a fusion protein, can be modified so that it has greater specificity with respect to the target sequences as described in WO2000060091.

As it is use herein, the term "LoxP sequence" refers to a 34 base pair sequence which is in turn formed by two inverted 13 base pair repetitions flanking an 8 base pair central region. The invention also contemplates the use of wild-type LoxP sequence variants which are incapable of undergoing recombination with the LoxP sequences, but which can only recombine with identical LoxP variants, such as those described in WO9925851 and WO2007085906. LoxP sequence variants useful in the context of the invention include LoxP sequences loxP2, loxP511 (described in WO2007085906), loxP514, loxB, loxC2, LOXL, loxR, loxA86, loxA117, loxP3 and loxP23.

In a particular embodiment, the alphavirus replicon is a replicon of the Semliki Forest Virus or SFV. The alphavirus replicon is preferably a non-cytopathic replicon. In an even more preferred embodiment, the SFV replicon comprises one or more mutations conferring said replicon a non-cytopathic phenotype.

As it is used herein, the term "non-cytopathic replicon" or "replicon with a non-cytopathic phenotype" refers to the fact that the alphavirus replicon, particularly the SFV replicon, is not capable of inducing a series of morphological or functional changes in the cell as a result of viral infection, and which appear as cell rounding, substrate separation, cell lysis, formation of apoptotic bodies or halt in endogenous protein synthesis. The cytopathogenicity of an alphaviral replicon can be determined in a routine manner by a skilled person using any method known in the state of the art, including direct observation of cells after contacting the same with a vital dye, such as methyl violet, for example, as described in patent application WO2008065225.

As the person skilled in the art knows, there are different mutations having an effect where the alphavirus replicon, preferably an SFV replicon, has a non-cytopathic phenotype. Said mutations preferably affect the sequence encoding the non-structural polyprotein, i.e., the sequence affecting the replicase Rep. Even more preferably, said mutations affect the region of the sequence encoding the nsp2 subunit of said non-structural polyprotein. Still more preferably, said mutation is selected from the group consisting of mutations P718T, R649H and a combination of both. In an even more preferred embodiment of the polynucleotide of the invention, the SFV replicon has mutations P718T and R649H in the region encoding the nsp2 subunit of the non-structural polyprotein of the alphavirus or replicase Rep, as shown in SEQ ID NO: 2.

Transcription Termination Sequence

The polynucleotide of the invention comprises a transcription termination sequence in 3' position with respect to the 3' end of the DNA sequence complementary to the alphavirus replicon.

As it is used herein, the term "transcription termination sequence" refers to a DNA sequence directing the transcription termination by RNA polymerase. Said sequences can also direct post-transcriptional cleavage and polyadenylation of transcribed RNA. In a particular embodiment, the transcription termination sequence comprises a polyadenylation signal, referred to as polyadenylation/termination sequence. In a preferred embodiment, the termination sequence is derived from SV40 virus. In an even more preferred embodiment, the transcription termination sequence comprises the sequence shown in SEQ ID NO: 13.

Second Recognition Sequence for a Site-Specific Recombinase

The polynucleotide of the invention comprises a recognition sequence for a site-specific recombinase (hereinafter, second site-specific recombinase recognition sequence) located in 3' position with respect to the DNA sequence complementary to the alphavirus replicon.

In a preferred embodiment, the first recognition sequence for a site-specific recombinase (located in the DNA sequence complementary to an alphavirus replicon) and the second recognition sequence for a site-specific recombinase (located in 3' position with respect to the DNA sequence complementary to the alphavirus replicon) are heterospecific sequences, i.e., they are different sequences that cannot recombine with one another in the presence of said recombinase. Non-limiting illustrative examples of heterospecific recognition sequences for a site-specific recombinase are those described by Lee and Saito (Gene 1998, 216: 55-65)

In another preferred embodiment, the first and second recognition sequences for a site-specific recombinase are sequences incorporating mutations which cause recombination to be unidirectional, i.e., once recombination has taken place, the sequence flanked by recombination sites can no longer be cleaved by means of a new recombination. Non-limiting illustrative examples of sequences incorporating mutations such as those mentioned are the mutations described by Arakawa (Arakawa et al., 2001, BMC Biotechnology, 1: 7).

In a preferred embodiment, the first and second recognition sequences for a site-specific recombinase are heterospecific sequences and additionally incorporate mutations which cause recombination to be unidirectional.

In an even more preferred embodiment, the first and second LoxP sequences are selected from the group consisting of the pairs:
  (i) SEQ ID NO: 9 and SEQ ID NO: 10,
  (ii) SEQ ID NO: 11 and SEQ ID NO: 12,
  (iii) SEQ ID NO: 9 and SEQ ID NO: 12,
  (iv) SEQ ID NO: 11 and SEQ ID NO: 10,
  (v) SEQ ID NO: 10 and SEQ ID NO: 9,
  (vi) SEQ ID NO: 12 and SEQ ID NO: 11,
  (vii) SEQ ID NO: 10 and SEQ ID NO: 11, and
  (viii) SEQ ID NO: 12 and SEQ ID NO: 9.

In a particular embodiment, the structural genes of the alphavirus which are under the control of the subgenomic promoter have been removed. Said structural genes have preferably been substituted with a heterologous sequence.

In a particular embodiment of the polynucleotide of the invention, the sequence complementary to the alphavirus replicon further comprises a heterologous sequence in 3' position with respect to the replicon subgenomic promoter and with respect to the first recognition sequence for a site-specific recombinase.

As it is used herein, the term "heterologous sequence" refers to a sequence which is not naturally found in the alphavirus genome from which the replicon is derived to which the DNA sequence which is part of the polynucleotide of the invention is complementary. The heterologous sequence can be of any origin, i.e., it can be derived from any organism other than alphavirus from which the replicon is derived, or it can be an artificial sequence. In a particular embodiment, the heterologous sequence is selected from the group consisting of:
  (i) a stuffer sequence,
  (ii) a sequence comprising a multiple cloning site,
  (iii) a sequence of a gene of interest operatively bound to the alphavirus replicon subgenomic promoter, and
  (iv) any combination thereof.

In a preferred embodiment, the heterologous sequence is a stuffer sequence.

As it is used herein, the term "stuffer sequence" refers to a DNA sequence which is inserted into another DNA sequence for the purpose of increasing its size. Typically, stuffing regions do not contain regions encoding proteins, regions regulating gene expression or other regulatory elements of expression, such as promoter regions, transcriptional enhancers or RNA processing sites. The stuffer sequence can consist of at least 10, at least 20, at least 30, at least 40, at least 50, at least 60, at least 70, at least 80, at least 90, at least 100, at least 200, at least 300, at least 400, at least 500, at least 600, at least 700, at least 800, at least 900, at least 1000, at least 2000, at least 3000, at least 4000, at least 5000, at least 6000, at least 7000, at least 8000, at least 9000 or at least 10000 nucleotides.

As it is used herein", the term "open reading frame" or "ORF" refers to a DNA sequence comprised between a translation start codon (ATG) and an end codon. Said DNA sequence does not contain any internal end codon and can generally be translated into a peptide.

As it is used herein, the term "multiple cloning site" refers to a nucleic acid sequence comprising a series of two or more target sequences for restriction endonucleases close to one another. Multiple cloning sites include targets for restriction endonucleases allowing the insertion of fragments showing blunt ends, 5' overhanging ends or 3' overhanging ends.

As it is used herein, the term "gene of interest" refers to any gene the expression of which in a cell is desired. The gene of interest can be both a gene encoding a polypeptide or protein, and a gene which, once transcribed, gives rise to RNA capable of hybridizing with a messenger RNA sequence inhibiting its expression, such as small interfering RNA or siARN, micro RNA or small hairpin RNA or shARN, for example.

When the polynucleotide of the invention comprises a DNA sequence complementary to an alphavirus replicon further comprising a sequence of a gene of interest, said sequence is operatively bound to the alphavirus subgenomic promoter.

In a particular embodiment, the gene of interest encodes a protein of interest or a precursor thereof. As it is used herein, the term "protein of interest" refers to any protein the expression of which in a cell is to be achieved. The term "precursor" refers to a polypeptide which, once processed, can give rise to a protein of interest. In a particular embodiment, the precursor of the protein of interest is a polypeptide comprising a signal sequence or signal peptide. As it is used herein, the term "signal sequence" or "signal peptide" refers to a peptide of a relatively short length, generally between 5 and 30 amino acid residues, directing proteins synthesized in the cell towards the secretion pathway. The signal peptide usually contains a series of hydrophobic amino acids adopting a secondary alpha helix structure. Additionally, many peptides include a series of positively-charged amino acids that can contribute to the protein adopting the suitable topology for its translocation. The signal peptide tends to have at its carboxyl end a motif for recognition by a peptidase, which is capable of hydrolyzing the signal peptide giving rise to a free signal peptide and a mature protein.

In a particular embodiment of the polynucleotide of the invention, the protein of interest is a fluorescent protein, preferably green fluorescent protein or GFP. In another particular embodiment, the protein of interest is cardiotrophin-1. In another particular embodiment, the protein of interest is oncostatin-M. In another particular embodiment, the protein of interest is a single-chain antibody or an antibody heavy chain or light chain, preferably the A20 idiotype antibody heavy chain or light chain.

As it is used herein, the term "fluorescent protein" refers to a polypeptide with the capacity to emit light in response to the absorption of light or other electromagnetic radiation. Non-limiting illustrative examples of fluorescent proteins are green fluorescent protein (GFP or wtGFP), GFP variants for different emission wavelengths, emission intensity and/or protein stability such as Superfolder GFP, EGFP variants for different emission wavelengths (colors) such as blue fluorescent protein (EBFP), cyan fluorescent protein (ECFP), and yellow fluorescent protein (YFP), GFPuv (characterized by having mutations F99S, M153T and V163A in the GFP sequence), Emerald, mPlum, mCherry, tdTomato, mStrawberry, J-Red, mOrange, mKO, YFP, EYFP, mCitrine, Venus, YPet, CyPet, CFP, ECFP, mCFPm, Cerulean, and T-Sapphire. Other fluorescent polypeptides include red fluorescent protein (RFP), DsRed and variants thereof, DsRed2, DsRed-Express, RedStar, HcRedl, Kaede, EosFP, and Kindling fluorescent protein (KFP). In a particular embodiment, the fluorescent protein is green fluorescent protein or GFP.

As it is used herein, the term "green fluorescent protein" or "GFP" refers to a protein consisting of 239 amino acids with a molecular weight of 26.9 kDa and showing bright green fluorescence when exposed to blue ultraviolet light. Although many other marine organisms have similar green fluorescent proteins, GFP traditionally refers to the first protein isolated from jellyfish *A. victoria*. *A. victoria* GFP has a major excitation maximum at a wavelength of 395 nm and a minor one at 475 nm. The emission maximum thereof is at 509 nm. The fluorescence quantum yield of GFP is 0.79. In *A. victoria*, GFP transduces blue chemiluminescence of aequorin to green fluorescent light by means of energy transfer Alternatively or additionally, the heterologous polypeptide can be a polypeptide of therapeutic interest such that the vectors of the invention can be used for the in vitro expression of said polypeptide or for the treatment of diseases requiring expression of said polypeptide. The invention therefore contemplates vectors in which the heterologous sequence contains genes or cDNAs encoding one or more polypeptides of therapeutic interest including, without limitation, erythropoietin (EPO), leptins, adrenocorticotropin-releasing hormone (CRH), somatotropic-releasing hormone (GHRH), gonadotropin-releasing hormone (GnRH), thyrotropin-releasing hormone (TRH), prolactin-releasing hormone (PRH), melatonin-releasing hormone (MRH), prolactin-inhibiting hormone (PIH), somatostatin, adrenocorticotropic hormone (ACTH), somatotropic hormone or growth hormone (GH), luteinizing hormone (LH), follicle-stimulating hormone (FSH), thyrotropin (TSH or thyroid-stimulating hormone), prolactin, oxytocin, antidiuretic hormone (ADH or vasopressin), melatonin, Müllerian inhibiting factor, calcitonin, parathyroid hormone, gastrin, cholecystokinin (CCK), secretin, insulin-like growth factor I (IGF-I), insulin-like growth factor II (IGF-II), atrial natriuretic peptide (ANP), human chorionic gonadotropin (hCG), insulin, glucagon, somatostatin, pancreatic polypeptide (PP), leptin, neuropeptide Y, renin, angiotensin I, angiotensin II, factor VIII, factor IX, tissue factor, factor VII, factor X, thrombin, factor V, factor XI, factor XIII, interleukin 1 (IL-1), interleukin 2 (IL-2), tumor necrosis factor alpha (TNF-α), interleukin 6 (IL-6), interleukin 7 (IL-7), interleukin 8 (IL-8 and chemokines), interleukin 12 (IL-12), interleukin 16 (IL-16), interleukin 15 (IL-15), IL-15 receptor, interleukin 21 (IL-21), interleukin 24 (IL-24), alpha, beta, gamma interferons, CD3, ICAM-1, LFA-1, LFA-3, chemokines including RANTES 1α, MIP-1α, MIP-1β, nerve growth factor (NGF), platelet-derived growth factor (PDGF), transforming growth factor beta (TGF-beta), bone morphogenetic proteins (BMPs), fibroblast growth factors (FGF and KGF), epidermal growth factor (EGF and related factors), vascular endothelial growth factor (VEGF), granulocyte-colony stimulating factor (G-CSF), glial growth factor, keratinocyte growth factor, endothelial growth factor, alpha-1 antitrypsin, tumor necrosis factor, granulocyte-macrophage colony-stimulating factor (GM-CSF), cardiotrophin 1 (CT-1), oncostatin M (OSM), amphiregulin (AR), cyclosporin, fibrinogen, lactoferrin, tissue plasminogen activator (tPA), chymotrypsin, immunoglobins, hirudin, superoxide dismutase, imiglucerase, β-glucocerebrosidase, alglucosidase-α, α-L-iduronidase, iduronate-2-sulfatase, galsulfase, human A α-galactosidase, α-1 proteinase inhibitor, lactase, pancreatic enzymes (lipase, amylase, protease), adenosine deaminase, immunoglobulins, albumin, type A and B botulinum toxins, collagenase, human deoxyribonuclease I, hyaluronidase, papain, L-asparaginase, lepirudin, streptokinase, extra domain of fibronectin (EDA), transforming growth factor beta (TGF-β)-inhibiting peptides such as those described in WO0331155, WO200519244 and WO0393293, the content of which is incorporated herein by reference, suitable expression cassettes for the transcription of interfering RNA molecules (shRNA, siRNA, miRNA, RNA of modified U1 ribonucleoproteins).

In a preferred embodiment, the gene of interest encodes cardiotrophin-1 precursor.

As it is used herein, the term "cardiotrophin-1" or "CT-1" refers to a cytokine belonging to the interleukin 6 family, capable of binding and activating signaling mediated at least by the LIFR receptor complex consisting of the gp130/LIFRβ heterodimer. The cardiotrophin-1 can be of any origin, for example, human, bovine, murine, equine, canine, etc. In a preferred embodiment, the cardiotrophin is the human protein, with UniProt database accession number Q16619 (Mar. 6, 2013), including both isoform 1 (accession number Q16619-1) and isoform 2 (accession number Q16619-2).

In another preferred embodiment, the gene of interest encodes oncostatin M precursor.

As it is used herein, the term "oncostatin M" refers to a pleiotropic cytokine belonging to the interleukin 6 family. Oncostatin M is a glycoprotein with an approximate molecular weight of 28 kDa produced mainly by T-cells, monocytes/macrophages and dendritic cells. The oncostatin-M can be of any origin, for example, human, bovine, murine, equine, canine, etc. In a preferred embodiment, the oncostatin-M is the human protein with UniProt database accession number P13725 (Mar. 6, 2013).

In another preferred embodiment, the gene of interest encodes an antibody.

As it is used herein, the term "antibody" refers to a protein including at least one immunoglobulin variable region, for example, an amino acid sequence providing an immunoglobulin variable domain or a sequence of the immunoglobulin variable domain. An antibody can include, for example, a variable heavy chain (H) region (herein abbreviated as VH) and a variable light chain (L) region (herein abbreviated as VL). Typically, an antibody includes two variable heavy chain regions and two variable light chain regions. The term "antibody" encompasses antigen-binding antibody fragments (for example, single-chain antibodies, Fab fragments, F(ab')$_2$ fragments, Fd fragments, Fv fragments and dAb fragments) as well as whole antibodies, for example, intact and/or full length immunoglobulins of the IgA, IgG types (for example, IgG1, IgG2, IgG3, IgG4), IgE, IgD, IgM (as well as subtypes thereof).

The variable heavy and light chain regions can additionally be subdivided into hypervariability regions, referred to as "complementarity determining regions" ("CDR"), mixed together with more conserved regions, referred to as "framework regions" (FR). The extension of FRs and CDRs has been precisely defined (see Kabat, E. A., et al. (1991) Sequences of Proteins of Immunological Interest, Fifth Edition, The United States Department of Health and Human Services, NIH Publication No. 91-3242; and Chothia, C. et al. (1987) J. Mol. Biol. 196:901-917). Kabat definitions are used in the present document. Each variable heavy and light chain region is typically made up of three CDRs and four FRs, organized from the amino end to the carboxyl end in the following order: FR1, CDR1, FR2, CDR2, FR3, CDR3, FR4.

The antibody VH or VL chain can furthermore include all or part of a heavy chain or light chain constant region to thereby form a heavy chain (HC) or light chain (LC immunoglobulin, respectively. In one embodiment, the antibody is a tetramer having two immunoglobulin heavy chains and two immunoglobulin light chains. Immunoglobulin light and heavy chains can be bound by disulfide bridges. The heavy chain constant region typically includes three constant domains, CH1, CH2 and CH3. The light chain constant region typically includes a CL domain. The variable heavy and light chain region contains a binding domain interacting with an antigen. The constant regions of the antibodies typically mediate the binding of the antibody to host tissues or factors, including various cells of the immune system (for example, effector cells) and the first component (C1q) of the conventional complement system.

The term antibody encompasses both antibodies formed by heavy chains and light chains and single-chain antibodies. Therefore, in a particular embodiment the gene of interest encodes a single-chain antibody or a precursor thereof. In another preferred embodiment, the gene of interest encodes an antibody heavy chain or a precursor thereof. In another preferred embodiment, the gene of interest encodes an antibody light chain or a precursor thereof.

As it is used herein, the term "heavy chain" or "HC" encompasses both a full length heavy chain and fragments thereof. A full length heavy chain includes a variable region domain, $V_H$, and three constant region domains, $C_H1$, $C_H2$ and $C_H3$. The $V_H$ domain is at the amino terminal end of the polypeptide, and the $C_H3$ domain is at the carboxyl terminal end.

As it is used herein, the term "light chain" encompasses a full length light chain and fragments thereof. A full length light chain includes a variable region domain, $V_L$, and a constant region domain, $C_L$. Like the heavy chain, the variable light chain region domain is at the amino terminal end of the polypeptide.

As it is used herein, the term "single-chain antibody" refers to a molecule modified by means of genetic engineering containing the variable light chain region and the variable heavy chain region bound by means of a suitable peptide linker, formed as a genetically fused single-chain molecule.

As it is used herein, the term "A20 antibody" refers to the antibody produced by the mouse lymphoma cell line deposited under ATCC number TIB-208.

In a particular embodiment, the protein of interest additionally comprises at least one labeling sequence.

As it is used herein, the term "labeling sequence" or "labeling peptide" or "tag" refers to a polypeptide useful for making the detection, isolation and/or purification of a protein easier. Generally, said labeling sequence is located in a part of the protein of interest that does not adversely affect the functionality thereof. Virtually any polypeptide which can be used for detecting, isolating and/or purifying a protein can be present in the protein of interest. By way of non-limiting illustration, said polypeptide useful for detecting, isolating and/or purifying a protein, such as a protein of interest, can be, for example, an arginine tag (Arg-tag), a histidine tag (His-tag), FLAG-tag, Strep-tag, an epitope susceptible to being recognized by an antibody, such as c-myc-tag, SBP-tag, S-tag, calmodulin-binding peptide, cellulose-binding domain, chitin-binding domain, glutathione S-transferase-tag, maltose-binding protein, NusA, TrxA, DsbA, Avi-tag, etc. (Terpe K., 2003, Appl. Microbiol. Biotechnol. 60: 523-525), β-galactosidase, VSV-glycoprotein, etc. In a particular and preferred embodiment, the protein of interest comprises a polyhistidine tag.

In a particular embodiment, the alphavirus replicon comprises at least one sequence of a second gene of interest in 3' position with respect to the first recognition sequence for a site-specific recombinase. Said sequence of a second gene of interest can be
  (i) operatively bound to an additional subgenomic promoter, or
  (ii) operatively associated with the sequence of the first gene of interest, being bound to the sequence of the first gene of interest by means of an IRES or a sequence encoding a post-translational proteolytic cleavage site. In these cases, expression of the second gene of interest depends on the same subgenomic promoter controlling expression of the first gene of interest.

As it is used herein, the term "IRES" or "internal ribosomal entry site" refers to a sequence found in mRNA and is capable of recruiting translational machinery to an internal translation start codon with the aid of factors acting in trans (reviewed in Jackson, Translational Control of Gene Expression, pp. 127-184. Cold Spring Harbor Laboratory Press. 2000). IRES elements are frequently found in mRNA of viral origin. IRES elements useful for use in the present invention include, without limitation, picornavirus IRES (for example, poliovirus), encephalomyocarditis virus (EMCV), FMDV, IRES of flavivirus (for example, hepatitis C virus), IRES of pestivirus (for example, conventional swine fever virus (CSFV)), IRES of retrovirus (for example, murine leukemia virus or MLV), IRES of lentivirus (for example, Simian immunodeficiency virus or SIV) or IRES of cellular mRNA such as those found in translation factors (eIF4G), in transcription factors (c-Myc), IRES of growth factors (for example, VEGF, IGF-II, PDGF-2 or FGF-2), IRES of homeotic genes (for example, IRES of Antennapedia), IRES of survival proteins (for example, X-linked inhibitor of apoptosis (XIAP) or Apaf-1), IRES of chaperones (for example, the IRES of immunoglobulin heavy chain-binding protein or BiP).

As it is used herein, the term "sequence encoding a post-translational proteolytic cleavage site" refers to a nucleotide sequence which, once translated, gives rise to an amino acid sequence which is susceptible to being cleaved once the protein has been translated. In a preferred embodiment, the sequence encoding a post-translational proteolytic cleavage site is a sequence encoding an autoprotease, i.e., a protease acting in cis between the proteins resulting from the translation of the first gene of interest and the second gene of interest. In other words, in a particular embodiment said sequence encoding a post-translational proteolytic cleavage site is a nucleotide sequence which, when translated, provides a cleavage site whereby the expressed fusion protein or polyprotein is processed post-translation into proteins making up said fusion protein or polyprotein. By way of illustration, said autoprotease can originate from a virus, for example, a picornavirus, an alphavirus, etc. In a preferred embodiment, the autoprotease is foot-and-mouth disease virus or FMDV autoprotease 2A. Use of these post-translational autoproteolytic cleavage sites has been described previously in European patent application EP 736099 and also by Ryan and Drew (EMBO J. 1994, 13: 928-33), particularly use of the sequence encoding the 2A region of the FMDV polyprotein (FMDV autoprotease 2A).

Alternatively, in another particular embodiment said sequence encoding a post-translational proteolytic cleavage site is a nucleotide sequence encoding a cleavage site for a protease acting in trans; in this case, said protease could be expressed by the cell transfected with the viral vector of the invention, either in the native or recombinant manner, or alternatively, said protease could be exogenously added to release the heterologous product of interest from the fusion protein comprising the product of the first gene of interest and the product of the second gene of interest. Virtually any nucleotide sequence encoding a cleavage site for a protease acting in trans, and accordingly the amino acid sequence encoded by said sequence, can be used in the context of the present invention. By way of non-limiting illustration, said nucleotide sequence encoding a cleavage site of a protease acting in trans can be a nucleotide sequence encoding an amino acid sequence susceptible to being cleaved by an endopeptidase, etc. By way of non-limiting illustration, said nucleotide sequence encoding a cleavage site for a protease acting in trans is a nucleotide sequence encoding a cleavage site for a protease of a virus, for example, a potyvirus, such as the protease of etch tobacco virus (ETV), etc., and said protease could be expressed by the cell transfected with the viral vector of the invention (in the native manner or because it has been suitably transformed), etc.

Alternatively, in another particular embodiment said sequence encoding a post-translational proteolytic cleavage site is a nucleotide sequence encoding a cleavage site recognizable by a chemical reagent, e.g., cyanogen bromide cleaving methionine residues, etc.

In an even more particular embodiment, the alphavirus replicon comprises the sequences of two genes of interest. In a still more particular embodiment, said sequences are operatively bound to two different and independent subgenomic promoters. In an even more particular embodiment, the first gene of interest encodes a first antibody chain or a precursor thereof, and the second gene of interest encodes a second chain of said antibody or a precursor thereof. Said first and second chains refer to the heavy chain and light chain, respectively, or to the light chain and heavy chain, respectively. In an even more particular embodiment, said sequences are the A20 antibody light chain sequence and the antibody heavy chain sequence (ATCC TIB-208).

In a particular embodiment, the polynucleotide of the invention additionally comprises a selection gene located in the region comprised between the first and second recombinase recognition sites.

As it is used herein, the term "selection gene" refers to a gene the expression of which confers antibiotic resistance, a gene which allows synthesizing an essential nutrient which is omitted in the culture medium, or a gene offering a selective advantage to the cells that have incorporated said selection gene.

In a preferred embodiment, the selection gene is a gene the expression of which confers antibiotic resistance, for example, the gene conferring hygromycin resistance (hph), the gene conferring neomycin resistance (neoR), the gene conferring puromycin resistance (puromycin N-acetyltransferase or pac enzyme), etc. In an even more preferred embodiment of the polynucleotide of the invention, the gene conferring antibiotic resistance is selected from the group consisting of puromycin resistance gene and neomycin resistance gene.

Alternatively, the selection gene is a gene which allows synthesizing an essential nutrient which is omitted in the culture medium. An example includes *Escherichia coli* trpB gene encoding the beta subunit of tryptophan synthase. This gene allows mammalian cell survival and multiplication in medium containing indole instead of tryptophan. A second example includes *Salmonella typhimurium* hisD gene encoding histidinol dehydrogenase which catalyzes the NAD+-dependent oxidation of L-histidinol to L-histidine in two steps. In medium lacking histidine and containing histidinol, only the mammalian cells expressing the hisD product can survive (Hartman S. C. and Mulligan R. C., 1988, Proc. Natl. Acad. Sci. USA. 85(21): 8047-51).

An example of a selection gene offering a selective advantage to cells that have incorporated said gene includes the gene encoding dihydrofolate reductase (DHFR) in cells genetically engineered to be DHFR deficient. The DHFR protein catalyzes the reduction of 5,6-dihydrofolate to 5,6,7,8-tetrahydrofolate, an essential step in purine metabolism. Use of DHFR allows the genetic selection of DHFR deficient cells, making them grow in the absence of the hypoxanthine and thymidine (HT) purine precursors (Kaufman R. J. and Sharp P. A., 1982, J. Mol. Biol., 159(4): 601-21).

If the transcription regulatory sequence which is operatively bound to the DNA sequence complementary to the alphavirus replicon is a regulable sequence, the selection gene is located outside the alphavirus replicon and is operatively bound to a constitutive promoter. Therefore, it is not necessary for transcription of the DNA sequence complementary to the alphavirus replicon to take place in order to express the selection gene, such that the selection of cells that have incorporated the nucleotide of the invention can be done without having to add the ligand activating the regulable promoter controlling transcription of the DNA sequence complementary to the alphavirus replicon. If the transcription regulatory sequence which is operatively bound to the DNA sequence complementary to the alphavirus replicon comprises a constitutive promoter, the selection gene can be
  (i) associated with the sequence of the gene of interest by means of an IRES or by a sequence encoding a post-translational proteolytic cleavage site, or alternatively,
  (ii) under the control of a second constitutive promoter.

The terms "IRES" and "sequence encoding a post-translational proteolytic cleavage site" have been described above. In a preferred embodiment, the sequence encoding a post-translational proteolytic cleavage site is a sequence encoding an autoprotease. In a particular embodiment, the protease is FMDV protease 2A.

In a particular embodiment, when the selection gene is operatively bound to a constitutive promoter other than the promoter regulating expression of the DNA sequence complementary to the alphavirus replicon, said constitutive promoter comprises the nucleotide sequence which is shown in SEQ ID NO: 14.

In a particular embodiment, the polynucleotide of the invention additionally comprises a polyadenylation signal or a polyadenylation and transcription termination signal in 3' position with respect to the second site-specific recombinase recognition site.

As it is used herein, the term "polyadenylation signal" refers to a nucleic acid sequence mediating the binding of a polyadenine segment (poly(A)) to the 3' end of messenger RNA. The poly(A) tag can be of any size provided that it is sufficient to increase stability in the cytoplasm of the polynucleotide of the invention. The poly(A) tag comprises at least 10 adenosine nucleotides and more preferably at least 25 or 40 adenosine nucleotides. Polyadenylation signals suitable for use in the present invention include, without limitation, SV40 early-late polyadenylation signal, herpes simplex virus or HSV thymidine kinase polyadenylation signal, protamine gene polyadenylation signal, adenovirus 5 EIb polyadenylation signal, bovine growth hormone polyadenylation signal, human growth hormone variant polyadenylation signal and the like. The term "polyadenylation and transcription termination signal" refers to a nucleotide sequence comprising a transcription termination sequence and a polyadenylation signal. In a particular embodiment, the polynucleotide of the invention comprises a polyadenylation and transcription termination signal in 3' position with respect to the second site-specific recombinase recognition site. In an even more particular embodiment, the polyadenylation and transcription termination signal is the polyadenylation and transcription termination signal of the HSV-derived thymidine kinase gene. In a particular embodiment, the polyadenylation and transcription termination signal comprises the sequence SEQ ID NO: 70.

The polynucleotide of the invention can be incorporated in an expression vector for the purpose of being administered to a target. Therefore, in another aspect the invention relates to an expression vector, hereinafter first expression vector of the invention, comprising the polynucleotide of the invention.

Expression Vectors of the Invention

As it is used herein, the term "expression vector" or "expression plasmid" refers to a replicative DNA construct used for expressing the polynucleotide of the invention in a cell, preferably a eukaryotic cell, more preferably a mammalian cell. The first expression vector also preferably contains an origin of replication in prokaryotes, necessary for vector propagation in bacteria. Additionally, the first expression vector can also contain a selection gene for bacteria, for example, a gene encoding a protein conferring resistance to an antibiotic, for example, ampicillin, kanamycin, chloramphenicol, etc. The first expression vector can also contain one or more multiple cloning sites.

The polynucleotide of the invention as well as the RNA or DNA constructs necessary for preparing the expression vector of the invention can be obtained by means of conventional molecular biology methods included in general laboratory manuals, for example, in "Molecular cloning: a laboratory manual" (Joseph Sambrook, David W. Russel Eds. 2001, 3$^{rd}$ ed. Cold Spring Harbor, N.Y.) or in "Current protocols in molecular biology" (F. M. Ausubel, R. Brent, R. E. Kingston, D. D. Moore, J. A. Smith, J. G. Seidman and K. Struhl Eds, vol. 2. Greene Publishing Associates and Wiley Interscience, New York, N.Y. Updated in September 2006).

The alphavirus or alphavirus genomes or fragments thereof can be obtained by means of various techniques and sources. They can be artificially synthesized, cloned from plasmids or virus isolated using RT-PCR, or directly derived or purified from virus samples deposited in libraries.

Cells of the Invention

The polynucleotide of the invention, as well as the expression vector comprising said polynucleotide, can be used for transforming, transfecting or infecting cells which can be transformed, transfected or infected by said nucleotide or vector. Therefore, in another aspect the invention relates to a eukaryotic cell, hereinafter cell of the invention, comprising a polynucleotide of the invention or an expression vector comprising a polynucleotide of the invention.

By way of example, the vector or plasmid comprising the polynucleotide of the invention can be a vector or plasmid which, when introduced in a host cell, is integrated in the genome of said cell and replicates along with the chromosome (or chromosomes) in which it has been integrated. Therefore, in another aspect the invention relates to a cell comprising a polynucleotide of the invention integrated in the genome thereof.

The cells of the invention can be obtained by introducing in a cell the polynucleotide of the invention or the expression vector incorporating the polynucleotide of the invention by means of well-known techniques such as infection, transduction, transfection, electroporation and transformation using the polynucleotide of the invention that has been isolated, incorporated in artificial liposomes or being part of the expression vector mentioned above.

As it is used herein, the term "eukaryotic cell" refers to a cell having a differentiated nucleus demarcated by a membrane, such as an animal cell, for example.

In a preferred embodiment, the cell of the invention is a mammalian cell, even more preferably a BHK cell, i.e., a newborn hamster kidney cell. In another particular embodiment, the eukaryotic cell is a cell which can grow in suspension, i.e., a cell which can grow in culture without adhering to a culture surface.

If the polynucleotide of the invention comprises a DNA sequence complementary to an alphavirus replicon operatively bound to a transcription regulatory sequence wherein said sequence is a ligand-regulable sequence, it may be of interest for the cell to additionally comprise a DNA sequence encoding a transcriptional activator operatively bound to a constitutive promoter, wherein said transcriptional activator is capable of regulating transcription from the transcription regulatory sequence by means of the binding thereof to the ligand responsive element site. Therefore, when said cell is contacted with the ligand of the transcriptional activator, said activator will adopt a conformational change that will allow it to bind to the transcription regulatory sequence that is bound to the DNA sequence complementary to the alphavirus replicon, activating transcription thereof.

Therefore, in a particular embodiment the transcription regulatory sequence which is operatively bound to the alphavirus replicon complementary sequence is a regulable sequence, and the cell additionally comprises a DNA sequence encoding a transcriptional activator operatively bound to a constitutive promoter, wherein said transcriptional activator is capable of regulating transcription from said transcription regulatory sequence by means of the binding thereof to the ligand responsive element site.

As it is used herein, the term "transcriptional activator" or "transactivator" refers to a polypeptide which, when bound to a ligand, is capable of promoting transcription of a polynucleotide which is operatively bound to a transcription regulatory sequence comprising responsive elements specific for said ligand. In other words, the activity of a transcription regulatory sequence can be modulated by additional factors that can be supplied or removed depending on the need to promote transcription of the polynucleotides the expression of which they regulate. Those skilled in the art will note that the transcriptional activator, in the presence of its ligand, is capable of binding to the transcription regulatory sequence having regulable activity which is operatively bound to the DNA sequence complementary to the alphavirus replicon, regulating the activity of the promoter comprised in said regulatory sequence and therefore regulating the expression of said DNA sequence complementary to the alphavirus replicon.

Additionally, the person skilled in the art will see that the invention contemplates any method for regulating expression of the transcriptional regulator provided that it allows regulated expression with a minimum baseline transcription. Particularly, the invention contemplates the use of transcriptional regulators the induction of which takes place not by means of an increase in expression levels of the transcriptional regulator but by means of a conformational change in response to the binding of the inducing agent, which can result in translocation of the transcription factor to the nucleus where it exerts its effect, or in an increase in transcriptional activity. Such transcriptional regulators are usually formed by a DNA binding domain or DBD, a ligand binding domain or LBD, and a transcription activating domain or AD.

The DNA binding domain can be any domain for which there is a known specific binding element, including synthetic, chimeric or analogous DNA binding domains. DNA binding domains suitable for the present invention include (i) homeodomains (Scott et al., 1989, Biochim. Biophys. Acta 989:25-48; Rosenfeld et al., 1991, Genes Dev. 5:897-907) formed generally by a strand of about 61 amino acids having a secondary structure made up of three alpha helices, (ii) zinc fingers formed by two to three dozens of fingers of general formula Cys2His2 organized in tandem (for example, TFIIIA, Zif268, Gli, and SRE-ZBP) wherein each module comprises an alpha helix capable of contacting with a 3 to 5 base pair DNA region, at least 3 zinc fingers being necessary for generating a high-affinity DNA binding site and at least two zinc fingers for generating low-affinity DNA binding sites, (iii) the DNA binding domains referred to as helix-loop-helix or HLH such as TetR, MAT1, MAT2, MATa1, Antennapedia, Ultrabithorax, Engrailed, Paired, Fushi tarazu, HOX, Unc86, Oct1, Oct2 and Pit-1, (iv) leucine zipper-type DNA binding domains such as GCN4, C/EBP, c-Fos/c-Jun and JunB. Examples of DNA binding domains suitable in the present invention include the DNA binding domain of GAL4, LexA, transcription factors, group H nuclear receptors, nuclear receptors from the steroid/thyroid hormone superfamily. The person skilled in the art will see that the invention contemplates the use of hybrid DNA binding domains formed by various DNA binding motifs that can recognize DNA binding sites other than those of the elements making up same. Therefore, use of DNA binding domains formed by the binding of a zinc finger and a homeobox is possible. In a preferred embodiment, the DNA binding domain is that originating from *E. coli* transcriptional Tet repressor.

The ligand binding sequences capable of promoting the nuclear localization of a transcriptional activator containing same, suitable for use in the present invention, include the PPAR-derived localization sequence (receptors activated by peroxisomal activators), which are translocated to the nucleus in the presence of 15-deoxy-[Delta]-prostaglandin J2, retinoic acid receptors which are translocated to the nucleus in the presence of alpha, beta or gamma isomers of the 9-cis-retinoic acid, farnesoid X receptors that can be activated by retinoic acid and TTNPB, liver X receptors that can be activated by 24-hydroxycholesterol, benzoate X receptors that can be activated by 4-amino-butylbenzoate, constitutive androstane receptor, pregnane receptors inducible by pregnenolone-16-carbonitrile, steroid and xenobiotic receptors inducible by rifampicin, progesterone receptors that can be activated by medroxyprogesterone as well as by agonists and antagonists of mifepristone and 19-nortestosterone derivatives, glucocorticoid receptors that can be activated by glucocorticoids, thyroid hormone receptors that can be activated by T3 and/or T4, and estrogen receptors that can be activated by estrogens and the derivatives thereof such as 17-beta-estradiol and estradiol, tTA transactivators that can be activated by "tet-off" tetracycline/doxycycline (Gossen and Bujard, 1992, Proc. Natl. Acad. Sci. USA, 89: 5547-5551), rtTA transactivators that can be activated by "tet-on" tetracyclines (Gossen et al., 1995, Science, 268: 1766-1769), transactivator inducible by muristerone A or analogous ligands of the ecdysone receptor (No et al., 1996, Proc. Natl. Acad. Sci. USA, 93: 3346-3351), transactivators that can be activated by the RSL1 ligand, such as the RheoSwitch system initially described by Palli et al. (2003, Eur. J. Biochem., 270: 1308-1315), a transactivator that can be activated by rapamycin or rapamycin analogues (Ho et al., 1996, Nature, 382: 822-826; Amara et al., 1997, Proc. Natl. Acad. Sci. USA, 94: 10618-10623), and a transactivator that can be activated by coumermycin/novobiocin, acting competitively as inducer and repressor, respectively (Zhao et al., 2003, Hum. Gene Ther., 14: 1619-1629).

Finally, the transcription activating domain can be an acidic activating domain, an activating domain rich in prolines, an activating domain rich in serines/threonines and an activating domain rich in glutamine. Examples of acidic activating domains include the VP16 regions and the GAL4 region formed by amino acids 753-881. Examples of transcription activating domains rich in proline include amino acids 399-499 of CTF/NF1 and amino acids 31-76 of AP2. Examples of activating domains rich in serine-threonine include amino acids 1-427 of ITF1 and amino acids 2-452 of ITF2. Examples of activating domains rich in glutamine include amino acids 175-269 of Oct1 and amino acids 132-243 of Sp1. The sequences of each of the regions described as well as other transcription activating domains have been described by Seipel, K. et al. (EMBO J. (1992) 13:4961-4968). Additionally, other transcription activating domains can be obtained from the preceding domains using methods known in the state of the art. Additionally, the activating domain can be the activating domain of group H nuclear receptors, steroid or thyroid hormone nuclear receptors, the activating domain of VP16, GAL4, NF-κB, B42, BP64 or p65.

In a preferred embodiment, the transcription activating domain is the protein 16 of herpes simplex virion (hereinafter VP16), the amino acid sequence of which has been described by Triezenberg, S. J. et al. (Genes Dev., 1988, 2:718-729). This domain can consist of about 127 amino acids of VP16 C-terminal end. Alternatively, the transcription activating domain can consist of the 11 amino acids of the VP16 C-terminal region which maintain the capacity for activating transcription. Suitable VP16 C-terminal end regions suitable for use thereof as transcription activating domains have been described by Seipel, K. et al. (EMBO J. (1992) 13:4961-4968). In an even more preferred embodiment, the transcriptional activator comprises the minimum region of said protein formed by 13 amino acids the sequence of which is PADALDDFDLDML (SEQ ID NO: 15) as described by Baron et al. (Nucleics Acids. Res., 1997, 25:2723-2729).

In a preferred embodiment, the transcriptional activator is a transcriptional activator that can be activated by tetracycline or the analogues thereof.

As it is used herein, the term "tetracycline analogue" refers to compounds structurally related to tetracycline with the capacity of binding to tetracycline repressor (TetR) with a Ka of at least about $10^{-6}$ M. The tetracycline analogue preferably has an affinity for TetR of at least $10^{-9}$ M. Examples of tetracycline analogues suitable for the present invention include, without limitation, anhydrotetracycline, doxycycline (Dox), chlortetracycline, oxytetracycline, epioxytetracycline, cyanotetracycline, demeclocycline, meclocycline, methacycline and others which have been described by Hlavka and Boothe, "The Tetracyclines" in "Handbook of Experimental Pharmacology 78, R. K. Blackwood et al. (eds.), Springer-Verlag, Berlin-New York, 1985; L. A. Mitscher, "The Chemistry of the Tetracycline Antibiotics", Medicinal Research 9, Dekker, N.Y., 1978; Noyee Development Corporation, "Tetracycline Manufacturing Processes" Chemical Process Reviews, Park Ridge, N.J., 2 volumes, 1969; R. C. Evans, "The Technology of the Tetracyclines", Biochemical Reference Series 1, Quadrangle Press, New York, 1968; and H. F. Dowling, "Tetracycline", Antibiotic Monographs, no. 3, Medical Encyclopedia, New York, 1955.

In a particular embodiment, the tetracycline analogue is doxycycline.

In a preferred embodiment, the transcriptional activator that can be activated by tetracyclines can be the so-called reverse tetracycline repressor protein, or reverse tetR, referring to a polypeptide which (i) shows specific affinity for the inducing agent, (ii) shows specific affinity for the tet-type responsive element when it is bound to the inducing agent, and (iii) is displaced from the tet element when it is not bound to the inducing agent. This activator includes both natural forms thereof and functional derivatives. In a preferred embodiment, the tetracycline-regulable activator can be the so-called tetracycline-dependent reverse transactivator (rtTA), characterized in that in the presence of tetracycline or its analogues, it undergoes a conformational change allowing it to be converted into a transcription activator, being inactive in the absence of tetracycline. Problems associated with transactivators derived from E. coli TetR repressor which is capable of activating transcription of genes which have tetracycline responsive elements in the absence of tetracycline and which, in the presence of tetracycline, would no longer activate same, are therefore prevented. Tetracycline-dependent reverse transactivators (rtTA) preferably include the transactivator rtTA or any of rtTA variants described by Urlinger, S. et al. (Proc. Natl. Acad. Sci USA, 2000; 97:7963-7968). In a preferred embodiment, the rtTA variant is the variant known as rtTA2sM2, characterized in that it requires for the activation thereof a doxycycline concentration 10 times less than that required by the original rtTA. The rtTA2sM2 transactivator is a polypeptide encoded by the polynucleotide of sequence SEQ ID NO: 16.

The term "constitutive promoter" has been described above in relation to the polynucleotide of the invention.

The DNA sequence encoding a transcriptional activator operatively bound to a constitutive promoter can be incorporated to the cell of the invention by means of well-known techniques such as infection, transduction, transfection, electroporation and transformation using said DNA sequence that has been isolated, incorporated in artificial liposomes or being part of an expression vector.

In a preferred embodiment, the DNA sequence encoding a transcriptional activator operatively bound to a constitutive promoter is integrated in the genome of the cell of the invention.

In a particular embodiment, the DNA sequence encoding a transcriptional activator additionally comprises a selection gene operatively associated with the sequence encoding said transcriptional activator by means of an IRES or by means of a sequence encoding a post-translational proteolytic cleavage site. The term selection gene has been defined previously in relation to the polynucleotide of the invention. In a preferred embodiment, the selection gene which is part of the DNA sequence encoding a transcriptional activator is a gene encoding a protein conferring hygromycin resistance. The selection gene is operatively bound to the same promoter as the transcriptional activator, said selection gene and said transcriptional activator being separated by an IRES. The terms "IRES" and "sequence encoding a post-translational proteolytic cleavage site" have been described above in relation to the polynucleotide of the invention. In a particular embodiment, the sequence encoding a post-translational proteolytic cleavage site is a sequence encoding an autoprotease, preferably the FMDV autoprotease 2A.

First "In Vitro" Method for Generating a Cell Line Capable of Expressing a Gene of Interest When the polynucleotide of the invention comprises a heterologous sequence comprising the sequence of a gene of interest, said polynucleotide, or a vector comprising said polynucleotide, can be used for generating a cell which is capable of expressing said gene of interest. Therefore, in another aspect the invention relates to an in vitro method, hereinafter first method of the invention, for generating a cell line capable of expressing a gene of interest which comprises (i) contacting a cell with the polynucleotide of the invention, wherein said polynucleotide additionally comprises said gene of interest operatively bound to the replicon subgenomic promoter, or with an expression vector comprising said polynucleotide, and (ii) selecting cells that have incorporated said polynucleotide or an expression vector comprising said polynucleotide.

As it is used herein, the term "in vitro" refers to the fact that the method is not carried out on the body of a human or animal subject, but rather on cells isolated from said subject.

Step (i) of the first method of the invention involves contacting a cell with the polynucleotide of the invention, additionally comprising the gene of interest operatively bound to the replicon subgenomic promoter, or with a vector comprising said polynucleotide. This step results in the polynucleotide, or the vector comprising said polynucleotide, being incorporated within the cell, and can be carried out by means of any technique known by the person skilled in the art for introducing polynucleotides or vectors in a cell. Non-limiting illustrative examples of techniques which can be used for introducing polynucleotides or vectors in a cell include infection, transduction, transfection, electroporation and transformation using the polynucleotide of the invention that is isolated and incorporated in artificial liposomes or being part of the expression vector mentioned above.

Step (ii) of the method comprises selecting those cells that have incorporated the polynucleotide of the invention, additionally comprising the gene of interest operatively bound to the replicon subgenomic promoter or an expression vector comprising said polynucleotide. Said selection can be carried out by means of any suitable technique known by the person skilled in the art. For example, clones can be obtained from the cells resulting from step (i) of the first method of the invention by means of, for example, limit dilution of said cells as described in detail in the examples. Said clones can be analyzed to detect the incorporation of the polynucleotide of the invention by means of any technique known by the person skilled in the art suitable for detecting specific polynucleotide sequences, for example, by means of polymerase chain reaction, or the presence of a protein encoded by the polynucleotide of the invention can be detected by means of any technique known by the person skilled in the art suitable for detecting proteins, for example, immunofluorescence, flow cytometry, immunoblotting, etc.

If the polynucleotide of the invention comprises a selection gene, selection can be carried out by putting the cells in restrictive conditions depending on the type of selection gene, i.e., in conditions in which expression of the selection gene entails an advantage for the cells. For example, if the polynucleotide of the invention comprises a selection gene which allows synthesizing a nutrient, the selection of step (ii) of the first method of the invention will comprise putting the cells in a culture medium lacking said nutrient. If the polynucleotide of the invention comprises a selection gene expression of which confers antibiotic resistance, the selection of step (ii) of the first method of the invention will comprise putting the cells in a culture medium comprising said antibiotic for which the selection gene provides resistance.

In a particular embodiment of the first method of the invention, the polynucleotide of the invention comprises a resistance gene conferring antibiotic resistance, preferably neomycin or puromycin resistance, therefore step (ii) of the method comprises putting the cells in a culture medium containing neomycin or puromycin, whichever is appropriate.

In a particular embodiment, the transcription regulatory sequence which is operatively bound to the DNA sequence complementary to the alphavirus replicon is a regulable sequence, therefore the first method of the invention additionally comprises the steps of (iii) introducing in said cell a polynucleotide encoding a transcriptional activator specific for said transcription regulatory sequence, and (iv) selecting cells that have incorporated said polynucleotide encoding a transcriptional activator specific for said transcription regulatory sequence.

The terms "transcriptional activator" and "regulatory sequence having regulable activity" have been described above in relation to the polynucleotide and cell of the invention.

In a preferred embodiment of the first method of the invention, the transcriptional activator is a ligand-regulable transcriptional activator, preferably a tetracycline- or tetracycline analogue-regulable transcriptional activator, and the transcription regulatory sequence regulable by said transcriptional activator which is operatively bound to the DNA sequence complementary to the alphavirus replicon is a tetracycline- or tetracycline analogue-regulable sequence.

In a more preferred embodiment, the transcriptional activator is a doxycycline-regulable transcriptional activator.

In an even more preferred embodiment, the doxycycline-regulable transcriptional activator is the transcriptional activator which is located downstream of the PGK gene promoter, as described by Urlinger (Urlinger et al., supra) or a functionally equivalent variant thereof.

In a still more preferred embodiment, the doxycycline-regulable transcriptional activator comprises the sequence SEQ ID NO: 16.

Steps (iii) and (iv) can be carried out by means of any of the techniques mentioned above in relation to steps (i) and (ii) of the first method of the invention. Steps (iii) and (iv) can be carried out simultaneously, before or after steps (i) and (ii).

In a particular embodiment of the first method of the invention, the polynucleotide of the invention comprises a first selection gene, and the polynucleotide encoding a transcriptional activator specific for the regulable promoter comprises a second selection gene, therefore step (ii) of selecting cells that have stably incorporated the polynucleotide of the invention additionally comprising a first selection gene and step (iv) of selecting cells that have stably incorporated the polynucleotide encoding a transcriptional activator and additionally comprising a second selection gene are carried out in selective conditions for cells expressing said first and/or second selection gene.

In a particular embodiment, the first and second selection genes are genes conferring antibiotic resistance. The first and second selection genes are preferably different.

In a particular embodiment, the first selection gene is selected from the gene conferring neomycin resistance and the gene conferring puromycin resistance. In a particular embodiment, the second selection gene is the gene conferring hygromycin resistance. In a particular embodiment, the first selection gene is selected from the gene conferring neomycin resistance and the gene conferring puromycin resistance and the second selection gene is the gene conferring hygromycin resistance.

Method for Expressing a Gene of Interest

The cell of the invention can comprise a polynucleotide or a vector comprising said polynucleotide, comprising a heterologous sequence of a gene of interest, and therefore said cell can be used for expressing said gene of interest. Therefore, in another aspect the invention relates to a method for expressing a gene of interest, hereinafter method for expressing a gene of interest of the invention, which comprises putting the cell of the invention, wherein said cell comprises the polynucleotide of the invention which furthermore additionally comprises the sequence of the gene of interest operatively bound to the replicon subgenomic promoter, or with an expression vector comprising said polynucleotide, in suitable conditions for activating transcription of the sequence complementary to the alphaviral replicon.

Suitable conditions for activating transcription of the DNA sequence complementary to the alphaviral replicon will depend on the type of transcription regulatory sequence to which said sequence complementary to the alphaviral replicon is operatively bound. Therefore, when the DNA sequence complementary to the alphaviral replicon is operatively bound to a regulatory sequence having constitutive activity, said suitable conditions will comprise common cell culture conditions. Said conditions will depend on the type of cell and are known by the person skilled in the art. In a particular embodiment, the cells are BHK cells and the culture conditions are those shown in the examples. When the DNA sequence complementary to the alphaviral replicon is operatively bound to a transcription regulatory sequence having regulable activity, said conditions will comprise suitable conditions for activating said regulatory sequence and will vary depending on the type of regulatory sequence. For example, in one embodiment the transcription regulatory sequence controlling expression of the alphaviral replicon is a ligand-regulable sequence in the presence of a specific transcriptional activator, therefore said conditions comprise contacting the cell with said ligand or a precursor thereof. In a preferred embodiment, the regulatory sequence controlling expression of the DNA sequence complementary to the alphavirus replicon is a sequence regulable by tetracycline or a tetracycline analogue, for example doxycycline, and the suitable conditions for activating said regulatory sequence comprise contacting the cell with tetracycline or a tetracycline analogue, for example doxycycline.

The person skilled in the art will determine the time necessary for the cells to be in contact with the ligand as well as the necessary concentration thereof so that expression of the gene of interest takes place. As a guideline, if the ligand is doxycycline, the cells will be put in contact with doxycycline for a time period comprised between 4 hours and 120 hours, preferably 96 hours, at a doxycycline concentration comprised between 0.25 and 10 µg/ml, preferably between 1 and 2.5 µg/ml, more preferably at 1.25 µg/ml, and at a temperature of between 28° C. and 40° C., preferably between 30° C. and 35° C., more preferably at 33° C. In a particular embodiment, the cells are put in contact with doxycycline at a concentration of 1.25 µg/ml for 96 hours and at a temperature of 33° C.

In one embodiment, the conditions suitable for activating transcription of the DNA sequence complementary to the alphaviral replicon are those allowing expression of the gene of interest. Expression of the gene of interest can be determined by means of any technique known by the person skilled in the art. For example, if the gene of interest encodes a protein of interest, the expression of said gene can be determined by means of detecting said protein, using to that end any technique commonly used by the person skilled in the art for detecting proteins such as immunofluorescence, flow cytometry, immunoblotting, ELISA, etc. If said protein comprises a labeling sequence, the latter can be used for detecting the protein of interest and differentiating it from a possible endogenous expression of said protein. The protein of interest can also be detected by means of an assay which allows detecting biological activity of said protein, as described in the examples for proteins cardiotrophin-1 and oncostatin-M. If the gene of interest, once transcribed, gives rise to an RNA capable of hybridizing with a messenger RNA sequence inhibiting the expression thereof, such as for example, small interfering RNA, micro RNA or small hairpin RNA, expression of the gene of interest can be detected by means of detecting said RNA by means of any technique known by the person skilled in the art suitable for detecting such RNA, including generic methods for detecting nucleic acids, particularly RNA and optimized methods for detecting small RNA species. Non-limiting illustrative examples of methods which can be used for detecting such RNA include:

a. methods based on hybridization, such as Northern blot analysis and in situ hybridization;
b. multiplex and/or singleplex real time RT-PCR;
c. detection of individual molecules as described by Neely, et al., Nat. Methods. 3(1):41-6 (2006) and in patent documents U.S. Pat. No. 6,355,420; U.S. Pat. No. 6,916,661 and U.S. Pat. No. 6,632,526;
d. bead-based flow cytometry methods as described by Lu, et al., Nature 435:7043 (2005) and in patent document U.S. Pat. No. 6,524,793; and
e. assays using nucleic acid arrays as described by Nelson, et al., Nat. Methods 1(2):155-61 (2004); Wu, et al., RNA 13(1):151-9 (2007) and in patent documents U.S. Pat. No. 6,057,134; U.S. Pat. No. 6,891,032; U.S. Pat. No. 7,122,303; U.S. Pat. No. 6,458,583; U.S. Pat. No.

6,465,183; U.S. Pat. No. 6,461,816; U.S. Pat. No. 6,458,583; U.S. Pat. No. 7,026,124; U.S. Pat. No. 7,052,841; U.S. Pat. No. 7,060,809; U.S. Pat. No. 6,436,640 and U.S. Pat. No. 7,060,809.

Second Vector of the Invention

Once a cell which has incorporated in its genome the nucleotide of the invention comprising a heterologous sequence, for example, the sequence of a gene of interest, has been obtained, it is possible to exchange said heterologous sequence with a second heterologous sequence, for example, a second gene of interest, such that a cell capable of expressing the second gene of interest is obtained. To carry out said substitution of the first heterologous sequence with the second heterologous sequence, a "shuttle" expression vector can be used, which comprises the second heterologous sequence flanked by recognition sequences for a recombinase capable of recombining with recognition sequences for recombinase that are present in the polynucleotide which is integrated in the target cell. In this sense, the invention relates to a vector, hereinafter second vector of the invention, comprising a DNA sequence comprising, ordered in the 5' to 3' direction,
(i) a first recognition sequence for a site-specific recombinase,
(ii) a sequence of a gene of interest,
(iii) a 3' sequence necessary for replication of an alphavirus,
(iv) a transcription termination sequence,
(v) a sequence of a selection gene operatively bound to a promoter, and
(vi) a second recognition sequence for a site-specific recombinase.

The terms "vector", "recognition sequence for a site-specific recombinase", "gene of interest", "3' sequence necessary for the replication of an alphavirus", "transcription termination sequence", "selection gene", "promoter" and "operatively bound", as well as particular and preferred embodiments thereof, have been described previously.

In a particular embodiment, the second vector of the invention does not comprise a polyadenylation signal between the sequence of the selection gene (v) and the second recognition sequence for a site-specific recombinase (vi). This allows, if the region comprised between the two recognition sequences for a recombinase is randomly integrated in any site of the cell genome other than the suitable region, the selection gene to not be suitably expressed as it lacks the polyadenylation signal. Therefore, only those cells in which the region of the second vector of the invention comprised between the two recombination sequences is integrated in the suitable region, i.e., in the region comprised between the two recombination sequences present in the polynucleotide of the invention integrated in the genome of said cell, will be selected when said cells are put in selective conditions selecting for the selection gene comprised in the second vector of the invention.

In a particular embodiment, the second vector of the invention additionally comprises at least one sequence of an additional gene of interest, for example, two, three or more sequences of additional genes of interest. In this particular embodiment, the sequence of the additional gene of interest can be:
a. separated from the sequence of the first gene of interest by an IRES or by a sequence encoding a post-translational proteolytic cleavage site, such that when the DNA fragment comprised between the recombinase recognition sites is integrated in the target cell both the first gene of interest and the additional gene or genes of interest will be operatively bound to the alphavirus subgenomic promoter, or
b. operatively bound to a subgenomic promoter located between the sequence of the gene of interest (ii) and the 3' sequence necessary for replication of the alphavirus (iii).

The terms "IRES" and "sequence encoding a post-translational proteolytic cleavage site" have been described above in relation to the nucleotide of the invention. In a preferred embodiment, the sequence encoding a post-translational proteolytic cleavage site is a sequence encoding an autoprotease, preferably FMDV autoprotease 2A.

In a particular embodiment, the 3' sequence necessary for replication of the alphavirus originates from the Semliki Forest Virus.

In a preferred embodiment, the recognition sequences for a site-specific recombinase are LoxP sequences.

The term "LoxP sequence" has been described above in relation to the polynucleotide of the invention.

In a preferred embodiment, the first and second recognition sequences for a site-specific recombinase are heterospecific sequences, i.e., they are different sequences that cannot recombine with one another in the presence of said specific recombinase.

In another preferred embodiment, the first and second recognition sequences for a site-specific recombinase are sequences incorporating mutations which cause recombination to be unidirectional, i.e., once recombination takes place, the sequence flanked by recombination sites can no longer be cleaved by means of a new recombination.

In a preferred embodiment, the first and second recognition sequences for a site-specific recombinase are heterospecific sequences and additionally incorporate mutations which cause recombination to be unidirectional.

In an even more preferred embodiment, the first and second LoxP sequences are selected from the group consisting of the pairs:
(a) SEQ ID NO: 9 and SEQ ID NO: 10,
(b) SEQ ID NO: 11 and SEQ ID NO: 12,
(c) SEQ ID NO: 9 and SEQ ID NO: 12,
(d) SEQ ID NO: 11 and SEQ ID NO: 10,
(e) SEQ ID NO: 10 and SEQ ID NO: 9,
(f) SEQ ID NO: 12 and SEQ ID NO: 11,
(g) SEQ ID NO: 10 and SEQ ID NO: 11, and
(h) SEQ ID NO: 12 and SEQ ID NO: 9.

In a particular embodiment, the gene of interest is a gene encoding a protein of interest or a precursor thereof. In a particular embodiment of the second vector of the invention, the protein of interest is a fluorescent protein, preferably green fluorescent protein or GFP. In another particular embodiment, the protein of interest is cardiotrophin-1. In another particular embodiment, the protein of interest is oncostatin-M. In another particular embodiment, the protein of interest is a single-chain antibody or an antibody heavy chain or light chain, preferably the A20 antibody heavy chain or light chain.

In a particular embodiment, the protein of interest additionally comprises a labeling sequence. The term "labeling sequence" has been described previously.

Second "In Vitro" Method for Generating a Cell Line Capable of Expressing a Gene of Interest The second vector of the invention can be used for substituting a first heterologous sequence, for example, a first gene of interest, in the cell of the invention with a second heterologous sequence, for example, a second gene of interest, by means of recombination. Therefore, in another aspect the invention relates to an in vitro method for generating a cell line capable of expressing a gene of interest, hereinafter second method of the invention, comprising the steps of:
- (i) introducing in the cell of the invention the second vector of the invention, wherein:
  - (a) said cell comprises a heterologous sequence in 3' position with respect to the replicon subgenomic promoter, wherein said heterologous sequence is a sequence of a gene of interest operatively bound to the subgenomic promoter, or an expression vector comprising said polynucleotide,
  - (b) the first recognition sequence of the polynucleotide comprising the alphavirus replicon complementary sequence is compatible with the first heterospecific recognition sequence of the vector,
  - (c) the second recognition sequence of the polynucleotide comprising the alphavirus replicon complementary sequence is compatible with the second heterospecific recognition sequence of the vector,
  - (d) the cell expresses a specific recombinase of said first and second recognition sequences, and
  - (e) the sequence necessary for replication of the alphavirus present in the vector coincides with the sequence necessary for replication of the alphavirus which is part of the alphaviral replicon,
- (ii) maintaining the cell in suitable conditions to allow substitution by means of site-specific recombination of the gene of interest which is part of the polynucleotide comprising the alphavirus replicon complementary sequence with the gene of interest which is part of the second vector of the invention, and
- (iii) selecting the cells in which substitution of the first gene of interest with the second gene of interest has occurred.

All the terms have been described above in relation to other aspects of the invention.

According to the second method of the invention, the cell expresses a recombinase specific for the recognition sequences present in the second vector of the invention and in the polynucleotide of the invention. The expression of said recombinase can be endogenous expression in the cell or can be achieved by introducing an exogenous recombinase in the cell, for example, incorporating a polynucleotide or vector comprising a sequence encoding said recombinase in the cell.

Methods for introducing polynucleotides or vectors in the cell have been described previously.

Step (ii) of the second method of the invention comprises maintaining the cells in suitable conditions to allow substitution by means of recombination of the gene of interest which is part of the polynucleotide comprising the alphavirus replicon complementary sequence with the gene of interest which is part of the second vector of the invention. Said conditions will vary depending on the type of cell and on the specific sequences, and can be determined by the person skilled in the art by means of routine experimentation. By way of illustration, said conditions comprise maintaining the cells in a suitable culture medium, which will vary depending on the cell type and is known by the person skilled in the art, for a time period comprised between 1 hour and 48 hours. The person skilled in the art knows how to determine if the substitution of the first heterologous sequence, for example the first gene of interest, with the second heterologous sequence, for example, the second gene of interest, has occurred. For example, it can be determined that the substitution has occurred correctly if the cell has acquired the resistance provided by the selection gene which is part of the second vector of the invention, provided that said selection gene is different from the selection gene which is part of the polynucleotide of the invention that was comprised in the cell. Additionally, it is also possible to determine that the substitution has occurred correctly by means of genomic DNA PCR, alphavirus vector RNA RT-PCR, or alternatively, if expression of the second gene of interest along with the loss of expression of the first gene of interest is detected in the cell by means of any of the methods listed above.

Step (iii) of the second method of the invention comprises selecting the cells in which substitution of the first gene of interest with the second gene of interest has occurred. Said selection can be carried out as explained above in relation to step (ii) of the first method of the invention. In a particular embodiment, the step of selecting cells in which substitution of the first gene of interest with the second gene of interest has occurred is carried out by means of selection by the selection gene which is part of the second vector of the invention, wherein said selection gene is different from that which is part of the polynucleotide comprising the alphavirus replicon complementary sequence. In an even more particular embodiment, the polynucleotide comprising the alphavirus replicon complementary sequence comprises a selection gene providing neomycin resistance, whereas the second vector of the invention, comprising the second gene interest, comprises a selection gene providing puromycin resistance; in this case, the selection of the cells in which the first gene of interest has been replaced with the second gene of interest is carried out by contacting said cells with puromycin.

In a particular embodiment, if the selection gene which is part of the second vector of the invention lacks a polyadenylation signal, then the cell comprises a polyadenylation signal in 3' position with respect to the second site-specific recombinase recognition sequence. Therefore, once the recombinase recognition sequences present in the second vector of the invention have recombined with the recognition sequences present in the cell, and therefore the first gene of interest, integrated in the cell genome, has been replaced with the second gene of interest present in the second vector of the invention, the selection gene which is part of said vector will be integrated in the cell in 5' position with respect to the polyadenylation signal which is in 3' position with respect to the second site-specific recombinase recognition sequence present in the cell, such that said second selection gene can be suitably expressed.

In a preferred embodiment, the recognition sequences for a site-specific recombinase are heterospecific sequences, i.e., they are different sequences that cannot recombine with one another in the presence of said recombinase.

In another preferred embodiment, the recognition sequences for a site-specific recombinase are sequences incorporating mutations which cause recombination to be unidirectional, i.e., once recombination takes place, the sequence flanked by recombination sites can no longer be cleaved by means of a new recombination.

In a preferred embodiment, the recognition sequences for a site-specific recombinase are heterospecific sequences and additionally incorporate mutations which cause recombination to be unidirectional.

In a preferred embodiment, the recognition sequences for a site-specific recombinase are heterospecific LoxP sequences and the site-specific recombinase is Cre recombinase.

In a particular embodiment,
- if the first recognition sequence which is part of the polynucleotide comprising the alphavirus replicon complementary sequence is the sequence SEQ ID NO: 9, then the second recognition sequence which is part of the vector is the sequence SEQ ID NO: 10; and if the first recognition sequence which is part of the polynucleotide comprising the alphavirus replicon complementary sequence is the sequence SEQ ID NO: 11, then the second recognition sequence which is part of the vector is the sequence SEQ ID NO: 12;
- if the first recognition sequence which is part of the polynucleotide comprising the alphavirus replicon complementary sequence is the sequence SEQ ID NO: 9, then the second recognition sequence which is part of the vector is the sequence SEQ ID NO: 12; and if the first recognition sequence which is part of the polynucleotide comprising the alphavirus replicon complementary sequence is the sequence SEQ ID NO: 11, then the second recognition sequence which is part of the vector is the sequence SEQ ID NO: 10;
- if the first recognition sequence which is part of the polynucleotide comprising the alphavirus replicon complementary sequence is the sequence SEQ ID NO: 10, then the second recognition sequence which is part of the vector is the sequence SEQ ID NO: 9; and if the first recognition sequence which is part of the polynucleotide comprising the alphavirus replicon complementary sequence is the sequence SEQ ID NO: 12, then the second recognition sequence which is part of the vector is the sequence SEQ ID NO: 11, and
- if the first recognition sequence which is part of the polynucleotide comprising the alphavirus replicon complementary sequence is the sequence SEQ ID NO: 10, then the second recognition sequence which is part of the vector is the sequence SEQ ID NO: 11; and if the first recognition sequence which is part of the polynucleotide comprising the alphavirus replicon complementary sequence is the sequence SEQ ID NO: 12, then the second recognition sequence which is part of the vector is the sequence SEQ ID NO: 9.

The invention is explained below by means of the following purely illustrative examples which in no way limit the invention.

EXAMPLES

Materials and Methods

Cell Culture

The BHK-21 cell line (ATCC: CCL-10) was cultured in Glasgow minimum essential medium (Glasgow-MEM, Gibco BRL, UK) supplemented with 5% fetal bovine serum (FBS), 10% tryptose phosphate broth (TPB), 2 mM glutamine, 20 mM HEPES, 100 µg/ml streptomycin and 100 IU/ml penicillin (complete BHK medium). The Huh7 and HepG2 cell lines (ATCC-HB8065) were incubated in Dulbecco's modified Eagle's medium (Invitrogen, Carlsbad, Calif.) supplemented with 10% FBS, 2 mM glutamine, 100 µg/ml streptomycin and 100 IU/ml penicillin. The BHK cells adapted to grow in suspension were cultured in SMEM culture medium (Sigma, St. Louis, Mo.) supplemented with 10% FBS, 10% TPB, 2 mM glutamine, 20 mM HEPES, 100 µg/ml streptomycin, 100 IU/ml penicillin and 0.1% pluronic acid F-68 (Gibco BRL, UK) (complete SMEM medium), or in EX-CELL™ CD CHO, supplemented with 10% TPB, 2 mM glutamine, 20 mM HEPES, 100 µg/ml streptomycin, 100 IU/ml penicillin and 0.1% pluronic acid F-68 (serum-free medium). Transfections were performed using Lipofectamine (Gibco BRL, Rockville, Md.) diluted in Opti-MEM® Reduced-Serum Medium (Gibco-BRL), following the supplier's instructions. For selecting the different stable cell lines, the culture medium was supplemented with hygromycin B (Invitrogen), neomycin (G418, Gibco BRL), or puromycin (Sigma, St. Louis, Mo.) at 250 µg/mL, 750 µg/mL and 5 µg/mL, respectively, added 24 h after transfection. For induction studies, adherent cells were seeded at a density of $5\times10^5$ cells/well in 6-well plates and incubated in the presence of DOX for 96-120 h. In the case of cells in suspension, DOX was added directly to a culture of $2.5\times10^5$ cells/mL and incubations in the presence of the inductor were performed for 10 days.

Plasmids

General Considerations

All PCR fragments were generated using Pfu or Pfu Turbo (Invitrogen) and the oligonucleotides indicated in Table 4. These fragments were purified using the Gel Extraction Kit (Quiagen), adenylated and cloned into the pGEM-T-easy vector (Promega), sequenced and finally sub-cloned into the indicated plasmids using the mentioned restriction sites.

TABLE 4

Oligonucleotides used for cloning and PCR reactions

| Oligo No. | Sequence identifier | 5'-3' orientation[a] | Sequence[b] | Restriction enzyme |
|---|---|---|---|---|
| 1 | SEQ ID NO: 17 | F | CCCGGGATGAAAAAG CCTGAACTCA | XmaI |
| 2 | SEQ ID NO: 18 | R | GCGGCCGCCTATTCC TTTGCCCTCGGAC | NotI |
| 3 | SEQ ID NO: 19 | F | ATGGCGGATGTGTGA CATACACG | - |
| 4 | SEQ ID NO: 20 | R | GCTCCTCGCCCTTGC TCACCATCGTGGGTG GTTAATCTCTCGCGT AG | - |
| 5 | SEQ ID NO: 21 | F | ATGGTGAGCAAGGGC GAGGA | - |
| 6 | SEQ ID NO: 22 | R | ACTAGTCTTAAGATA CATTGATGAGTTTGG | SpeI |
| 7 | SEQ ID NO: 23 | F | ATGCATCGCGATAGC GGTACCGAGCTCTTA CGCTCGAGT | NsiI-NruI |
| 8 | SEQ ID NO: 24 | R | GGTGGCAGGAGCTGG AACAAAATCTTTTGG CGTCGTGTATGTCAC ACATCCGCCATATCG TGTGTGCAGAAAGAC TCGCTC | - |
| 9 | SEQ ID NO: 25 | R | GGTGGCAGGAGCTGG AACAAAATCTTTTGG CGTCGTGTATGTCAC ACATCCGCCATGATC GTGTGTGCAGAAAGA CTCGCTC | - |
| 10 | SEQ ID NO: 26 | R | GGTGGCAGGAGCTGG AACAAAATCTTTTGG CGTCGTGTATGTCAC ACATCCGCCATATGT CGTGTGTGCAGAAAG ACTCGCTC | - |

TABLE 4-continued

Oligonucleotides used for cloning and PCR reactions

| Oligo No. | Sequence identifier | 5'-3' orientation[a] | Sequence[b] | Restriction enzyme |
|---|---|---|---|---|
| 11 | SEQ ID NO: 27 | F | AGAGCTC_GGCCGCCTCGGCC_TCTGA | SacI-SfiI |
| 12 | SEQ ID NO: 28 | R | ATGCATGGCGGTAATACGGTTA | NsiI |
| 13 | SEQ ID NO: 29 | F | ATGGCGGATGTGTGACATACACG | - |
| 14 | SEQ ID NO: 30 | R | GGGCCC_GATATC_CAAGATGAGTGTGTC | ApaI-EcoRV |
| 15 | SEQ ID NO: 31 | R | ACTAGTATAACTTCGTATAGTACACATTATACGAACGGTAGTGGGCGAAGAACTCCAGCATG | SpeI |
| 16 | SEQ ID NO: 32 | F | GGATCCATGGTGAGCAAGGGCGAGGAGC | BamHI |
| 17 | SEQ ID NO: 33 | R | CCCGGGATC_TTAATTAA_TTACTTGTACAGCTCGTCCATGCCGA | XmaI-PacI |
| 18 | SEQ ID NO: 34 | F | GATCTACCGTTCGTATAAAGTATCCTATACGAAGTTATC | - |
| 19 | SEQ ID NO: 35 | R | GATCGATAACTTCGTATAGGATACTTTATACGAACGGTA | - |
| 20 | SEQ ID NO: 36 | F | CATATGTACCGTTCGTATAAAGTATCCT | NdeI |
| 21 | SEQ ID NO: 37 | R | ACTAGTGCTATGGCAGGGCCTGCCGCCCG | SpeI |
| 22 | SEQ ID NO: 38 | F | GATATCGTGAGGCTCCGGTGCCCGTCAG | EcoRV |
| 23 | SEQ ID NO: 39 | R | GCGGCCGCTTCACGACACCTGAAATGGAAGAAAAAAACTTTGAA | NotI |
| 24 | SEQ ID NO: 40 | F | TATAACTTCGTATAAAGTATCCTATACGAACGGTATCTAGATCTCGCGAGCTCAGCCATATG | - |
| 25 | SEQ ID NO: 41 | R | TATGGCTGAGCTCGCGAGATCTAGATACCGTTCGTATAGGATACTTTATACGAAGTTAT | - |
| 26 | SEQ ID NO: 42 | F | CATATGTTAGGGTAGGCAATGGCATTGA | NdeI |
| 27 | SEQ ID NO: 43 | R | CAGCTGCTGGCTTAACTATGCGGCATC | PvuII |
| 28 | SEQ ID NO: 44 | F | CATGGGATCATAACTTCGTATAATGTGTACTATACGAACGGCCATG | - |
| 29 | SEQ ID NO: 45 | R | GATCCATGGCCGTTCGTATAGTACACATTATACGAAGTTATGATCC | - |
| 30 | SEQ ID NO: 46 | F | AGATCTGCACCATGGTGAGCAAGGGCGAGGA | BglII |
| 31 | SEQ ID NO: 47 | R | CATATGTTACTTGTACAGCTCGTCCATG | NdeI |
| 32 | SEQ ID NO: 48 | F | AGATCTGCACCATGTCGGCCCTGCTGATCCTGG | BglII |
| 33 | SEQ ID NO: 49 | R | CATATGTCAGGCCGAGCCCCGGGCAG | NdeI |
| 34 | SEQ ID NO: 50 | F | GGATCC_TCGCGA_GCACCATGTCGGCCCTGCTGATCCTGGCCCTGGTCGGAGCCGCCGTCGCCCACCACCACCACCACGCGGCTATAGGCAGCTGCTCG | BamHI-NruI |
| 35 | SEQ ID NO: 51 | R | GGATCCATATGCTATCTCCGGCTCCGGTTCGGGC | BamHI-NdeI |
| 36 | SEQ ID NO: 52 | F | CCTAGGGGACATTAAGGCGTTTAAG | - |
| 37 | SEQ ID NO: 53 | R | GTCCTCCTTGAAGTCGATGC | - |
| 38 | SEQ ID NO: 54 | R | CGACATGGTGCAGATCTAGA | - |
| 39 | SEQ ID NO: 55 | R | CCGTGTTTCAGTTAGCCTCCCCC | - |
| 40 | SEQ ID NO: 56 | F | TGCTCCTGCCGAGAAAGTAT | - |
| 41 | SEQ ID NO: 57 | F | AAGCTTCCGCCACGACCGGTGCCG | - |
| 42 | SEQ ID NO: 58 | F | CTGTTCTCGACGCGTCGTC | - |
| 43 | SEQ ID NO: 59 | R | GAGGTGTTTCCACGACCC | - |
| 44 | SEQ ID NO: 60 | F | GGGATGTTTGCTCCAACCAA | - |
| 45 | SEQ ID NO: 61 | R | GCGCTTTTGACTCAAGGATTTAA | - |
| 46 | SEQ ID NO: 62 | R | TGCTTGTCGGCCATGATATA | - |
| 47 | SEQ ID NO: 63 | R | GAACTTCAGGGTCAGCTTGC | - |
| 48 | SEQ ID NO: 64 | R | AACTTGTGGCCGTTTACGTC | - |

TABLE 4-continued

Oligonucleotides used for cloning and PCR reactions

| Oligo No. | Sequence identifier | 5'-3' orientation[a] | Sequence[b] | Restriction enzyme |
|---|---|---|---|---|
| 49 | SEQ ID NO: 65 | F | AGATCTCACCATGAAGTTGCCTGTTAGGCTG | BglII |
| 50 | SEQ ID NO: 66 | R | CCAATCTAGGACCGCCGTAGAGGTTTAACACTCATTCCTGTTGAAGCT | - |
| 51 | SEQ ID NO: 67 | F | ACCTCTACGGCGGTCCTAGATTGGTGCGTTAATACACAGAATTCTGATTGCACCATGGCATGGAACTTCATCATGGTC | - |
| 52 | SEQ ID NO: 68 | R | CATATGCTATTTACCCGGAGTCCGGGAG | NdeI |

Figure 1:
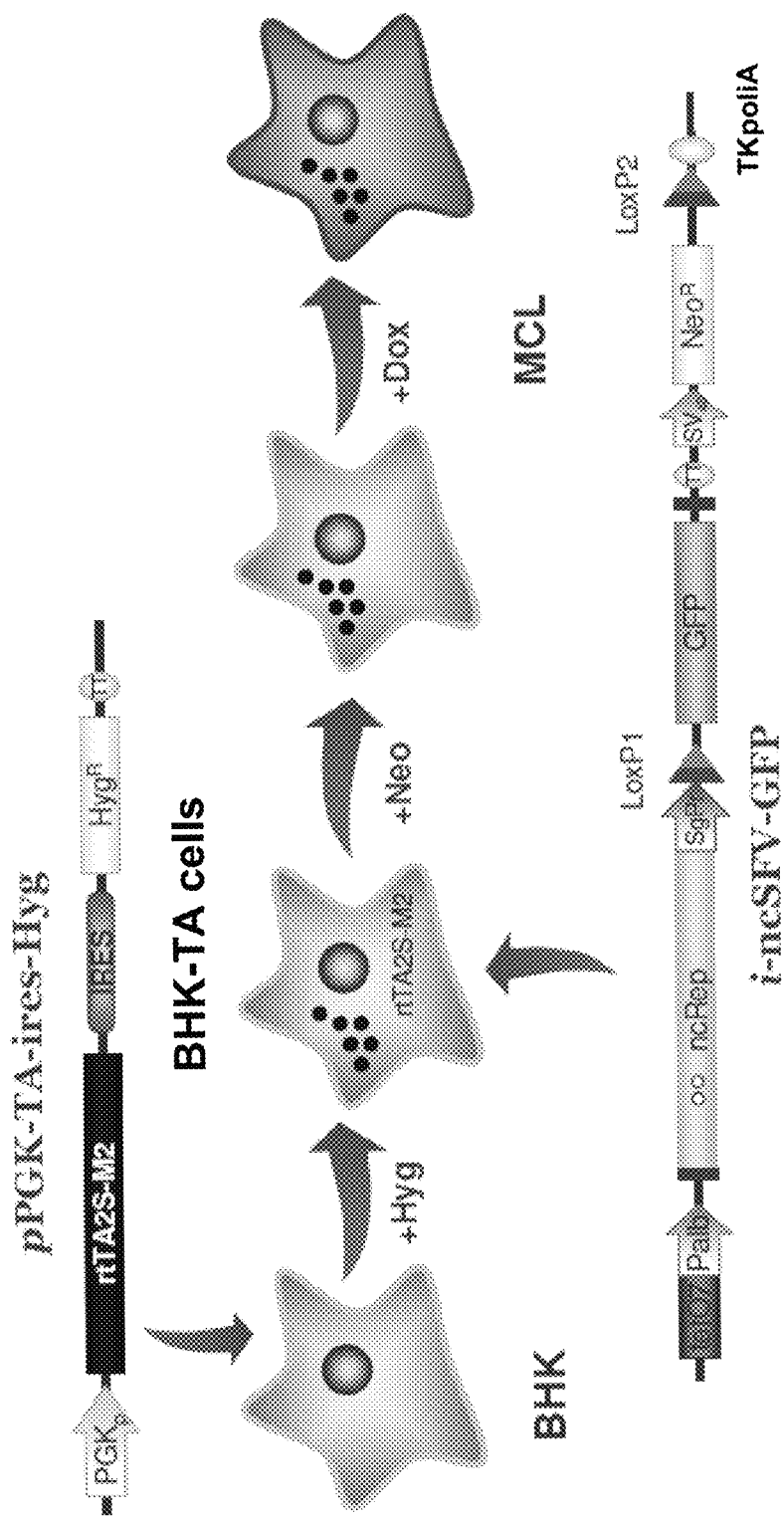
FIG. 1 shows the generation of a master cell line (MCL) providing an inducible non-cytopathic Semliki Forest Virus (SFV) vector expressing GFP. BHK cells were transfected with a plasmid constitutively expressing the rtTA2S-M2 transcriptional activator bound to the hygromycin resistance gene ($Hyg^R$) by means of an IRES sequence (pPGK-TA-ires-Hyg, top diagram). After selection with hygromycin, a selected clone was transfected with a plasmid containing the inducible non-cytopathic SFV vector expressing GFP (i-ncSFV-GFP) and a neomycin resistance gene ($Neo^R$) (bottom diagram). In this vector, the ncSFV sequence is under the transcriptional control of a minimal albumin promoter (Palb) fused with a tetracycline responsive element (tetO7), whereas the GFP sequence is located after the SFV subgenomic promoter (SgPr). Mutant LoxP sites were inserted into the 5' position of the GFP gene (LoxP1) and into the 3' position of the $Neo^R$ gene (LoxP2), respectively. The cells were selected with neomycin, cloned by means of terminal dilution and analyzed for determining their inducibility, GFP expression, and the absence of expression in induction-free conditions, obtaining the master line MCL. $PGK_p$, phosphoglycerate kinase promoter; ncRep, non-cytopathic SFV replicase; $SV_{40}$, simian virus 40 promoter (SV40); TT, SV40 polyadenylation and transcription termination sequence; TKpolyA, thymidine kinase gene polyadenylation and transcription termination sequence.

[a]F, forward (sense); R, reverse (antisense)
[b]The restriction sites indicated in the last column are in bold print, italics or underlined pPGK-TA-ires-Hyg The gene conferring hygromycin resistance was amplified by PCR with oligonucleotides 1 and 2 using the pTK-Hyg plasmid (Clontech) as a template and cloned into pIRES (Clontech) after the encephalomyocarditis virus (ECMV) internal ribosome entry site (IRES) using the Xma I and Not I restriction sites. The pIRES-Hyg vector was thereby generated. The gene encoding the rtTAs2M2 transactivator (Urlinger, Baron et al. 2000) was cloned under the transcriptional control of the PGK promoter and fused to the preceding construct containing the IRES-hygromycin cassette of the pIRES-Hyg plasmid using the Xho I and Mlu I sites to generate the pPGK-TA-ires-Hyg plasmid (FIG. 1).

piPalb-GFP

A crossover PCR was performed to fuse the first 85 nucleotides of the SFV 5' untranslated region (5"UTR) and the GFP gene. The first PCR was carried out using oligonucleotides 3 and 4 and the pSFV-1 plasmid as a template (Liljestrom and Garoff. 1991, Biotechnology (N AND). 1991 9:1356-61). The second PCR was performed with oligonucleotides 5 and 6 using the pCMV-GFP plasmid (Clontech) as a template. The fragments resulting from both reactions were purified, mixed in equimolar amounts and used as a template for the crossover PCR with oligonucleotides 3 and 6, to obtain a 1057 base pair (bp) fragment containing the SFV 5'UTR region, GFP and SV40 polyadenylation signal (5'-UTR-SFV-GFP-SV40PolyA fragment). A new crossover PCR was performed to place this fragment under the transcriptional control of tetO7-pAlb promoters of different lengths. First, fragments containing the different promoters were generated using oligonucleotide 7 in combination with oligonucleotides 8, 9 and 10, using the AAV8-Tet$_{bidir}$-Alb-CMV$_m$-luc plasmid as a template (Vanrell et al. 2011. Mol Ther. 19:1245-53). The crossover PCRs were performed using oligonucleotides 6 and 7 and these fragments as a template along with the 5'-UTR-SFV-GFP-SV40PolyA. The fragments thus obtained were cloned into pGEM-T-easy, generating plasmids piPalb-172-GFP, piPalb-173-GFP and piPalb-174-GFP, containing the SFV 5'UTR sequence located at nucleotides 172, 173 and 174 of the start of the minimal albumin promoter, respectively, followed by the GFP gene and the polyadenylation signal. On the other hand, in these constructs the GFP gene is located in the start position of the SFV replicase open reading frame.

i-ncSFV-GFP

A 2078 bp fragment containing the gene conferring neomycin resistance, followed by the thymidine kinase polyadenylation signal and the origin of replication pUC (neo-polyA-ori), was first generated by PCR using oligonucleotides 11 and 12 and pSFV-1 as a template. This fragment was cloned into pGEM-T-easy and referred to as pGEM-A1. On the other hand, fusion between the tetO7-Palb promoter containing the first 174 bp of the minimal albumin promoter and the SFV 5' fragment including the first 280 nucleotides of the replicon was generated by crossover PCR. The first PCR was performed with oligonucleotides 7 and 10 using the piPalb-174-GFP plasmid as a template. The second PCR was carried out with oligonucleotides 13 and 14 on the pSFV-1 plasmid. The two fragments were purified, mixed and used as a template for crossover PCR, with oligonucleotides 7 and 14. The PCR product was digested with Nsi I and EcoR V, and the 796 bp fragment obtained was subcloned into pGEM-A1, digested with the same enzymes, to generate the pGEM-A2 plasmid in which the tetO7-Palb-5"UTR-SFV sequence was bound to the neo-polyA-ori sequence. pGEM-A2 was digested with Sfi I and EcoR V, and the 2874 bp fragment was subcloned into the same sites of the pBK-T-ncSFV-1 plasmid, derived from pBK-T-SFV-1 (Berglund et al. 1998. Nat Biotechnol. 16:562-5) containing the mutations P718T and R649H in the replicase nsp2 subunit (Casales et al. 2008. Virology. 376: 242-51). The i-nSFV vector was thereby generated in which the complete sequence of the non-cytopathic SFV replicon is under the transcriptional control of the inducible tetO7-Palb promoter and is followed by the gene conferring neomycin resistance under the control of the SV40 promoter. In order to introduce the LoxP2 site (see Table 2), a 1103 bp fragment including this sequence was generated by PCR using oligonucleotides 11 and 15 and the pSFV-1 plasmid as a template. This fragment was digested with Spe I and Avr II and subcloned between the two Avr II sites of the i-ncSFV plasmid. On the other hand, a fragment containing the GFP gene was generated by PCR using oligonucleotides 16 and 17 and pCMV-GFP as a template. This fragment was subcloned into the BamH I and Xma I sites of the i-ncSFV plasmid after the SFV subgenomic promoter. Finally, the LoxP1 site (see Table 2) was synthetically produced by hybridization of oligonucleotides 18 and 19 and inserted into the BamHI site to generate the i-nsSFV-GFP vector.

TABLE 2

Wild-type and mutant LoxP sequences

| LoxP site | Sequence | Sequence identifier |
|---|---|---|
| wt | ATAACTTCGTATAATGTATGCTATACGAAGTTAT | SEQ ID NO: 69 |
| 1[a] | TACCGTTCGTATAAAGTATCCTATACGAAGTTAT | SEQ ID NO: 9 |
| 2[b] | TACCGTTCGTATAATGTGTACTATACGAAGTTAT | SEQ ID NO: 10 |

TABLE 2-continued

Wild-type and mutant LoxP sequences

| LoxP site | Sequence | Sequence identifier |
|---|---|---|
| 3[c] | ATAACTTCGTATAAAGT ATCCTATACGAACGGTA | SEQ ID NO: 11 |
| 4[d] | ATAACTTCGTATAATGT GTACTATACGAACGGTA | SEQ ID NO: 12 |

[a]The LoxP1 site includes mutations 62a (Arakawa et al, 2001, supra), in bold, and mutations 2272, underlined (Lee and Saito, 1991, supra).
[b]The LoxP2 site includes mutations 62a, in bold, and mutation 5171, underlined (Lee and Saito, 2001, supra).
[c]The LoxP3 site contains mutation 62b, in bold (Arakawa et al, 2001, supra) and mutation 2272, underlined.
[d]The LoxP4 site contains mutation 62b, in bold, and mutation 5171, underlined.

iGFP

The i-ncSFV-GFP vector was digested with Pac I and Spe I to eliminate the SFV 3'UTR sequence, treated with Klenow and DNA polymerase T4 to generate blunt ends and re-ligated with T4 DNA ligase. Using this construct, a 3687 bp fragment containing LoxP1-GFP-SV40PolyA-SV40Prom-neo-LoxP2-TK-PolyA sequences was generated by PCR using oligonucleotides 20 and 21. The fragment thus generated was subcloned into the piPalb174-GFP vector between the Nde I and Spe I sites.

pShuttle-SFV Plasmids

The EF1a promoter (EF1aP) was amplified by PCR using oligonucleotides 22 and 23 and from the AAV-Luc plasmid (Berraondo et al. 2005. Mol. Ther. 12:68-76), obtaining a 1182 bp fragment which was subcloned into the pBS-pac plasmid (de la Luna et al. 1988. Gene, 62:121-6) in the EcoR V and Not I sites. The pBS-EF1aP-pac plasmid was thereby generated, in which expression of pac is directed by EF1aP. The LoxP3 sequence (see Table 2) followed by a multiple cloning site containing Bgl I, Nru I, Sac I, Blp I and Nde I restriction sites was generated by hybridization of oligonucleotides 24 and 25, and the 62-bp synthetic fragment obtained was introduced in pBS-EF1aP-pac before the EF1aP-pac sequence using the Nde I site, and thereby generating the pBS-LoxP3-MCS-EF1aP-pac plasmid. The fragment containing the SFV 3'UTR sequence and the SV40 polyadenylation signal was amplified by PCR using oligonucleotides 26 and 27 and pSFV-1 as a template, and subcloned between the Nde I and Pvu II sites of pBS-LoxP3-MCS-EF1aP-pac. The SV40 polyadenylation signal present at the end of the pac sequence (present in pBS-pac and different from that found after the SFV 3'UTR sequence) was removed by digestion with Nco I and BamH I, followed by introduction of the LoxP4 site (see Table 2) using the synthetic dimer obtained by hybridization of oligonucleotides 28 and 29. The sequence of the SV40 promoter present in the pBS-pac vector was removed by digestion with EcoR V and Pvu II followed by plasmid re-ligation, to finally obtain the pShuttle-SFV vector. pShuttle-SFV-Tomato was generated by inserting the Tomato gene, previously amplified from the pCAG-tdTOMATO-IRES-neo plasmid, kindly donated by Dr. Beatriz Pelacho (CIMA, Pamplona), using oligonucleotides 30 and 31, into the Bgl II and Nde I sites of the pShuttle-SFV. To generate the pShuttle-SFV-CT vector, the CT-1 gene was amplified using the ncSFV-CT1 vector (Casales et al. 2010. N Biotechnol. 27:138-48) and oligonucleotides 32 and 33, and the fragment obtained was inserted into the Bgl II and Nde I sites of the pShuttle-SFV vector. pShuttle-SFV-OSM was generated by amplifying the OSM gene from a plasmid containing the sequence of human oncostatin M (pCR2.1topo-hOSM, kindly donated by Dr. Esther Larrea, CIMA) using oligonucleotides 34 and 35. The 671 bp fragment obtained was inserted into the Nru I and Nde I sites of the pShuttle-SFV. In this construct, the last 31 OSM amino acids were removed to obtain the mature form of the protein, and the OSM signal peptide (the first 25 amino acids) were replaced with the preprotrypsin signal peptide, to achieve optimum secretion. On the other hand, a sequence encoding six histidines was included between the signal peptide and the amino terminal end of the mature OSM.

To obtain the pShuttle-SFV-A20 vector, the A20 antibody light and heavy chain genes were amplified from cDNA obtained by reverse transcription of the total RNA of A20 cells (ATCC TIB-208). A crossover PCR was performed to insert a subgenomic promoter between both chains. The first PCR was performed with oligonucleotides 49 and 50. The second PCR was performed with oligonucleotides 51 and 52. The fragments resulting from both fractions were purified, mixed in equimolar amounts and used as a template for the crossover PCR with oligonucleotides 49 and 52, to obtain a 2191 bp fragment containing the light chain, a subgenomic promoter and the heavy chain. This fragment was digested with Bgl II and Nde I and cloned into pShuttle-SFV using the same restriction sites.

Cell Cloning by Limit Dilution

The cells were trypsinized, washed, resuspended in complete BHK medium at a final concentration of 5 cells/mL, distributed in 96-well plates by adding 100 μL per well and incubated for a maximum of four weeks, changing the culture medium every week. After at least two weeks of incubation, wells containing a single colony were trypsinized, resuspended in medium and sequentially expanded in 24-well plates, 6-well plates, 25 cm$^2$ and 75 cm$^2$ culture bottles. The selected clones were frozen in freezing medium (10% DMSO in FBS) and stored in liquid nitrogen. An average of 20 clones were selected from each parental culture.

RT-PCR Analysis

About 10$^6$ cells were collected and the total RNA was purified with TRI-Reagent (SIGMA) following the supplier's instructions. The RNA was reverse transcribed to cDNA using oligonucleotides with random sequences (Promega) and SuperScript III RT (Invitrogen, Carlsbad, Calif.). Quantitative RT-PCR was carried out using Power SYBR® Green PCR Master Mix (Biorad, Hercules Calif.) and combinations of specific oligonucleotides. Oligonucleotides 36 and 37 were used for detecting SFV RNAs encoding GFP, whereas molecules encoding CT-1 and OSM were detected with oligonucleotide 36 in combination with oligonucleotides 38 and 35, respectively. On the other hand, the correct exchange between the neomycin and puromycin genes was evaluated by combining an oligonucleotide specific for the TK-PolyA sequence (Oligonucleotide 39) with oligonucleotides 40 and 41, respectively. The replicase was detected using oligonucleotides 42 and 43. The values were normalized by comparison with actin expression using oligonucleotides 44 and 45.

RNA Stability Analysis

Total RNA was purified from several passes (between passes 5 and 25) of the MCL line after incubating each pass for 120 h with 1.25 μg/mL of DOX. The RNA was purified with TRI-Reagent (SIGMA) and reverse transcribed to cDNA as described above. These cDNAs were used as a template for amplifying a fragment corresponding to the GFP gene using high-fidelity DNA polymerase Pfu (Stratagene, Cedar Creek, Tex.) and oligonucleotides 16 and 17. The fragments obtained were purified, adenylated and cloned into pGEM-T-easy. An average of 21.5 clones was sequenced per pass in each cell line using the 3130×1 Genetic Analyzer (Applied Biosystems, Foster City, Calif.). To determine the mutation rate, the sequences of all the clones were compared with the sequence of the GFP gene in the original vector using the ClustalX program.

Cre Recombinase-Mediated Transgene Exchange

The MCL was seeded in 6-well plates at a density of $0.5 \times 10^6$ cells/well in complete BHK medium without selection antibiotics. After 24 h, the cells were transfected with 0.5-4 μg of the pShuttle-SFV plasmid containing the gene of interest, mixed with 1 μg of pBS185CMV-Cre (Sauer and Henderson, 1990. New Biol 2: 441-9). The next day, the cells were incubated with complete BHK medium supplemented with 5 μg/mL of puromycin and cells resistant to said antibiotic were selected, changing the medium every three days. The cells were cultured to confluence and expanded. These parental cultures were induced with DOX to verify heterologous protein expression, and the cultures with the best expression were cloned by limit dilution and expanded.

Heterologous Protein Expression Analysis

Cell lysates were obtained by incubating the cells with a solution made up of 1% Igepal (Sigma), 50 mM Tris-HCl pH 7.6, 150 mM NaCl, 2 mM EDTA and 1 μg/ml of phenylmethylsulfonyl fluoride (PMSF, Sigma). After 10 minutes at 4°, the samples were centrifuged for 6 minutes at 6000 rpm in a cooled centrifuge. For Western Blot experiments, the supernatants and cell lysates expressing the heterologous proteins were analyzed by SDS-PAGE in 12% polyacrylamide gels, transferred to nitrocellulose membranes and incubated with suitable primary antibodies: anti-GFP polyclonal rabbit serum (Abcam, Cambridge, UK), anti-actin polyclonal rabbit serum (Sigma), or anti-SFV nsp2 polyclonal rabbit serum (Casales et al. 2008 Virology. 376:242-51), human CT-1-specific biotinylated polyclonal goat serum (R&D, Minneapolis, Minn.), or a human OSM-specific monoclonal murine antibody (R&D). On the other hand, a peroxidase-conjugated anti-rabbit IgG antiserum obtained in goat (Pierce Biotechnology, Rockford, Ill.), a streptavidin-peroxidase polymer (Sigma) and a peroxidase-conjugated anti-mouse IgG antiserum obtained in goat (Pierce Biotechnology) were used as secondary antibodies, respectively. In all cases, the proteins were visualized using the Western Lightning Chemiluminescence Reagent Plus (PerkinElmer Life Sciences, Waltham, Mass.). The recombinant GFP protein (Cell Biolabs, Inc., CA, USA), recombinant human OSM protein and CT-1 protein (R&D) produced in E. coli were used as controls. The amounts of CT-1 and OSM present in the supernatants of the stable lines were quantified by ELISAs specific for human CT-1 (ELISA Pair Set Kit RHF650CK, BioSupply UK) and human OSM (DSL-10-9400 Active Free, DSL, Webster, Tex.), respectively.

Analysis of the Biological Activity of CT-1 and OSM

To evaluate the activity of human CT-1, HepG2 cells were cultured in 12-well plates at a density of $2 \times 10^5$ cells per well for 24 h with 10% FBS and another 48 h in the absence of FBS. Different amounts of CT-1 produced by the stable lines or of commercial recombinant CT-1 were added at that time as a positive control. After 30 minutes, cell lysates were obtained and analyzed by Western Blot using phosphorylated STAT3-specific rabbit antiserum (Cell signaling, Danvers, Mass.) and actin-specific rabbit antiserum, using a peroxidase-conjugated anti-rabbit IgG sheep antiserum (Pierce Biotechnology, Rockford, Ill.) as a secondary antibody in both cases. The same type of test was used to evaluate the activity of OSM, incubating Huh7 cells for 24 h in the presence of 10% FBS, eliminating the serum for another 48 h and adding different amounts of human OSM produced from stable lines, or of commercial recombinant human OSM as a positive control. After 60 minutes of incubation, the lysates were analyzed by Western Blot with phosphorylated STAT3-specific antiserum and actin-specific antiserum. The proteins were visualized using the Western Lightning Chemiluminescence Reagent Plus, scanned with ImageQuant ECL imager (GE Healthcare, Chalfont St. Giles, UK) and quantified with the ImageQuant TL software program (GE Healthcare, Chalfont St. Giles, UK). The degree of STAT3 phosphorylation was calculated as the ratio between phosphorylated STAT3 and total protein. CT-1 and OSM activities were determined by means of interpolating these ratios in a standard curve generated with the ratios obtained with different amounts of the corresponding commercial human recombinant protein. The specific activity was calculated by dividing the amount of protein corresponding to the observed activity (according to the standard curve) by the actual amount of protein present in each sample, determined by ELISA. The STAT3 phosphorylation fraction produced per 1 ng of commercial recombinant protein was considered as 1 arbitrary unit (AU).

Purification and Biochemical Characterization of CT-1 and OSM

The selected clones expressing CT-1 and OSM were incubated at 33° C. with complete BHK medium supplemented with 1.25 μg/mL of DOX for 96 or 72 h, respectively. Then, the culture medium was replaced with EX-CELL CHO medium for 24 h. The culture medium was collected and centrifuged at 1000 g for minutes. CT-1 and OSM proteins were purified by pseudoaffinity chromatography using a $Ni^{2+}$-nitrilotriacetic column (QIAGEN, Germany) following the supplier's instructions and eluded with 125 mM imidazole, in an ÄKTA Explorer. The presence of recombinant protein was analyzed in each purification step through SDS-PAGE in 12% polyacrylamide gels, followed by silver staining or Western Blot. The bands of interest were digested in gel with trypsin, and identification of the proteins was obtained by analyzing digestion fragments in liquid chromatography and tandem mass spectrometry (LC-MS/MS).

Adaptation of Adherent Cells to Cultures in Suspension

The cultures in suspension were started by trypsinizing adherent cells and resuspending them in complete SMEM medium at a density of $2.5 \times 10^5$ cells/mL. The cells were incubated at 37° in bottles under continuous stirring at 100 rpm and diluted with fresh medium every four days until reaching the initial density. The growth rate and cell viability of the culture were monitored daily for the first three weeks of culture. Once the growth of the culture in suspension was stable, the serum was progressively removed reducing its concentration in each pass by 50%. For this purpose, in each pass the medium was mixed with serum-free medium until the final serum concentration was 0.5%, at which time the cells were washed and grown in serum-free medium.

Figure 2:
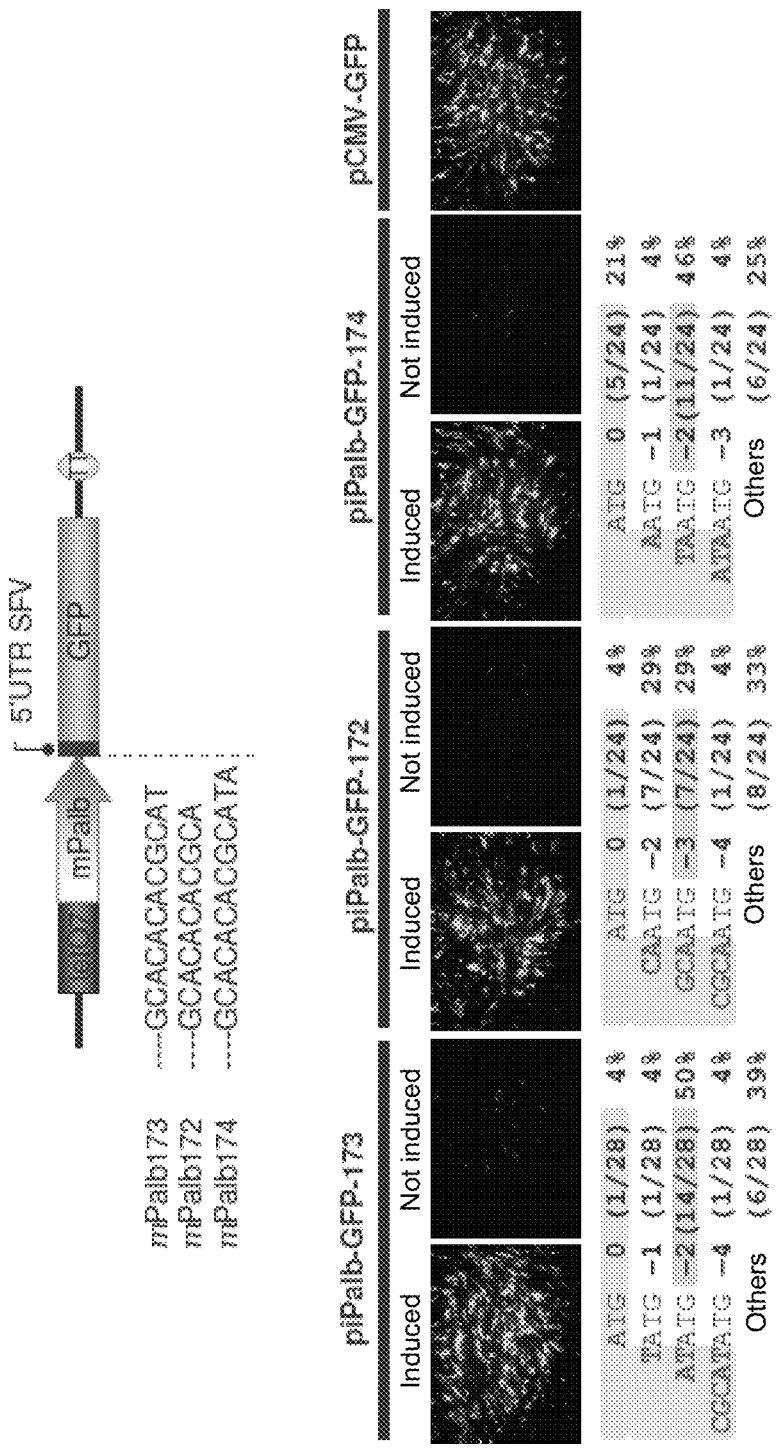
FIG. 2 shows the determination of the transcription start site from the inducible minimal albumin promoter. To accurately determine the nucleotide where transcription from the tetO7-pAlb promoter starts, the "5' RACE System for Rapid Amplification of cDNA Ends" (Invitrogen, Carlsbad, Calif.) kit was used. Briefly, plasmids piPalb-GFP-172, -173 and -174 were constructed as described in Materials and Methods and co-transfected with a plasmid expressing the rtTA2sM2 transcriptional activator under the control of the PGK constitutive promoter (PGK-rtTA-pA60, kindly donated by Dr. Rubén Hernandez-Alcoceba, CIMA, Pamplona). After 24 h of induction with 2 μg/mL doxycycline (DOX), total cellular RNA was isolated and the first cDNA strand was synthesized using oligonucleotide 42 (Table 4). The template RNA as well as the non-incorporated dNTPs, the oligonucleotide and proteins were removed and a polyC tag was added to the 3' end of the cDNA using terminal deoxynucleotidyl transferase and dCTP. This cDNA was amplified by means of PCR with Taq DNA polymerase, using a nested oligonucleotide (oligonucleotide 46) and a deoxyinosine oligonucleotide supplied with the kit. The PCR was diluted 10 times and used as a template for two consecutive nested PCRs using the "Universal Amplification primer" (supplied with the kit) and the oligonucleotides of sequence SEQ ID NO: 63 and SEQ ID NO: 64 (oligonucleotides 47 and 48). After amplifications, a single band which was cloned into the pGEM-T-easy vector (Promega) was obtained. Several clones of each construct were sequenced, and the 5' end was determined for each of them. The sequences above the photographs indicate the 3' end of the minimal promoter pAlb (mpAlb). The sequences under the photographs indicate the nucleotides of the 3' end of Palb (in bold) and the nucleotides of the 5' end of SFV (ATG) which were present at the 5' end of the transcribed RNAs. The first number indicates the start of transcription with respect to the first SFV nucleotide. In parenthesis: total number of clones starting in position 1 of SFV/total number of sequenced clones, followed by the percentage of clones starting in the first SFV nucleotide. pCMV-GFP, plasmid containing the GFP sequence after the CMV promoter, used as a control (Clontech). TT, SV40 polyadenylation and transcription termination sequence.

Example 1: Generation of a Stable Cell Line Containing an Inducible Non-Cytopathic Vector of the Semliki Forest Virus (SFV) Expressing GFP A stable cell line with an inducible non-cytopathic replicon of the SFV expressing GFP (i-ncSFV-GFP) was generated. To that end, BHK cells were transfected in a first step with a plasmid containing the rtTA2sM2 transactivator gene (TA) (Urlinger, Baron et al. 2000, Proc Natl Acad Sci USA, 97(14): 7963-8) after the PGK constitutive promoter, followed by an IRES sequence and the gene conferring hygromycin resistance (pPGK-TA-ires-Hyg, FIG. 1). After selecting with hygromycin, the BHK-TA cell line was obtained, which in the presence of doxycycline (DOX) was capable of transactivating the expression of genes that are under the control of a tetracycline responsive element (TRE). In a second step, the BHK-TA cells were transfected with a plasmid containing the cDNA sequence of the ncSFV-GFP vector under the transcriptional control of the minimal albumin promoter (Palb) fused to TRE (tetO$_7$) (see Materials and Methods). This plasmid also carries a neomycin resistance gene after the SV40 promoter (FIG. 1). The 5' end of ncSFV was cloned exactly into position 174 of Palb, since it was observed in an unexpected manner that the latter was the position in which transcription from this promoter started (FIG. 2). It is very important for transcription to start exactly at the 5' end of SFV so that the RNA of this vector can be replicated (Berglund et al. 1998, Nat. Biotechnol. 16:562-5). Several clones were isolated after selecting with neomycin by means of terminal dilution, and GFP expression with and without DOX was analyzed, the clone having the desired inducibility characteristics being selected: GFP expression in >80% of the cells when DOX is added and total absence of GFP expression when DOX is not added. This clone was expanded and referred to as master cell line (MCL).

Figure 4:
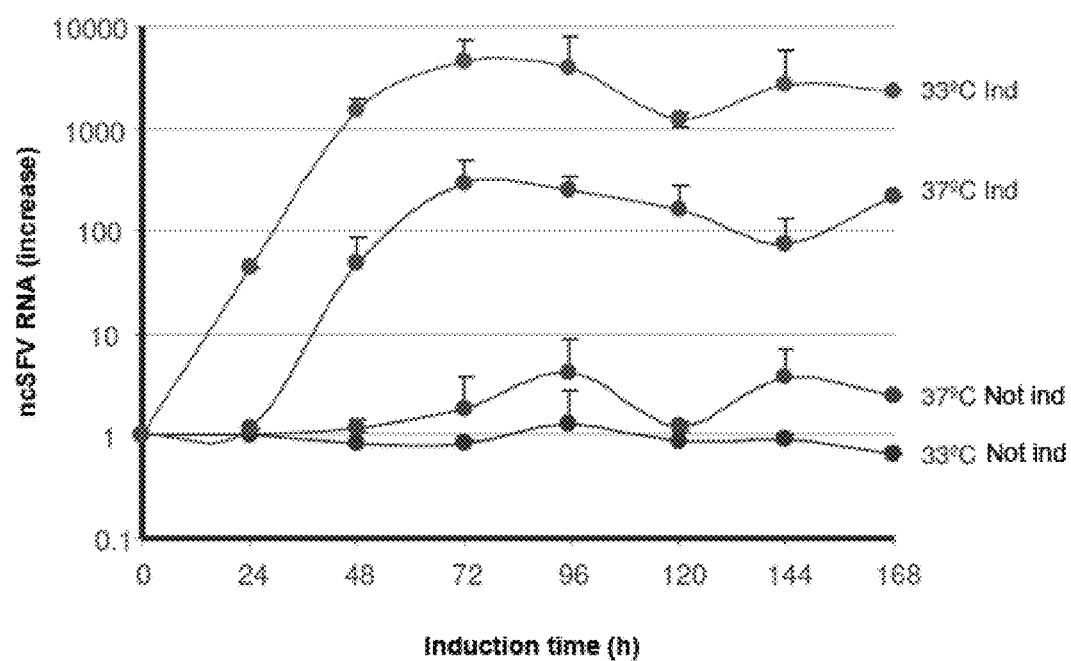
FIG. 4 shows the kinetics of SFV replication. The total RNA of the MCL incubated at 33° or 37° was extracted with or without DOX at 1.25 µg/mL DOX for the indicated times. ncSFV-GFP RNA levels were determined by means of real time RT-PCR as described in Materials and Methods. Ind., induced; Not ind, Not induced.

Example 2: MCL Characterization: Induction Kinetics, Optimum Temperature and Stability SFV replicase and GFP expression was monitored after the addition of DOX (2.5 µg/mL) at 33° and 37°, respectively. After 24 h at 33°, cells expressing GFP started to be seen, forming up to 90% of all cells after 96 h (FIGS. 3A and 3B). Surprisingly, induction at 37° only gave rise to a maximum of 40-50% of cells positive for GFP. GFP expression analysis by Western blot showed similar kinetics (FIG. 3C). Replicase induction was faster, reaching a maximum after 24 h at 33°, and being almost undetectable at 37° (FIG. 3C). ncSFV-GFP RNA levels reached a maximum after 72 h of incubation with DOX, although the levels were 10 times greater at 33° than at 37° (FIG. 4). Different DOX concentrations were tested at different times in order to optimize MCL induction. The maximum GFP induction was obtained with ≥0.3 µg DOX/mL incubating ≥96 h (FIG. 3D). Therefore, 1.25 µg DOX/mL for 96 h was always used in subsequent experiments. To evaluate MCL stability, this cell line was passed 50 times for 5 months in the presence or absence of the antibiotics used for selection thereof (hygromycin and neomycin). In each pass, cells were incubated with or without DOX, and the percentage of cells expressing GFP was analyzed by FACS. After 50 passes, 80-90% of the cells expressed GFP when DOX is added, indicating high MCL stability (FIG. 5A). This stability was confirmed by means of Western blot (FIG. 5B). The fact that there were no differences between growing the MCL in the presence or absence of hygromycin/neomycin indicated that this line could be maintained without selection.

GFP cDNAs were obtained after the induction in several steps in order to analyze genetic MCL stability. A mean of 21.5 clones/pass was sequenced in each of the two lines (maintained with or without hygromycin/neomycin). In each clone, 660 nucleotides corresponding to the GFP gene were sequenced, which translates into 14190 sequenced nucleotides/pass and 113500 total nucleotides. In this analysis, very few mutations were detected in the GFP sequence, a total mutation frequency of $1 \times 10^{-4}$ being determined, which is less than the mutation rate described for high-fidelity DNA polymerase used for amplifying cDNA (Table 1). Likewise, this mutation rate was less than that described in stable lines generated with the ncSFV RNA vector (Casales, Aranda et al., 2010, New Biotechnology 27(2): 138-148).

TABLE 1

Genetic stability of the GFP RNA in MCL

| Pass | Hyg/Neo | Mutated sequences[a] | Mutations[b] | Mutation rate[c] |
|---|---|---|---|---|
| 5 | + | 17% (4/24) | 4 | $2.6 \times 10^{-4}$ |
| 15 | + | 0% (0/17) | 0 | $<9.0 \times 10^{-5}$ |
| 20 | + | 0% (0/23) | 0 | $<6.6 \times 10^{-5}$ |
| 25 | + | 4% (1/24) | 3 | $1.9 \times 10^{-4}$ |
| 5 | − | 0% (0/21) | 0 | $<7.3 \times 10^{-5}$ |
| 10 | − | 13% (2/16) | 2 | $1.8 \times 10^{-4}$ |
| 17 | − | 4% (1/23) | 1 | $6.7 \times 10^{-5}$ |
| 23 | − | 8% (1/24) | 2 | $1.3 \times 10^{-4}$ |

[a]Percentage of mutated clones (%). In parenthesis: number of mutated clones/total number of analyzed clones.
[b]Total number of nucleotide changes in all the clones analyzed in each pass.
[c]The mutation rate was calculated by dividing the number of nucleotide changes in each pass by the total number of sequenced base pairs.

Example 3: Comparison of MCL with a Conventional Inducible Cell Line

Figure 6:
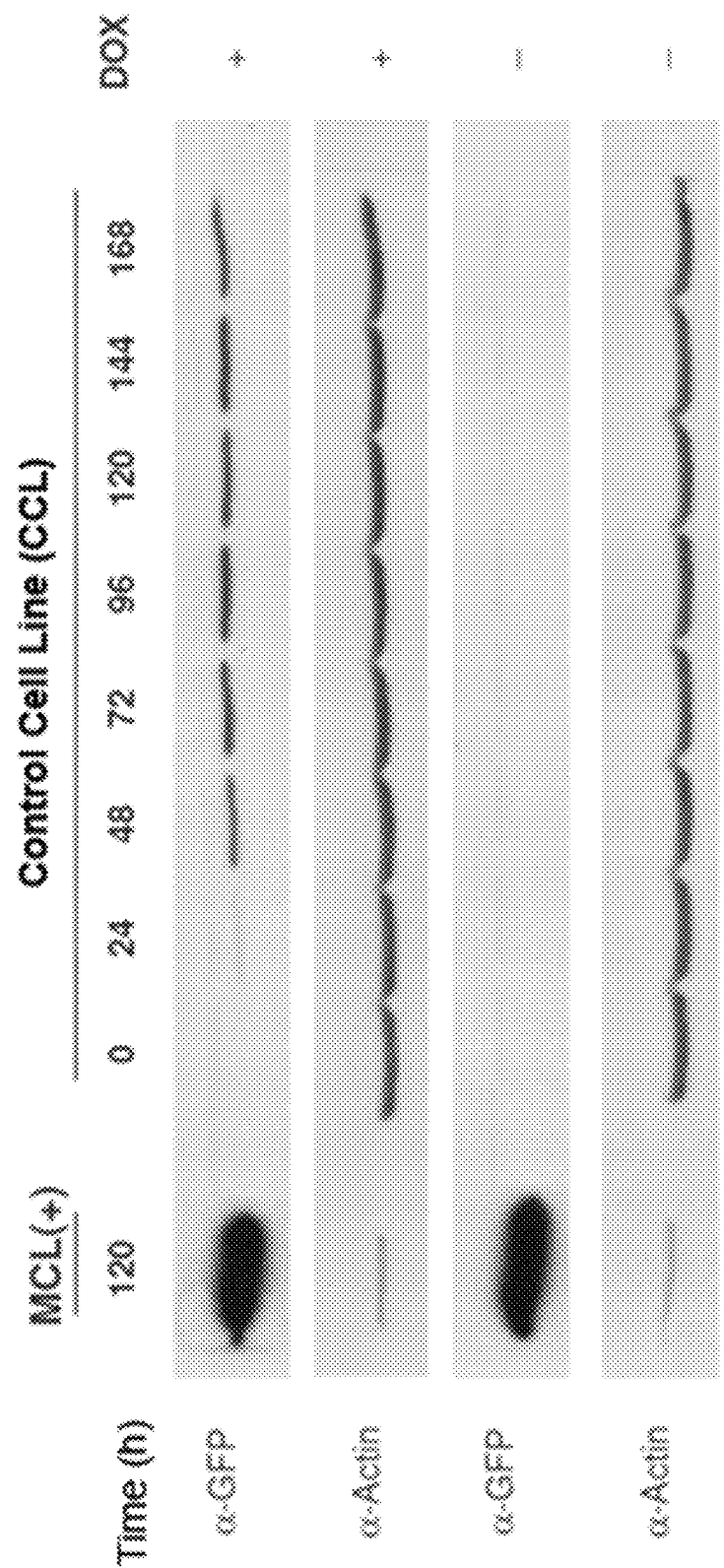
FIG. 6 shows the kinetics of GFP expression in a conventional inducible line. A BHK line constitutively expressing the rtTA2S-M2 transactivator and containing the GFP gene was obtained after the transcriptional control of the tetO7-PAlb promoter, and the cells were treated with 2 µg/mL DOX or without DOX at 33° C. The cell lysates were analyzed at the indicated times by means of Western blot using an anti-GFP and anti-actin antibody. MCL(+), MCL incubated for 5 days with DOX.

Transgene expression in the MCL line is due to self-replication of the RNA vector, which should lead to greater expression levels than those obtained with a conventional cell line. To verify this, a conventional inducible cell line was generated by means of transfecting BHK-TA cells with a plasmid containing the GFP gene under the transcriptional control of the tetO$_7$-PAlb promoter (iGFP) and the neomycin resistance gene. After selecting the cells with this last antibiotic, several clones were isolated by means of terminal dilution and GFP expression with and without DOX was analyzed. An optimal clone was chosen in which, after addition of DOX, up to 90% of the cells expressing GFP could be detected after 96 h and in which there was no detectable GFP expression in the absence of DOX. GFP expression in this control line was also confirmed by Western blot (FIG. 6). Noticeably, GFP expression levels after 96 h of induction were lower in the control line than those obtained with the MCL.

Figure 7:
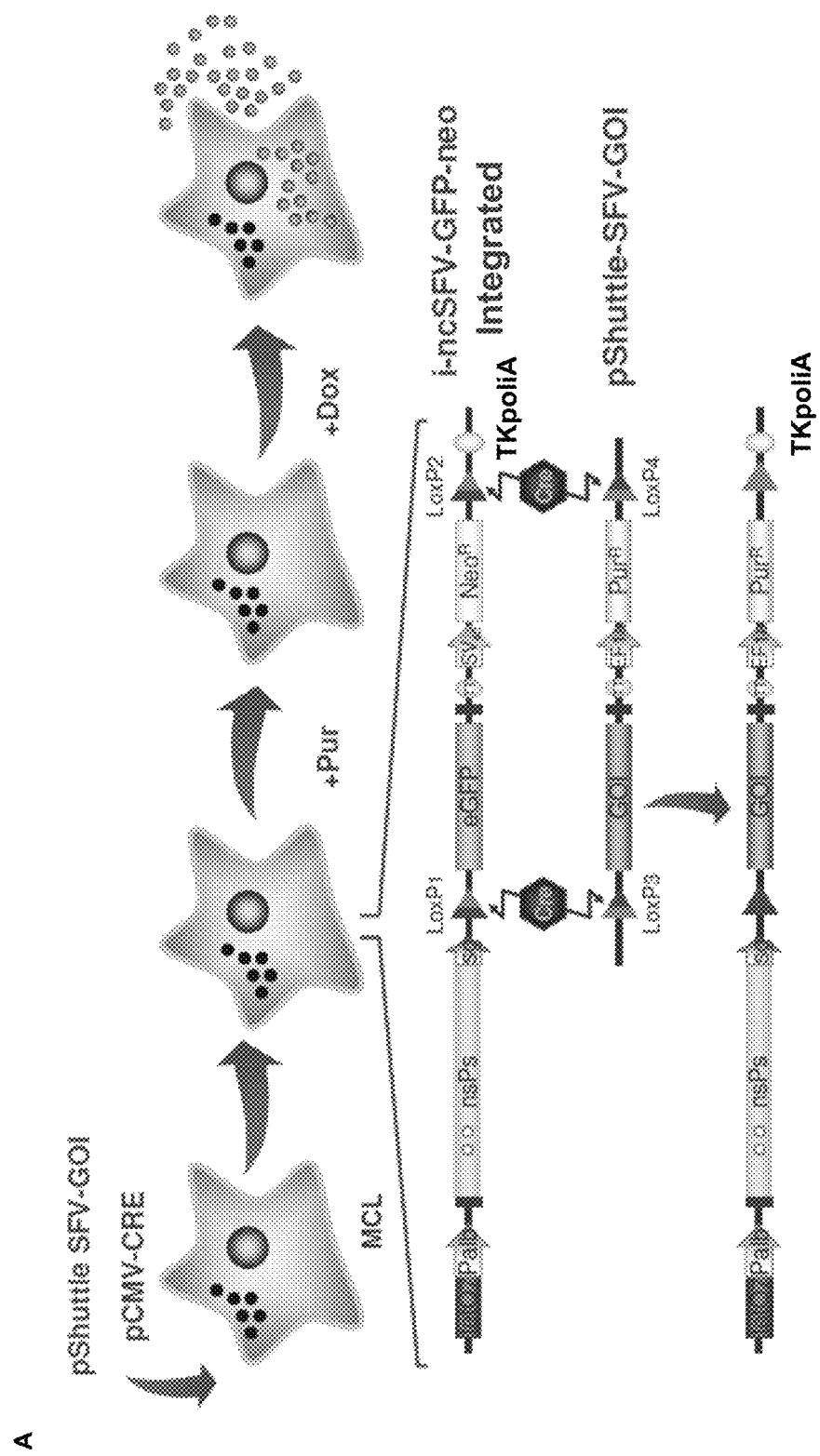
FIG. 7 shows the Cre recombinase-mediated transgene exchange. (A) Schematic representation of the process of selecting new cell lines. To generate a stable line expressing the gene of interest (GOI), MCL was co-transfected with a plasmid encoding Cre recombinase (pCMV-CRE) and with a pSFV-Shuttle plasmid carrying the gene of interest (pShuttle-SFV-GOI). After Cre-mediated recombination, the GFP gene is substituted with the GOI gene, and the cells become neomycin-sensitive and puromycin-resistant, which can be used for selecting the new cell line. (B) Evaluation of transgene exchange using the Tomato gene as the GOI. MCL was transfected with 1 µg of pCMV-CRE and 2 µg pShuttle-SFV-Tomato. After 24 h, puromycin at a final concentration of 5 µg/mL was added and cells were selected until reaching confluence. Once selected, the new MCL was evaluated to determine Tomato and GFP expression by means of fluorescence (using the indicated filter) after induction with DOX at a concentration of 1.25 µg/mL for 5 days, using MCL as a control. sg, subgenomic promoter; EF1α, elongation factor 1-alpha promoter.
Figure 7:
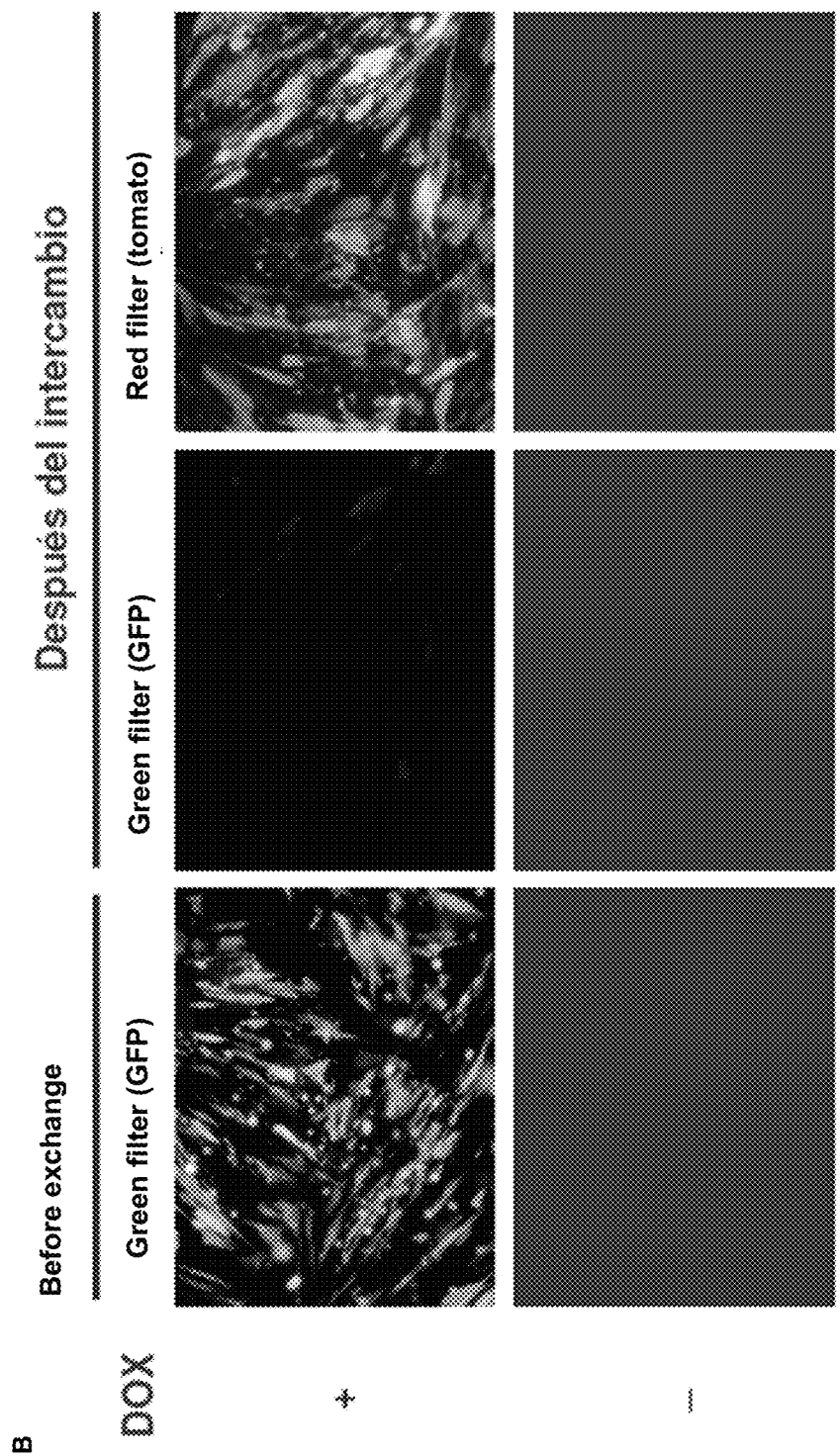

Example 4: Generation of New Stable Lines Derived from MCL by Means of the Recombinase-Mediated Transgene Exchange To generate new, quickly and easily inducible stable lines, a strategy was designed to exchange the GFP gene and the neomycin resistance gene present in MCL with a DNA fragment containing a new transgene of interest and the gene conferring puromycin resistance (pac), by means of a Cre recombinase-mediated recombination process. To that end, mutant LoxP sites had been previously introduced in two positions of the i-ncSFV-GFP-neo vector integrated in MCL (FIG. 1). The first LoxP site (LoxP1) was cloned between the SFV subgenomic promoter and the GFP gene, whereas the second LoxP site (LoxP2) was cloned between the neomycin resistance gene and its polyadenylation signal (FIG. 7A). LoxP1 and LoxP2 sites contain mutations preventing recombination between them (Table 2), but allowing unidirectional recombination with LoxP sites containing complementary mutations (Lee and Saito 1998, Gene 216(1): 55-65; Arakawa, Lodygin et al. 2001, BMC Biotechnol 1: 7). The combination of these two types of mutations in the same LoxP sites had not been previously described. In order to introduce a new transgene of interest in the MCL, a shuttle vector (pShuttle-SFV) containing a multiple cloning site was constructed in which the desired transgene can be introduced followed by the SFV 3' end and the pac gene devoid of its polyadenylation signal (FIG. 7A). This cassette was flanked by LoxP sites (LoxP3 and LoxP4) also containing mutations preventing recombination between them but allowing unidirectional and irreversible recombination with LoxP1 and LoxP2 sites, respectively (Table 2). To verify this exchange system, a pSFV-shuttle vector containing the Tomato gene, encoding a red fluorescent protein (pShuttle-SFV-Tomato), was generated. The MCL was co-transfected with pShuttle-SFV-Tomato and with a plasmid expressing Cre recombinase (pCMV-CRE), and puromycin was added at a concentration of 5 µg/mL after 24 h. A puromycin-resistant cell culture was thus obtained, in which a high proportion of cells expressed Tomato after the addition of DOX without any GFP expression being observed (FIG. 7B). The fact that 40% of the puromycin-resistant cells did not express Tomato in this culture indicated that the correct exchange had not taken place in 100% of the cells. Nevertheless, the fact that a high proportion of cells could express the new gene of interest makes individual clone selection and growth considerably easier.

Example 5: Generation of Stable Cell Lines Expressing Human Cardiotrophin-1 (CT-1)

Figure 10:
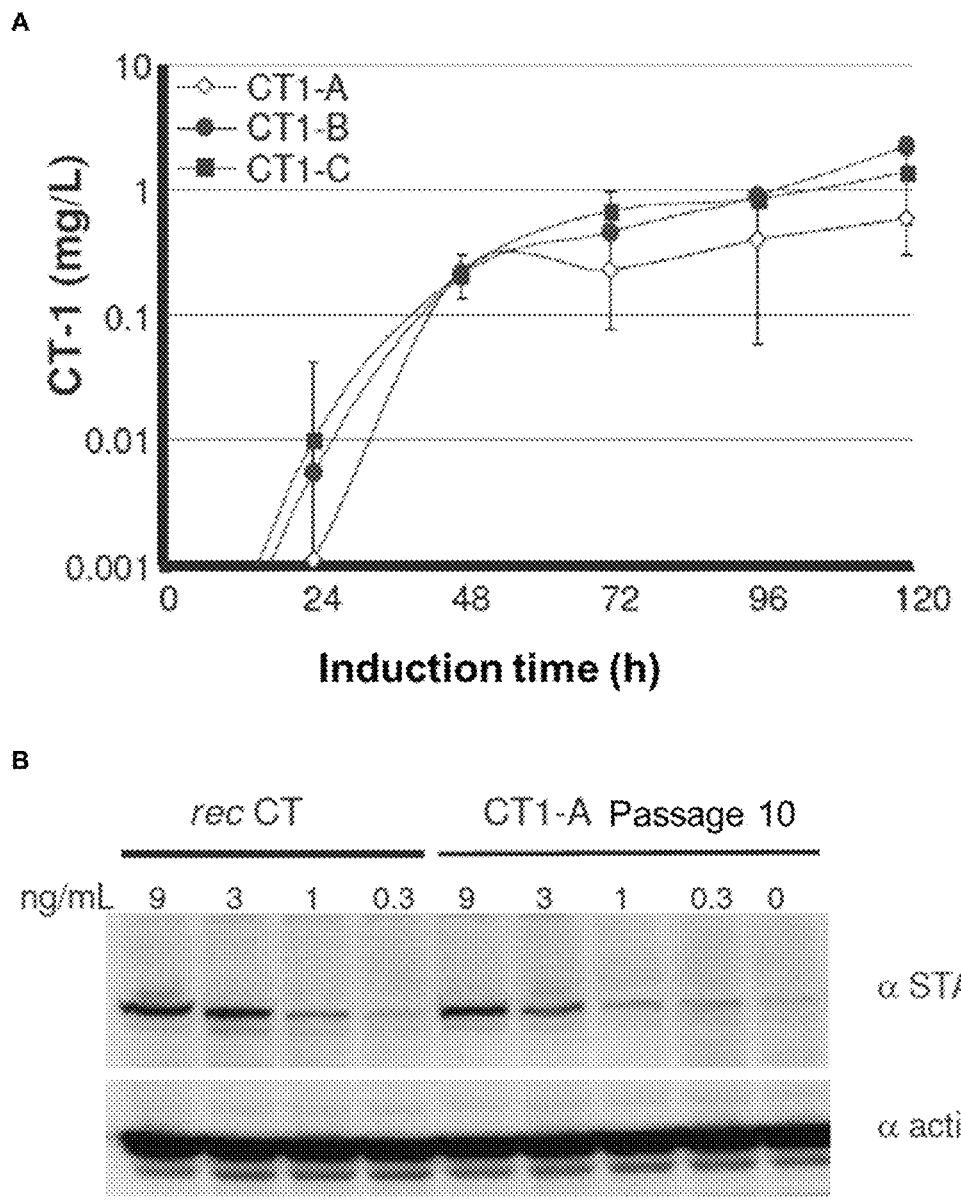
FIG. 10 shows the induction kinetics and determination of CT-1 and OSM biological activity. To determine the kinetics of CT-1 and OSM expression, the selected clones were induced for 5 days at 33° C. with 2.5 µg/mL DOX, the supernatants were collected every 24 h, and the amount of secreted recombinant protein was measured by means of a specific ELISA (A and C). The functional activity of the CT-1 and OSM present in the supernatants of the indicated clones and passes was evaluated by means of the capacity thereof to induce STAT3 phosphorylation in HepG2 cells (for CT-1) (B) or Huh7 cells (for OSM) (D). rec, commercial recombinant proteins produced in bacteria. Loading control, non-specific band present in all samples.
Figure 10:
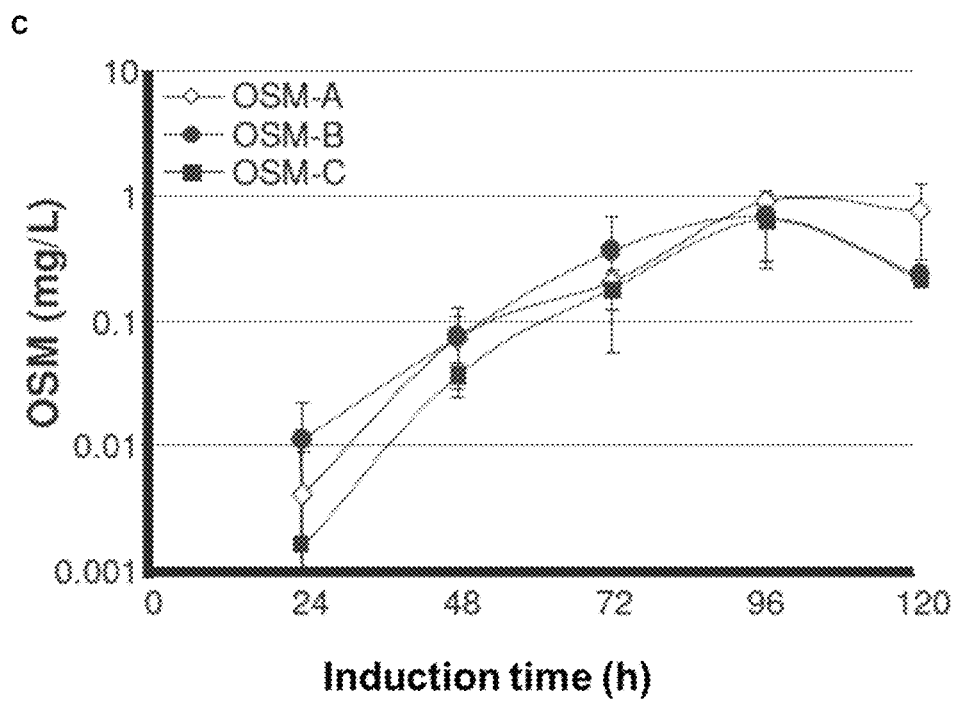
Figure 10:
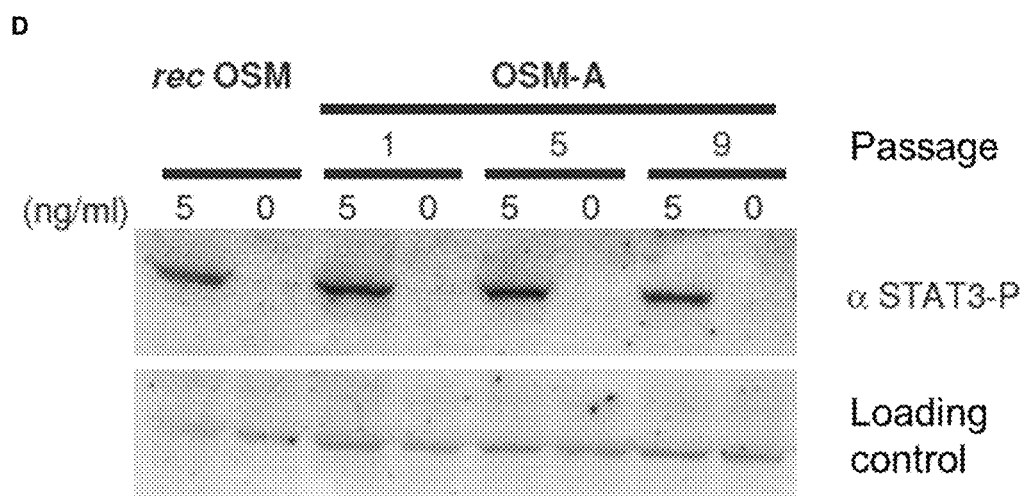

To verify if the inducible lines which have been described could be used for producing therapeutic proteins, the CT-1 gene was cloned into the pShuttle-SFV vector fused with a signal peptide and with a 6-histidine tag at the $NH_2$ end (pShuttle-SFV-CT, FIG. 8A). This vector was co-transfected with pCMV-CRE in MCL and puromycin was added at 5 µg/ml after 24 h. By means of terminal dilution, three clones (CT1-A, CT1-B and CT1-C) were selected in which CT-1 expression drastically increased after 48 h of induction, reaching a concentration in the supernatants of 3 mg/L/24 h after 120 h (FIG. 10A). The three clones showed high stability with CT-1 expression levels of 1-5 mg/L in 10 consecutive passes and the total absence of expression when no DOX was added (FIGS. 8B and 8C). The CT-1 produced by these lines proved to be functional since it was capable of inducing STAT3 phosphorylation in HepG2 cells incubated in the absence of serum for 48 h (FIG. 10B). This activity was maintained in all the analyzed passes (3, 5 and 10 for each clone) and was equal to or greater than that of commercial CT-1.

Example 6: Generation of Stable Cell Lines Expressing Oncostatin-M (OSM)

Figure 11:
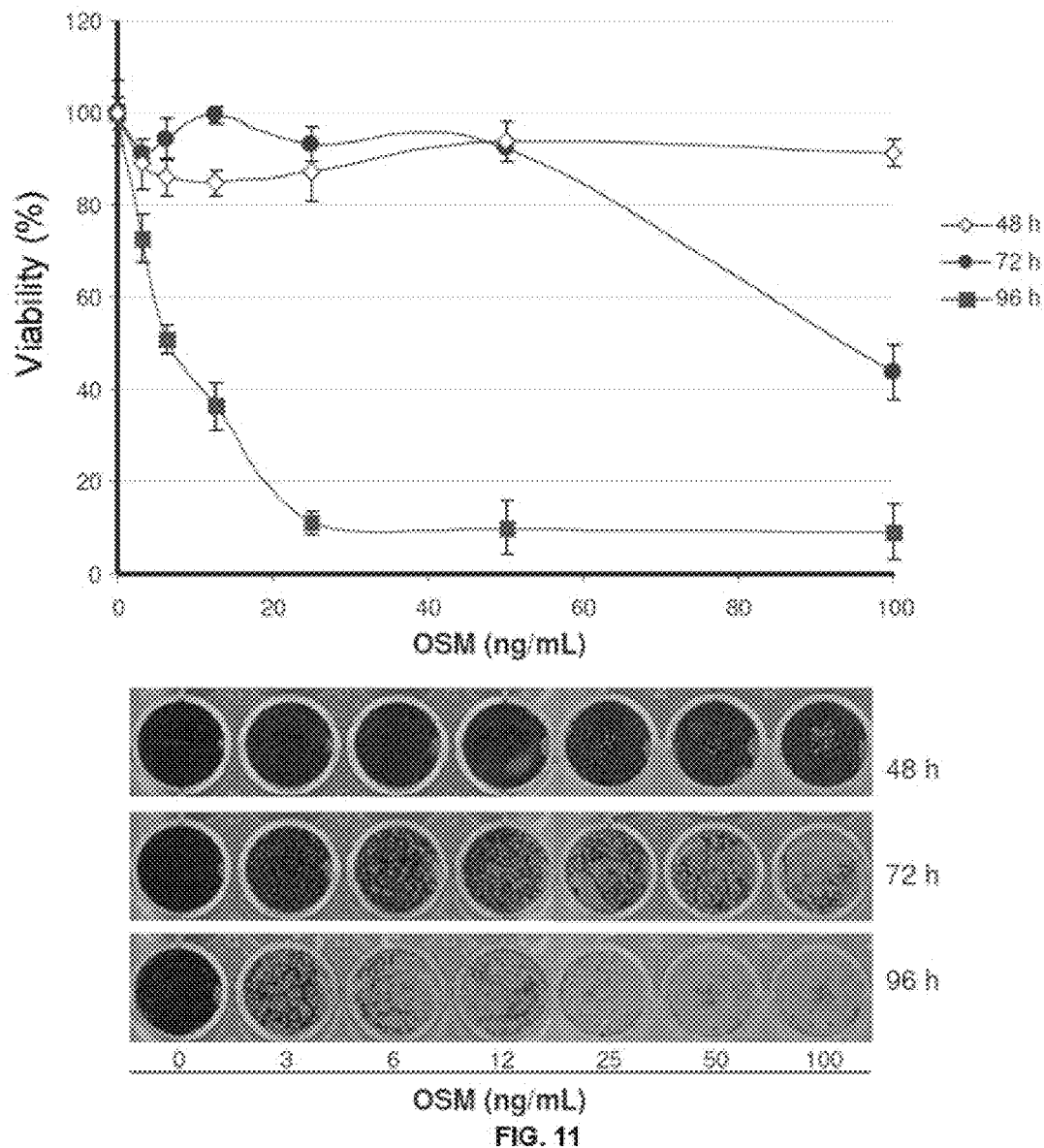
FIG. 11 shows OSM toxicity evaluation in BHK cells. BHK cells were seeded in 24-well plates with $1\times10^5$ cells/well and treated 24 h later with the indicated concentrations of OSM. Cells were washed with PBS at the indicated times, and those that remain adhered were stained with crystal violet (Sigma, St. Louis, Mo., USA). The amount of adhered cells was determined by dissolving the dye with 10% acetic acid and measuring absorbance at 595 nm. The percentage of survival was calculated as the percentage of absorbance relative to that of cells which were not incubated with OSM.

OSM is a cytokine of the interleukin-6 family with antitumor and antiviral properties (Larrea, Aldabe et al., 2009, J Virol 83(7): 3298-311) and is capable of inhibiting the growth of various cell lines (Horn, Fitzpatrick et al., 1990, Growth Factors 2(2-3): 157-65). This inhibitory effect has also been observed in cell lines commonly used for producing recombinant proteins, such as BHK cells (FIG. 11), which greatly complicates production of this protein. An important advantage of the ncSFV inducible expression system is that it could be used for expressing proteins that are toxic for the producing cells, since these cells could be grown to the desired density and number before inducing expression. To test this hypothesis, the gene encoding the mature form of OSM was cloned into the pShuttle-SFV vector as described in Materials and Methods, the pShuttle-SFV-OSM plasmid being generated (FIG. 9A). This vector was co-transfected along with pCMV-CRE in the MCL, after which the cells were selected with puromycin at 5 µg/ml. By means of terminal dilution, three clones (OSM-A, OSM-B and OSM-C) were selected in which OSM expression drastically increased after h of induction, reaching a concentration in the supernatants of 1 mg/L/24 h after 96 h (FIG. 10C). After 72 h of induction, cultures expressing OSM showed a strong cytopathic effect, which was not observed in non-induced cultures or in those expressing CT-1 (FIGS. 8D and 9D). The three clones showed high stability, showing OSM expression levels of 1-8 mg OSM/L in 10 consecutive passes and with the total absence of expression when no DOX was added (FIGS. 9B and 9C). The OSM produced by these lines proved to be functional since it was capable of inducing STAT3 phosphorylation in Huh7 cells incubated in the absence of serum for 48 h (FIG. 10D). This activity was maintained in all the analyzed passes (1, 5 and 10 for each clone) and was equal to or greater than that of commercial OSM. This data confirms that the i-ncSFV system can be used for generating stable lines expressing toxic functional proteins at high levels and with high stability.

Example 7: Generation and Characterization of Stable Cell Lines Expressing Monoclonal Antibodies To establish if the system of the present invention was capable of producing monoclonal antibodies (mAbs), a line expressing the A20 idiotypic antibody derived from a murine follicular lymphoma was generated. To that end, the genes encoding the antibody light chain (LC) and heavy chain (HC) were cloned into the pShuttle-SFV vector under the control of independent subgenomic promoters, the pShuttle-SFV-A20 vector being generated (FIG. 12A). Said vector was co-transfected with pCMV-CRE in the MCL and puromycin was added at a final concentration of 5 µg/ml after 24 h. After selecting the cells, the culture was induced with doxycycline and expression of the monoclonal antibody was evaluated in the supernatant by means of Western Blot in non-reductive conditions, confirming that the system allows correct antibody expression, reaching expression levels of up to 8 mg/L/24 h (FIG. 12B).

Example 8: Biochemical Purification and Characterization of CT-1 and OSM Expressed from Lines Carrying the i-ncSFV Vector To purify CT-1 and OSM, clones CT1-A and OSM-A were grown until obtaining a final amount of $10^8$ cells and incubated with 100 ml of medium supplemented with DOX for 3 or 4 days, respectively. At that time, the medium was replaced with serum-free medium and CT-1 and OSM were purified after 24 h from the cell supernatant by means of $Ni^2$-nitrilotriacetic columns (QIAGEN, Germany). The purification yield was 0.69 mg/L for CT-1 and 1.54 mg/L for OSM (Table 3). The identity of each protein was confirmed by means of LC-MS/MS analysis.

TABLE 3

Purification of CT-1 and OSM from i-ncSFV-derived cell lines

| CT-1 | Volume (mL)[a] | CT-1 (mg/L)[b] | Total CT-1 (μg) | Recovery (%) |
|---|---|---|---|---|
| CT-1, supernatant | 100 | 4.6 | 460 | NA[d] |
| Ni-NTA chromatography | 1 | 68.8 | 69 | 15 |

| OSM | Volume (mL)[a] | OSM (mg/L)[b] | Total OSM (μg) | Recovery (%) |
|---|---|---|---|---|
| OSM, supernatant | 100 | 3.6 | 360 | NA |
| Ni-NTA chromatography | 1 | 154.0 | 154 | 43 |

[a]Volume of the CT-1 or OSM solution.
[b]CT-1/OSM concentration determined by means of ELISA.
[c]1 AU: degree of STAT3 phosphorylation produced by 1 ng of commercial recombinant CT-1/OSM.
[d]NA: Not applicable.

Figure 13:
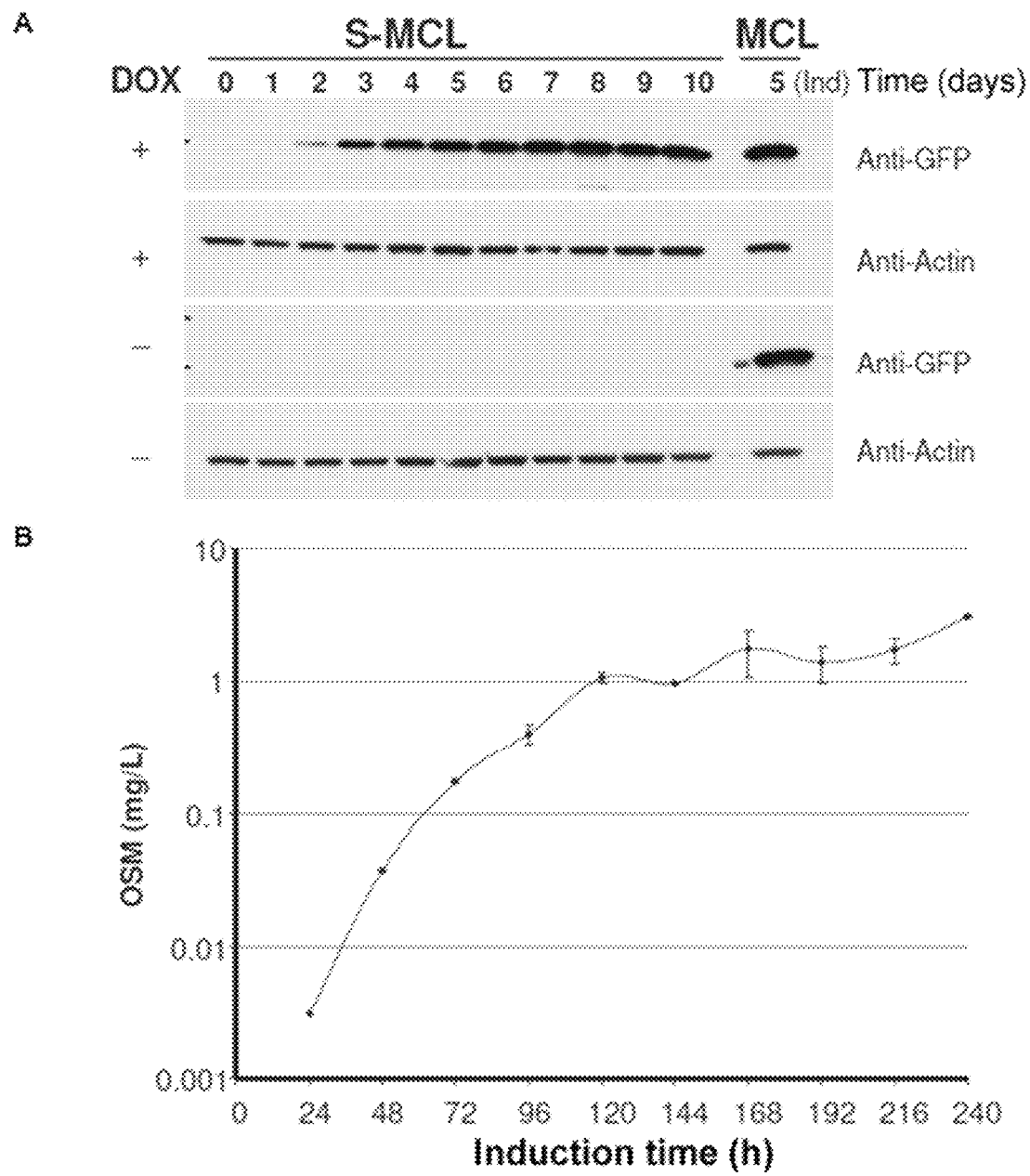
FIG. 13 shows the kinetics of expression in cell lines adapted to grow in suspension. (A) MCL adapted to grow in suspension (S-MCL) was incubated with 2 µg/mL of DOX (+) or without DOX (−) at 33° C., and GFP expression in the cell lysates was analyzed at the indicated times by means of Western blot. MCL, adherent MCL cells incubated for 5 days with DOX. (B) The OSM-A line was adapted to grow in suspension, induced with DOX as described, and OSM expression in the supernatant was evaluated by means of a specific ELISA at the indicated times.

Example 9: Adaptation of the Selected Inducible Lines to Growing in Suspension and without Serum In a first phase, cultures in suspension of the MCL line and the OSM-A clone were started by means of culturing trypsinized cells in flasks under agitation (spinner flasks) using a medium specifically formulated for cells in suspension containing 10% serum. After three weeks of culture with periodic passes, the two lines had adapted to grow in suspension. In a second phase, the cultures were subjected to several passes in which the serum concentration was progressively reduced until it was completely removed, a process that took about one month. Both the MCL line and the OSM-A line adapted to grow in suspension were capable of expressing high levels of GFP and OSM, respectively, when induced at 33° with doxycycline (FIG. 13).

The invention claimed is:

1. A polynucleotide comprising
   (i) a transcription regulatory sequence,
   (ii) a DNA sequence complementary to an alphavirus replicon, wherein said alpharivus replicon comprises, ordered from the 5' to 3'end:
      a 5' sequence capable of directing replication of the alphavirus,
      a nucleotide sequence encoding a polyprotein comprising the sequences of non-structural proteins nsp1, nsp2, nsp3 and nsp4 of an alphavirus,
      an alphavirus subgenomic promoter, and
      an alphavirus 3' untranslated sequence,
      wherein the DNA sequence complementary to an alphavirus replicon is operatively bound to said transcription regulatory sequence, and wherein said alphavirus replicon complementary sequence comprises a first recognition sequence for a site-specific recombinase located between the sequence complementary to the alphavirus replicon subgenomic promoter and the sequence complementary to the alphavirus replicon 3' untranslated sequence,
   (iii) a transcription termination sequence positioned 3' with respect to the 3' end of the sequence complementary to said alphavirus replicon, and
   (iv) a second recognition sequence for a site-specific recombinase positioned 3' with respect to the transcription termination sequence.

2. The polynucleotide according to claim 1, wherein the recognition sequences for a site-specific recombinase are heterospecific sequences.

3. The polynucleotide according to claim 1, wherein the recognition sequences for a site-specific recombinase are LoxP sequences.

4. The polynucleotide according to claim 3, wherein the first and second LoxP sequences are selected from the group consisting of the pairs
   (a) SEQ ID NO: 9 and SEQ ID NO: 10,
   (b) SEQ ID NO: 11 and SEQ ID NO: 12,
   (c) SEQ ID NO: 9 and SEQ ID NO: 12,
   (d) SEQ ID NO: 11 and SEQ ID NO: 10,
   (e) SEQ ID NO: 10 and SEQ ID NO: 9,
   (f) SEQ ID NO: 12 and SEQ ID NO: 11,
   (g) SEQ ID NO: 10 and SEQ ID NO: 11, and
   (h) SEQ ID NO: 12 and SEQ ID NO: 9.

5. The polynucleotide according to claim 4, wherein the transcription regulatory sequence comprises a eukaryotic promoter or a minimal variant thereof.

6. The polynucleotide according to claim 5, wherein the promoter is the minimal albumin gene promoter or a functionally equivalent variant thereof.

7. The polynucleotide according to claim 1, wherein the transcription regulatory sequence has regulable activity.

8. The polynucleotide according to claim 7, wherein the transcription regulatory sequence having regulable activity additionally comprises an inducing agent responsive element.

9. The polynucleotide according to claim 8, wherein the inducing agent responsive element is a ligand responsive element.

10. The polynucleotide according to claim 9, wherein the ligand responsive element is a tetracycline or tetracycline analogue responsive element.

11. The polynucleotide according to claim 5, wherein the transcription regulatory sequence comprises the nucleotide sequence SEQ ID NO: 5.

12. The polynucleotide according to claim 11, wherein the transcription regulatory sequence comprises the nucleotide sequence SEQ ID NO: 8, and wherein the transcription regulatory sequence does not comprise the sequence SEQ ID NO: 4.

13. The polynucleotide according to claim 1, wherein the DNA sequence complementary to an alphavirus replicon further comprises a heterologous sequence positioned 3' with respect to the sequence complementary to the replicon subgenomic promoter and with respect to the first recognition sequence for a site-specific recombinase.

14. The polynucleotide according to claim 13, wherein said heterologous sequence is selected from the group consisting of
   (i) a stuffer sequence,
   (ii) a sequence comprising a multiple cloning site,
   (iii) a sequence of a gene of interest operatively bound to the sequence complementary to the alphavirus replicon subgenomic promoter, and
   (iv) any combination thereof.

15. The polynucleotide according to claim 14, wherein said heterologous sequence is a sequence of a gene of interest operatively bound to the sequence complementary to the alphavirus replicon subgenomic promoter, and wherein the gene of interest encodes a protein of interest or a precursor thereof.

16. The polynucleotide according to claim 14, wherein the polynucleotide comprises at least one sequence of a second gene of interest, wherein said sequence of a second gene of interest is positioned 3' with respect to the first recognition sequence for a site-specific recombinase in the polynucleotide, and wherein said sequence of a second gene of interest is operatively bound to a sequence complementary to an additional subgenomic promoter or is operatively bound with the sequence of the first gene of interest by means of an IRES or a sequence encoding a post-translational proteolytic cleavage site.

17. The polynucleotide according to claim 16, wherein the first gene of interest and the second gene of interest encode a first and a second antibody chain, respectively.

18. The polynucleotide according to claim 1, wherein the alphavirus replicon is a Semliki Forest Virus replicon.

19. The polynucleotide according to claim 18, wherein the Semliki Forest Virus replicon comprises at least one mutation conferring said replicon a non-cytopathic phenotype.

20. The polynucleotide according to claim 19, wherein said mutation is located in the region encoding the nsp2 subunit of the viral replicase and wherein said mutation is selected from the group consisting of mutations P718T, R649H and a combination of both.

21. The polynucleotide according to claim 1, additionally comprising a selection gene, wherein said selection gene is located in the region comprised between the first and second recombinase recognition sites, and wherein (i) if the transcription regulatory sequence which is operatively bound to the alphavirus replicon complementary sequence is a regulable sequence, then the selection gene is located outside said replicon and bound to a constitutive promoter, or (ii) if the transcription regulatory sequence which is operatively bound to the alphavirus replicon complementary sequence comprises a constitutive promoter, then said selection gene is operatively associated with the gene of interest by means of an IRES or a sequence encoding a post-translational proteolytic cleavage site, or said selection gene is under the control of a second constitutive promoter.

22. The polynucleotide according to claim 21, wherein the constitutive promoter to which the selection gene is bound comprises the nucleotide sequence which is shown in SEQ ID NO: 14.

23. The polynucleotide according to claim 21, wherein the selection gene is a gene conferring antibiotic resistance.

24. The polynucleotide according to claim 23, wherein the gene conferring antibiotic resistance is selected from the group consisting of the neomycin resistance gene and the puromycin resistance gene.

25. The polynucleotide according to claim 1, additionally comprising a polyadenylation signal or a polyadenylation and transcription termination signal positioned 3' with respect to the second recombinase recognition site.

26. The polynucleotide according to claim 25, wherein the polyadenylation and transcription termination signal comprises the sequence SEQ ID NO: 70.

27. A eukaryotic cell comprising a polynucleotide according to claim 1, wherein the polynucleotide is integrated in the genome thereof.

28. The cell according to claim 27, wherein the transcription regulatory sequence which is operatively bound to the alphavirus replicon complementary sequence is a regulable sequence, and wherein said cell additionally comprises an DNA sequence encoding a transcriptional activator operatively bound to a constitutive promoter, wherein said transcriptional activator is capable of regulating transcription from said transcription regulatory sequence by means of the binding thereof to the ligand responsive site, and wherein the DNA sequence encoding a transcriptional activator is integrated in the genome.

29. An in vitro method for generating a cell line capable of expressing a gene of interest which comprises
(i) contacting a cell with a polynucleotide according to claim 1, wherein said polynucleotide additionally comprises said gene of interest operatively bound to the sequence complementary to the replicon subgenomic promoter, or with an expression vector comprising said polynucleotide, and
(ii) selecting cells that have incorporated said polynucleotide or an expression vector comprising said polynucleotide.

30. A method for expressing a gene of interest which comprises putting a eukaryotic cell in suitable conditions for activating transcription of the sequence complementary to the alphaviral replicon, wherein said cell comprises a polynucleotide according to claim 1 or an expression vector comprising said polynucleotide, wherein said polynucleotide additionally comprises the sequence of the gene of interest operatively bound to the subgenomic promoter.

31. A vector comprising a DNA sequence comprising, ordered in the 5' to 3' direction,
(i) a first recognition sequence for a site-specific recombinase,
(ii) a sequence of a gene of interest,
(iii) a 3' sequence necessary for replication of an alphavirus,
(iv) a transcription termination sequence,
(v) a sequence of a selection gene operatively bound to a promoter, and
(vi) a second recognition sequence for a site-specific recombinase.

32. An in vitro method for generating a cell line capable of expressing a gene of interest, comprising the steps of:
(i) introducing in a cell according to claim 27 a vector, wherein:
(a) said cell comprises a heterologous sequence positioned 3' with respect to the sequence complementary to the replicon subgenomic promoter, wherein said heterologous sequence is a sequence of a gene of interest operatively bound to the sequence complementary to the subgenomic promoter,
(b) the first recognition sequence of the polynucleotide comprising the alphavirus replicon complementary sequence is compatible with the first heterospecific recognition sequence of the vector,
(c) the second recognition sequence of the polynucleotide comprising the alphavirus replicon complementary sequence is compatible with the second heterospecific recognition sequence of the vector,
(d) the cell expresses a specific recombinase of said first and second recognition sequences, and
(e) the sequence necessary for replication of the alphavirus present in the vector coincides with the sequence necessary for replication of the alphavirus which is part of the alphaviral replicon,
(ii) maintaining the cell in suitable conditions to allow substitution by means of specific recombination of the gene of interest which is part of the polynucleotide comprising the alphavirus replicon complementary sequence with the gene of interest which is part of the vector, and
(iii) selecting the cells in which substitution of the first gene of interest with the second gene of interest has occurred,
wherein the vector comprises a DNA sequence comprising, ordered in the 5' to 3' direction,
(A) a first recognition sequence for a site-specific recombinase,
(B) a sequence of a gene of interest,
(C) a 3' sequence necessary for replication of an alphavirus,
(D) a transcription termination sequence,
(E) a sequence of a selection gene operatively bound to a promoter, and
(F) a second recognition sequence for a site-specific recombinase.

* * * * *